United States Patent
Jang et al.

(10) Patent No.: US 11,149,084 B2
(45) Date of Patent: Oct. 19, 2021

(54) ANTIBODIES THAT BIND TO PATHOLOGICAL TAU SPECIES AND USES THEREOF

(71) Applicant: APRINOIA THERAPEUTICS LIMITED, Wan Chai (CN)

(72) Inventors: Ming-Kuei Jang, Taipei (TW); Chin-Yin Tai, Taipei (TW)

(73) Assignee: APRINOIA THERAPEUTICS LIMITED, Hong Kong (CN)

( * ) Notice: Subject to any disclaimer, the term of this patent is extended or adjusted under 35 U.S.C. 154(b) by 0 days.

(21) Appl. No.: 17/170,446

(22) Filed: Feb. 8, 2021

(65) Prior Publication Data

US 2021/0163582 A1 Jun. 3, 2021

Related U.S. Application Data

(63) Continuation-in-part of application No. PCT/IB2020/057415, filed on Aug. 5, 2020.

(60) Provisional application No. 62/883,605, filed on Aug. 6, 2019.

(51) Int. Cl.
| | | |
|---|---|---|
| *C07K 16/18* | (2006.01) | |
| *A61K 47/68* | (2017.01) | |
| *A61P 25/28* | (2006.01) | |
| *A61K 39/395* | (2006.01) | |
| *A61K 45/06* | (2006.01) | |
| *G01N 33/68* | (2006.01) | |
| *A61K 39/00* | (2006.01) | |

(52) U.S. Cl.
CPC .......... *C07K 16/18* (2013.01); *A61K 39/3955* (2013.01); *A61K 45/06* (2013.01); *A61K 47/6803* (2017.08); *A61K 47/6843* (2017.08); *A61P 25/28* (2018.01); *G01N 33/6896* (2013.01); *A61K 2039/505* (2013.01); *C07K 2317/24* (2013.01)

(58) Field of Classification Search
CPC .............. C07K 16/18; C07K 2317/565; C07K 2317/24; C07K 14/4711; A61K 39/0007; A61K 39/3955; A61K 47/6843
See application file for complete search history.

(56) References Cited

FOREIGN PATENT DOCUMENTS

| | | |
|---|---|---|
| WO | WO-2018/011073 A1 | 1/2018 |
| WO | WO-2018/017370 A1 | 1/2018 |

OTHER PUBLICATIONS

Braak, Heiko, et al., "Staging of Alzheimer disease-associated neurofibrillary pathology using paraffin sections and immunocytochemistry," Acta Neuropathol (2006), vol. 112, pp. 389-404.
Braak, Heiko, et al., "Staging of Alzheimer's Disease-Related Neurofibrillary Changes," Neurobiology of Aging, vol. 16, No. 3, (1995), pp. 271-284.
DeVos, Sarah L., et al., "Synaptic Tau Seeding Precedes Tau Pathology in Human Alzheimer's Disease Brain," Frontiers in Neuroscience, Apr. 2018, vol. 12, Article 267, 15 pages.
International Search Report dated Jan. 29, 2021 issued in International Application No. PCT/IB2020/057415, 10 pages.
Kfoury, Najla, et al., "Trans-cellular Propagation of Tau Aggregation by Fibrillar Species," The Journal of Biological Chemistry, vol. 287, No. 23, (2012), pp. 19440-19451.
Rudikoff, Stuart, et al., "Single amino acid substitution altering antigen-binding specificity," Proc. Natl. Acad. Sci. USA, vol. 79, (1982), pp. 1979-1983.
Sanders, David W., et al., "Distinct Tau Prion Strains Propagate in Cells and Mice and Define Different Tauopathies," Neuron, vol. 82, (2014), pp. 1271-1288.
Song, Lixin, et al., "Analysis of tau post-translational modifications in rTg4510 mice, a model of tau pathology," Molecular Neurodegeneration, (2015), 10:14, 11 pages.

*Primary Examiner* — Robert C Hayes
(74) *Attorney, Agent, or Firm* — Foley & Lardner LLP

(57) ABSTRACT

The present disclosure relates to antibodies that bind selectively to pathological Tau, including compositions and methods relating to such antibodies, such as for treating tauopathies, neurodegenerative diseases associated with pathological aggregation of Tau.

13 Claims, 14 Drawing Sheets

Specification includes a Sequence Listing.

SEQUENCE LISTING

<160> NUMBER OF SEQ ID NOS: 109

<210> SEQ ID NO 1
<211> LENGTH: 117
<212> TYPE: PRT
<213> ORGANISM: Artificial sequence
<220> FEATURE:
<223> OTHER INFORMATION: Synthetic construct

<400> SEQUENCE: 1

```
Glu Val Gln Leu Val Glu Ser Gly Gly Asp Leu Val Glu Ser Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Asn Ser Glu Asp Thr Ala Met Tyr Tyr Cys
                85                  90                  95

Ala Asp Thr Tyr Tyr Gly Ala Met Asp Tyr Trp Gly Gln Gly Thr Ser
                100                 105                 110

Val Thr Val Ser Ser
            115
```

<210> SEQ ID NO 2
<211> LENGTH: 118
<212> TYPE: PRT
<213> ORGANISM: Artificial sequence
<220> FEATURE:
<223> OTHER INFORMATION: Synthetic construct

<400> SEQUENCE: 2

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ser Asn Ser Asp Ser Thr Thr Ile Tyr Tyr Ala Asp Thr Val
    50                  55                  60

Lys Gly Arg Phe Thr Ile Ser Arg Asp Asn Ala Lys Ser Thr Leu Phe
65                  70                  75                  80

Leu Gln Met Thr Ser Leu Arg Ser Glu Asp Thr Ala Met Tyr Tyr Cys
                85                  90                  95

Gly Arg Ser Tyr Tyr Ser Asn Tyr Val Asp Tyr Trp Gly Gln Gly Thr
            100                 105                 110

Thr Leu Thr Val Ser Ser
        115
```

<210> SEQ ID NO 3
<211> LENGTH: 118
<212> TYPE: PRT
<213> ORGANISM: Artificial sequence
<220> FEATURE:
<223> OTHER INFORMATION: Synthetic construct

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ser Asn Ser Asp Ser Thr Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Ser Tyr Tyr Ser Asn Tyr Val Asp Tyr Trp Gly Gln Gly Thr
            100                 105                 110

Leu Val Thr Val Ser Ser
        115
```

<210> SEQ ID NO 4
<211> LENGTH: 114
<212> TYPE: PRT
<213> ORGANISM: Artificial sequence
<220> FEATURE:
<223> OTHER INFORMATION: Synthetic construct

<400> SEQUENCE: 4

```
Glu Val Lys Leu Leu Gln Ser Gly Gly Gly Leu Val Gln Pro Gly Gly
1               5                   10                  15

Ser Leu Lys Val Ser Cys Ala Ala Ser Gly Phe Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Gly Asn Ala Ile Asn Tyr Ala Pro Ser Leu
    50                  55                  60

Lys Asp Lys Phe Ile Val Ser Arg Asp Asn Ala Lys Asn Thr Leu Tyr
65                  70                  75                  80

Leu Gln Met Ser Asn Val Arg Ser Glu Asp Thr Ala Leu Tyr Tyr Cys
                85                  90                  95

Ala Arg Pro Phe Pro Ser Val Trp Gly Thr Gly Thr Thr Val Thr Val
            100                 105                 110

Ser Ser
```

```
<210> SEQ ID NO 5
<211> LENGTH: 113
<212> TYPE: PRT
<213> ORGANISM: Artificial sequence
<220> FEATURE:
<223> OTHER INFORMATION: Synthetic construct

<400> SEQUENCE: 5

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Asn Trp Ala Phe Ala Tyr Trp Gly Gln Gly Thr Leu Val Thr Val Ser
            100                 105                 110

Ala
```

```
<210> SEQ ID NO 6
<211> LENGTH: 116
<212> TYPE: PRT
<213> ORGANISM: Artificial sequence
<220> FEATURE:
<223> OTHER INFORMATION: Synthetic construct

<400> SEQUENCE: 6

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Leu Lys Gln Arg Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Thr Leu Thr Val Asp Lys Ser Ser Ser Thr Val Tyr
```

-continued

```
                65                  70                  75                  80
Met His Leu Ser Ser Pro Thr Ser Glu Asp Ser Ala Val Tyr Tyr Cys
                    85                  90                  95

Val Arg Pro Tyr Gly Asp Leu Asp Tyr Trp Gly Gln Gly Thr Thr Leu
                    100                 105                 110

Thr Val Ser Ser
        115

<210> SEQ ID NO 7
<211> LENGTH: 112
<212> TYPE: PRT
<213> ORGANISM: Artificial sequence
<220> FEATURE:
<223> OTHER INFORMATION: Synthetic construct

<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Phe
                20                  25                  30

Tyr Met Lys Trp Val Lys Gln Ser His Gly Lys Ser Phe Glu Trp Ile
            35                  40                  45

Gly Asp Ile Asp Pro Asn Asn Gly Asp Thr Phe Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                    85                  90                  95

Ala Arg Asp Leu Tyr Trp Gly Gln Gly Thr Thr Leu Thr Val Ser Ser
                    100                 105                 110

<210> SEQ ID NO 8
<211> LENGTH: 120
<212> TYPE: PRT
<213> ORGANISM: Artificial sequence
<220> FEATURE:
<223> OTHER INFORMATION: Synthetic construct

<400> SEQUENCE: 8

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Ala Val His Trp Val Arg Gln Ser Pro Gly Lys Gly Leu Glu Trp Leu
            35                  40                  45

Gly Val Met Trp Ser Gly Gly Ser Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                    85                  90                  95

Arg Met Gly Asp Tyr Asp Gly Val Ala Trp Phe Ala Tyr Trp Gly Gln
                    100                 105                 110

Gly Thr Leu Val Thr Val Ser Ala
        115                 120

<210> SEQ ID NO 9
<211> LENGTH: 117
```

<212> TYPE: PRT
<213> ORGANISM: Artificial sequence
<220> FEATURE:
<223> OTHER INFORMATION: Synthetic construct

<400> SEQUENCE: 9

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr His
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Thr Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Glu Leu Ser Trp Phe Ala Tyr Trp Gly Gln Gly Thr Leu
            100                 105                 110

Val Thr Val Ser Ala
            115

<210> SEQ ID NO 10
<211> LENGTH: 113
<212> TYPE: PRT
<213> ORGANISM: Artificial sequence
<220> FEATURE:
<223> OTHER INFORMATION: Synthetic construct

<400> SEQUENCE: 10

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asp Tyr Asn Gly Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Arg Ser Pro Tyr Trp Gly Gln Gly Thr Leu Val Thr Val Ser
            100                 105                 110

Ala

<210> SEQ ID NO 11
<211> LENGTH: 118
<212> TYPE: PRT
<213> ORGANISM: Artificial sequence
<220> FEATURE:
<223> OTHER INFORMATION: Synthetic construct

<400> SEQUENCE: 11

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Phe Arg Gln Pro Ser Gly Lys Gly Leu Glu
            35                  40                  45

Trp Leu Ala His Ile Trp Trp Asp Asp Asp Lys Tyr Tyr Asn Pro Ala
 50                  55                  60

Leu Lys Ser Arg Leu Thr Ile Ser Lys Asp Thr Ser Lys Asn Gln Val
 65                  70                  75                  80

Phe Leu Lys Ile Ala Asn Val Asp Thr Ala Asp Thr Ala Thr Tyr Tyr
                 85                  90                  95

Cys Ala Arg Arg Gly Ser Asn Ala Leu Asp Tyr Trp Gly Gln Gly Thr
                100                 105                 110

Ser Val Thr Val Ser Ser
            115

<210> SEQ ID NO 12
<211> LENGTH: 123
<212> TYPE: PRT
<213> ORGANISM: Artificial sequence
<220> FEATURE:
<223> OTHER INFORMATION: Synthetic construct

<400> SEQUENCE: 12

Glu Val Gln Leu Gln Gln Ser Gly Pro Glu Leu Val Lys Pro Gly Ala
 1               5                  10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
            35                  40                  45

Gly Asp Ile Asn Pro Asn Thr Gly Gly Thr Ile Tyr Asn Gln Lys Phe
 50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Thr Ala Val Tyr Tyr Cys
                 85                  90                  95

Ala Gly Glu Gly Pro Tyr Tyr Tyr Gly Thr Thr His Pro Phe Ala Tyr
                100                 105                 110

Trp Gly Gln Gly Thr Leu Val Thr Val Ser Ala
            115                 120

<210> SEQ ID NO 13
<211> LENGTH: 112
<212> TYPE: PRT
<213> ORGANISM: Artificial sequence
<220> FEATURE:
<223> OTHER INFORMATION: Synthetic construct

<400> SEQUENCE: 13

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Thr Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly

```
                85                  90                  95

Ser Leu Val Pro Trp Thr Phe Gly Gly Gly Thr Gln Leu Glu Ile Arg
            100                 105                 110

<210> SEQ ID NO 14
<211> LENGTH: 112
<212> TYPE: PRT
<213> ORGANISM: Artificial sequence
<220> FEATURE:
<223> OTHER INFORMATION: Synthetic construct

<400> SEQUENCE: 14

Asp Ile Val Met Thr Gln Ile Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Ser
                85                  90                  95

Thr His Val Pro Pro Thr Phe Gly Gly Gly Thr Lys Leu Glu Ile Lys
            100                 105                 110

<210> SEQ ID NO 15
<211> LENGTH: 112
<212> TYPE: PRT
<213> ORGANISM: Artificial sequence
<220> FEATURE:
<223> OTHER INFORMATION: Synthetic construct

<400> SEQUENCE: 15

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Ser
                85                  90                  95

Thr His Val Pro Pro Thr Phe Gly Gln Gly Thr Lys Leu Glu Ile Lys
            100                 105                 110

<210> SEQ ID NO 16
<211> LENGTH: 112
<212> TYPE: PRT
<213> ORGANISM: Artificial sequence
<220> FEATURE:
<223> OTHER INFORMATION: Synthetic construct

<400> SEQUENCE: 16

Asp Val Leu Met Thr Gln Thr Pro Leu Ser Leu Pro Val Ser Leu Gly
1               5                   10                  15
```

Asp Gln Ala Ser Ile Ser Cys Arg Ser Gln Ser Leu Val Arg Ser
            20                  25                  30

Asn Gly Asn Thr Tyr Leu Glu Trp Tyr Leu Gln Asn Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 17
<211> LENGTH: 112
<212> TYPE: PRT
<213> ORGANISM: Artificial sequence
<220> FEATURE:
<223> OTHER INFORMATION: Synthetic construct

<400> SEQUENCE: 17

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Gly Gly Lys Thr Tyr Leu Asn Trp Leu Leu Gln Arg Pro Gly Gln Ser
        35                  40                  45

Pro Lys Arg Leu Ile Tyr Gln Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Leu Lys
            100                 105                 110

<210> SEQ ID NO 18
<211> LENGTH: 112
<212> TYPE: PRT
<213> ORGANISM: Artificial sequence
<220> FEATURE:
<223> OTHER INFORMATION: Synthetic construct

<400> SEQUENCE: 18

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys

<210> SEQ ID NO 19
<211> LENGTH: 112
<212> TYPE: PRT
<213> ORGANISM: Artificial sequence
<220> FEATURE:
<223> OTHER INFORMATION: Synthetic construct

<400> SEQUENCE: 19

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro His Thr Phe Gly Gly Gly Thr Lys Leu Glu Ile Lys
            100                 105                 110

<210> SEQ ID NO 20
<211> LENGTH: 113
<212> TYPE: PRT
<213> ORGANISM: Artificial sequence
<220> FEATURE:
<223> OTHER INFORMATION: Synthetic construct

<400> SEQUENCE: 20

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys

<210> SEQ ID NO 21
<211> LENGTH: 107
<212> TYPE: PRT
<213> ORGANISM: Artificial sequence
<220> FEATURE:
<223> OTHER INFORMATION: Synthetic construct

<400> SEQUENCE: 21

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105

<210> SEQ ID NO 22
<211> LENGTH: 112
<212> TYPE: PRT
<213> ORGANISM: Artificial sequence
<220> FEATURE:
<223> OTHER INFORMATION: Synthetic construct

<400> SEQUENCE: 22

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 23
<211> LENGTH: 112
<212> TYPE: PRT
<213> ORGANISM: Artificial sequence
<220> FEATURE:
<223> OTHER INFORMATION: Synthetic construct

<400> SEQUENCE: 23

Asp Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
            20                  25                  30

Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Trp Thr Phe Gly Gly Gly Thr Lys Leu Glu Ile Lys
            100                 105                 110

<210> SEQ ID NO 24
<211> LENGTH: 112
<212> TYPE: PRT
<213> ORGANISM: Artificial sequence
<220> FEATURE:
<223> OTHER INFORMATION: Synthetic construct

<400> SEQUENCE: 24

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Gln Thr Phe Gly Gly Gly Thr Lys Leu Glu Ile Lys
            100                 105                 110

<210> SEQ ID NO 25
<211> LENGTH: 351
<212> TYPE: DNA
<213> ORGANISM: Artificial sequence
<220> FEATURE:
<223> OTHER INFORMATION: Synthetic construct

<400> SEQUENCE: 25
gaggtgcagc tggtggagtc tgggggagac ttagtggagt ctggagggtc cctaaaactc     60
tcctgtgcag cctctggatt cactttcagt agctatggca tgtcttgggt tcgccagact    120
ccagacaaga ggctggagtg gtcgcaacc attagtagta gtggtagtta cacctactat    180
ccagacagtg tgaaggggcg attcaccatc tccagagaca atgccaagaa caccctgtac    240
ctgcaaatga gcagtctgaa ctctgaggac acagccatgt attactgtgc tgatacttac    300
tacggagcta tggactactg ggtcaagga acctcagtca ccgtctcctc a              351

<210> SEQ ID NO 26
<211> LENGTH: 354
<212> TYPE: DNA
<213> ORGANISM: Artificial sequence
<220> FEATURE:
<223> OTHER INFORMATION: Synthetic construct

<400> SEQUENCE: 26
gaggtgcagc tggtggagtc tgggggaggc ttagtgaagc ctggagggtc cctgaaactc     60
tcctgtgcag cctctggatt cactttcagt gactatggaa tgcactgggt tcgtcaggct    120
ccagagaagg ggctggagtg ggttgcatac agcaatagtg acagtactac catctactat    180
gcagacacag tgaagggccg attcaccatc tccagagaca atgccaagag caccctgttc    240
ctgcaaatga ccagtctgag gtctgaggac acggccatgt attattgtgg aaggagctac    300
tatagtaact acgttgacta ctggggccaa ggcaccactc tcacagtctc ctca           354

<210> SEQ ID NO 27
<211> LENGTH: 354

```
<212> TYPE: DNA
<213> ORGANISM: Artificial sequence
<220> FEATURE:
<223> OTHER INFORMATION: Synthetic construct

<400> SEQUENCE: 27
gaggtgcagc tggttgaatc tggcggagga ctggttcagc ctggcggatc tctgagactg    60
tcttgtgccg ccagcggctt caccttcagc gattatggca tgcactgggt ccgacaggcc   120
cctggcaaag gacttgagtg gtcgcctac agcaacagcg acagcaccac catctactac    180
gccgacaccg tgaagggcag attcaccatc agccgggaca cgccaagaa cagcctgtac    240 ctgcagatga actccctgag agccgaggac accgccgtgt actactgtgg cagaagctac   300
tactccaact acgtggacta ctggggccag ggcacactgg tcacagtgtc tagc          354

<210> SEQ ID NO 28
<211> LENGTH: 342
<212> TYPE: DNA
<213> ORGANISM: Artificial sequence
<220> FEATURE:
<223> OTHER INFORMATION: Synthetic construct

<400> SEQUENCE: 28
gaggtgaagc ttctccagtc tggaggtggc ctggtgcagc ctggaggatc cctgaaagtc    60
tcctgtgcag cctcaggatt cgattttagt agatactgga tgagttgggt tcggcgggct   120
ccaggaaaag gactagagtg gattggagaa attaatccag atggcaatgc aataaactat   180
gcaccatctc taaaggataa attcatcgtc tccagagaca cgccaaaaa tacgctgtac     240 ctgcaaatga gcaatgtgag atctgaggac acagcccttt attactgtgc acgacctttc   300
cccagcgtct ggggcacagg gaccacggtc accgtctcct ca                       342

<210> SEQ ID NO 29
<211> LENGTH: 339
<212> TYPE: DNA
<213> ORGANISM: Artificial sequence
<220> FEATURE:
<223> OTHER INFORMATION: Synthetic construct

<400> SEQUENCE: 29
caggtgcagc tgaaggagtc aggacctggc ctggtggcgc cctcacagag cctgtccatc    60
acatgcaccg tctcagggtt ctcattaacc ggctatggtg taaactgggt tcgccagcct   120
ccaggaaagg gtctggagtg gctgggaatg atatggggtg atggaagcac agactataat   180
tcagctctca aatccagact gagcatcagc aaggacaact ccaagagcca agttttctta   240
aaaatgaata gtctgcaaac tgatgacaca gccaggtact actgtgccaa ctgggccttt   300
gcttactggg gccaagggac tctggtcact gtctctgca                           339

<210> SEQ ID NO 30
<211> LENGTH: 348
<212> TYPE: DNA
<213> ORGANISM: Artificial sequence
<220> FEATURE:
<223> OTHER INFORMATION: Synthetic construct

<400> SEQUENCE: 30
caggtgcaac tgcagcagtc tgggcctcag ctggttaggc ctggggcttc agtgaagata    60
tcctgcaagg cttctggtta ctcattcacc agctactgga tgcactggct gaagcagagg   120
cctggacaag gtcttgagtg gattggcatg attgatcctt ccgatagtga aactaggtta   180
```

```
aatcagaagt tcaaggacaa ggccacattg actgtagaca aatcctccag tacagtctac    240
atgcacctca gcagcccgac atctgaggac tctgcggtct attactgtgt aaggccgtat    300
ggtgaccttg actactgggg ccaaggcacc actctcacag tctcctca                 348
```

```
<210> SEQ ID NO 31
<211> LENGTH: 336
<212> TYPE: DNA
<213> ORGANISM: Artificial sequence
<220> FEATURE:
<223> OTHER INFORMATION: Synthetic construct

<400> SEQUENCE: 31
gaggtccagc tgcaacagtc tggacctgag ctggtgaagc ctggggcttc agtgaagatg     60
tcctgcaagg cttctggata caccttcact gacttctaca tgaagtgggt gaagcagagc    120
catggaaaga gctttgagtg gattggagat attgatccta acaatggtga tactttctac    180
aaccagaagt tcaagggcaa ggccacattg actgtagaca aatcctccag cacagcctac    240
atgcagctca cagcctgac atctgaggac tctgcagtct attactgtgc aagggatctc     300
tactggggcc aaggcaccac tctcacagtc tcctca                              336
```

```
<210> SEQ ID NO 32
<211> LENGTH: 360
<212> TYPE: DNA
<213> ORGANISM: Artificial sequence
<220> FEATURE:
<223> OTHER INFORMATION: Synthetic construct

<400> SEQUENCE: 32
caggtgcagc tgaagcagtc aggacctggc ctagtgcagc cctcacagag cctgtccatc     60
acctgcacag tctctggttt ctcattaact agttatgctg tacactgggt tcgccagtct    120
ccaggaaagg gtctggagtg gctgggagtg atgtggagtg gtggaagcac agactataat    180
gcagctttca tatccagact gagcatcagc aaggacaatt ccaagagcca agttttcttt    240
aaaatgaaca gtctgcaagc tgatgacaca gccatatatt actgtgccag aatgggtgat    300
tacgacgggg tggcctggtt tgcttactgg ggccaaggga ctctggtcac tgtctctgca    360
```

```
<210> SEQ ID NO 33
<211> LENGTH: 351
<212> TYPE: DNA
<213> ORGANISM: Artificial sequence
<220> FEATURE:
<223> OTHER INFORMATION: Synthetic construct

<400> SEQUENCE: 33
cagatccagt tggtacagtc tggacctgag ctgaagaagc tggagagac agtcaagatc      60 tcctgcaagg cttctgggta tacctttaca acccatggaa tgagctgggt gaaacaggct    120
ccaggaaagg gtttaaagtg gatgggctgg ataaacacct actctggagt gccaacatat    180
actgatgact tcaagggacg gtttgccttc tctttggaaa cctctgccag cactgcctat    240
ttgcagatca acaacctcaa aaatgaggac acggctacat atttctgtgc aagatcagaa    300
ctgtcctggt tgcttactg gggccaaggg actctggtca ctgtctctgc a              351
```

```
<210> SEQ ID NO 34
<211> LENGTH: 339
<212> TYPE: DNA
<213> ORGANISM: Artificial sequence
<220> FEATURE:
<223> OTHER INFORMATION: Synthetic construct
```

<400> SEQUENCE: 34

| caggttcagc tgcagcagtc tggggctgag ctggtgaagc ctggggcctc agtgaagatt | 60 |
| tcctgcaaag cttctggcta cgcattcagt agctactgga tgaactgggt gaagcagagg | 120 |
| cctggaaagg gtcttgagtg gattggacag atttatcctg agatggtga tactgattac | 180 |
| aacggaaagt tcaagggcaa ggccacactg actgcagaca catcctccag cacagcctac | 240 |
| atgcagctca gcagcctgac ctctgaggac tctgcggtct atttctgtgc aagccgatcc | 300 |
| ccttactggg gccaagggac tctggtcact gtctctgca | 339 |

<210> SEQ ID NO 35
<211> LENGTH: 354
<212> TYPE: DNA
<213> ORGANISM: Artificial sequence
<220> FEATURE:
<223> OTHER INFORMATION: Synthetic construct

<400> SEQUENCE: 35

| caggttactc tgaaagagtc tggccctggg atattgcagc cctcccagac cctcagtctg | 60 |
| acttgttctt tctctgggtt ttcactgagc acttttggta tgggtgtagg ctggtttcgt | 120 |
| cagccttcag ggaagggtct ggagtggctg gcacacattt ggtgggatga tgataagtac | 180 |
| tataacccag ccctgaagag tcggctcaca atctccaagg atacctccaa aaaccaggtt | 240 |
| ttcctcaaga tcgccaatgt ggacactgca gatactgcca catactactg tgctcgaagg | 300 |
| ggtagtaatg ctctggacta ctggggtcaa ggaacctcag tcaccgtctc ctca | 354 |

<210> SEQ ID NO 36
<211> LENGTH: 369
<212> TYPE: DNA
<213> ORGANISM: Artificial sequence
<220> FEATURE:
<223> OTHER INFORMATION: Synthetic construct

<400> SEQUENCE: 36

| gaggtccagc tgcaacagtc tggacctgag ctggtgaagc ctggggcttc agtgaagata | 60 |
| ccctgcaagg cttctggata cacattcact gactacaaca tggactgggt gaagcagagc | 120 |
| catggaaaga gccttgagtg gattggagat attaatccta acactggtgg tactatctac | 180 |
| aaccagaagt tcaagggcaa ggccacattg actgtagaca agtcctccag cacagcctac | 240 |
| atggagctcc gcagcctgac atctgaggac actgcagtct attactgtgc aggagagggc | 300 |
| ccttattact acggtactac ccaccctttt gcttactggg gccaagggac tctggtcact | 360 |
| gtctctgca | 369 |

<210> SEQ ID NO 37
<211> LENGTH: 336
<212> TYPE: DNA
<213> ORGANISM: Artificial sequence
<220> FEATURE:
<223> OTHER INFORMATION: Synthetic construct

<400> SEQUENCE: 37

| gatgttttga tgacccaaac tccactctcc ctgcctgtca gtcttggaga tcaagcctcc | 60 |
| atctcttgca gatctagtca gaccattgta catagtaatg gaaacaccta tttagaatgg | 120 |
| tacctgcaga aaccaggcca gtctccaaag ctcctgatct acaaagtttc caaccgattt | 180 |
| tctggggtcc cagacaggtt cagtggcagt ggatcaggga cagatttcac actcaagatc | 240 |

```
agcagagtgg aggctgagga tctgggagtt tattactgct ttcaaggttc acttgttccg    300
tggacgttcg gtggaggcac ccagctggaa atcagg                              336

<210> SEQ ID NO 38
<211> LENGTH: 336
<212> TYPE: DNA
<213> ORGANISM: Artificial sequence
<220> FEATURE:
<223> OTHER INFORMATION: Synthetic construct

<400> SEQUENCE: 38
gatattgtga tgacccaaat tccactctcc ctgcctgtca gtcttggaga tcaagcctcc     60
atctcttgca gatctagtca gagccttgta cacagtaatg gaaacaccta tttacattgg    120
tacctgcaga agccaggcca gtctccaaag ctcctaatct acaaagtttc caaccgattt    180
tctggggtcc cagacaggtt cagtggcagt ggatcaggga cagatttcac actcaagatc    240
agcagagtgg aggctgagga tctgggagtt tatttctgct ttcaaagtac acatgttcct    300
ccgacgttcg gtggaggcac caagctggaa atcaaa                              336

<210> SEQ ID NO 39
<211> LENGTH: 336
<212> TYPE: DNA
<213> ORGANISM: artificial sequence
<220> FEATURE:
<223> OTHER INFORMATION: Synthetic construct

<400> SEQUENCE: 39
gacgtggtca tgacacagag ccctctgagc ctgcctgtga cactgggaca gcctgccagc     60
atcagctgta gaagcagcca gagcctggtg cacagcaacg gcataaccta cctgcactgg    120
tatctgcaga ggcccggaca gtctcccaga ctgctgatct acaaggtgtc caaccggttc    180
agcggcgtgc ccgatagatt ttctggcagc ggctctggca ccgacttcac cctgaagatc    240
tccagagtgg aagccgagga cgtgggcgtg tacttctgct tccaaagcac ccacgtgcca    300
cctacctttg gccagggcac caagctggaa atcaag                              336

<210> SEQ ID NO 40
<211> LENGTH: 336
<212> TYPE: DNA
<213> ORGANISM: Artificial sequence
<220> FEATURE:
<223> OTHER INFORMATION: Synthetic construct

<400> SEQUENCE: 40
gatgttttga tgacccaaac tccactctcc ctgcctgtca gtcttggaga tcaagcctcc     60
atctcttgca gatctagtca gagtcttgta cgtagtaatg gaaacaccta tttagaatgg    120
tacctgcaga acccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
tacacgttcg gagggggac caagctggaa ataaaa                               336

<210> SEQ ID NO 41
<211> LENGTH: 336
<212> TYPE: DNA
<213> ORGANISM: Artificial sequence
<220> FEATURE:
<223> OTHER INFORMATION: Synthetic construct

<400> SEQUENCE: 41
```

```
gatgttgtga tgacccagac tccactcact ttgtcggtta ccattggaca accagcctcc    60
atctcttgta agtcaagtca gagcctctta gatagtggtg aaagacata tttgaattgg    120 ttgttacaga ggccaggcca gtctccaaag cgcctaatct atcaggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttccg   300
ctcacgttcg gtgctgggac caagctggag ctgaaa                              336
```

```
<210> SEQ ID NO 42
<211> LENGTH: 336
<212> TYPE: DNA
<213> ORGANISM: Artificial sequence
<220> FEATURE:
<223> OTHER INFORMATION: Synthetic construct

<400> SEQUENCE: 42
gatgttgtga tgacccagac tccactcact ttgtcggtta ccattggaca accagcctcc    60
atctcttgca agtcaagtca gagcctctta gatagtgatg aaagacata tttgaattgg    120 ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttcca   300
ttcacgttcg gctcggggac aaagttggaa ataaaa                              336
```

```
<210> SEQ ID NO 43
<211> LENGTH: 336
<212> TYPE: DNA
<213> ORGANISM: Artificial sequence
<220> FEATURE:
<223> OTHER INFORMATION: Synthetic construct

<400> SEQUENCE: 43
gatgttgtga tgacccagac tccactcact ttgtcggtta ccattggaca accagcctct    60
atctcttgca agtcaagtca gagcctctta tatagtaatg aaaaaccta tttgaattgg    120 ttattacaga ggccaggcca gtctccaaag cgcctaatct atctggtgtc taaactggac   180
tctggagtcc ctgacaggtt cactggcagt ggatcaggaa cagattttac actgaaaatc   240
agcagagtgg aggctgagga tttggggggtt tattactgcg tgcaaggtac acattttcct   300
cacacgttcg gaggggggac caagctggaa ataaaa                              336
```

```
<210> SEQ ID NO 44
<211> LENGTH: 339
<212> TYPE: DNA
<213> ORGANISM: Artificial sequence
<220> FEATURE:
<223> OTHER INFORMATION: Synthetic construct

<400> SEQUENCE: 44
gatgttgtga tgacccaaac tccactctcc ctgcctgtca gtcttggaga tcaagcctcc    60
atctcttgca gatctagtca gagccttgta cacagtaatg aaacaccta tttacattgg    120 tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttcct   300
ccgtggacgt tcggtggagg caccaagctg gaaatcaaa                           339
```

<210> SEQ ID NO 45
<211> LENGTH: 321
<212> TYPE: DNA
<213> ORGANISM: Artificial sequence
<220> FEATURE:
<223> OTHER INFORMATION: Synthetic construct

<400> SEQUENCE: 45

| | | |
|---|---|---|
| gacattgtga tgactcagtc tccagccacc ctgtctgtga ctccaggaga tagagtctct | 60 |
| ctttcctgca gggccagcca gagtattagc gactacttac actggtatca acaaaaatca | 120 |
| catgagtctc caaggcttct catcaaatat gcttcccaat ccatctctgg gatcccctcc | 180 |
| aggttcagtg gcagtggatc agggtcagat ttcactctca gtatcaacag tgtggaacct | 240 |
| gaagatgttg gagtgtatta ctgtcaaaat ggtcacagct ttccgtacac gttcggaggg | 300 |
| gggaccaagc tggaaataaa a | 321 |

<210> SEQ ID NO 46
<211> LENGTH: 336
<212> TYPE: DNA
<213> ORGANISM: Artificial sequence
<220> FEATURE:
<223> OTHER INFORMATION: Synthetic construct

<400> SEQUENCE: 46

| | | |
|---|---|---|
| gatattttga tgacccaaac tccactctcc ctgcctgtca gtcttggaga tcaagcctcc | 60 |
| atctcttgca gatctagtca gagcattgta catagtaatg aaacaccta tttagaatgg | 120 |
| tacctgcaga aaccaggcca gtctccaaag ctcctgatct acaaagtttc caaccgattt | 180 |
| tctggggtcc cagacaggtt cagtggcagt ggatcaggga cagatttcac actcaagatc | 240 |
| agcagagtgg aggctgagga tctgggagtt tattactgct ttcaaggttc acatgttccg | 300 |
| tacacgttcg gagggggggac caagctggaa ataaaa | 336 |

<210> SEQ ID NO 47
<211> LENGTH: 336
<212> TYPE: DNA
<213> ORGANISM: Artificial sequence
<220> FEATURE:
<223> OTHER INFORMATION: Synthetic construct

<400> SEQUENCE: 47

| | | |
|---|---|---|
| gatgttgtgg tgactcaaac tccactctcc ctgcctgtca gctttggaga tcaagtttct | 60 |
| atctcttgca ggtctagtca gagtcttgca aacagttatg gaacaccta tttgtcttgg | 120 |
| tacctgcaca agcctggcca gtctccacag ctcctcatct atgggatttc aacagattt | 180 |
| tctggggtgc cagacaggtt cagtggcagt ggttcaggga cagatttcac actcaagatc | 240 |
| agcacaataa agcctgagga cttgggaatg tattactgct acaaggtac acatcagccg | 300 |
| tggacgttcg gtggaggcac caagctggaa atcaaa | 336 |

<210> SEQ ID NO 48
<211> LENGTH: 336
<212> TYPE: DNA
<213> ORGANISM: Artificial sequence
<220> FEATURE:
<223> OTHER INFORMATION: Synthetic construct

<400> SEQUENCE: 48

| | | |
|---|---|---|
| gatgttgtga tgacccagac tccactcact ttgtcggtta ccattggaca accagcctct | 60 |
| atctcttgca agtcaagtca gagcctctta tatagtaatg gaaaaaccta tttgaattgg | 120 |

```
ttattacaga ggccaggcca gtctccaaag cgcctaatct atctggtgtc taaactggac    180
tctggagtcc ctgacaggtt cactggcagt ggatcaggaa cagattttac actgaaaatc    240
agcagagtgg aggctgagga tttgggagtt tattactgcg tgcaaggtac acattttcct    300
cagacgttcg gtggaggcac caagctggaa atcaaa                              336
```

<210> SEQ ID NO 49
<211> LENGTH: 5
<212> TYPE: PRT
<213> ORGANISM: Artificial sequence
<220> FEATURE:
<223> OTHER INFORMATION: Synthetic construct

<400> SEQUENCE: 49

Ser Tyr Gly Met Ser
1               5

<210> SEQ ID NO 50
<211> LENGTH: 5
<212> TYPE: PRT
<213> ORGANISM: Artificial sequence
<220> FEATURE:
<223> OTHER INFORMATION: Synthetic construct

<400> SEQUENCE: 50

Asp Tyr Gly Met His
1               5

<210> SEQ ID NO 51
<211> LENGTH: 5
<212> TYPE: PRT
<213> ORGANISM: Artificial sequence
<220> FEATURE:
<223> OTHER INFORMATION: Synthetic construct

<400> SEQUENCE: 51

Arg Tyr Trp Met Ser
1               5

<210> SEQ ID NO 52
<211> LENGTH: 5
<212> TYPE: PRT
<213> ORGANISM: Artificial sequence
<220> FEATURE:
<223> OTHER INFORMATION: Synthetic construct

<400> SEQUENCE: 52

Gly Tyr Gly Val Asn
1               5

<210> SEQ ID NO 53
<211> LENGTH: 5
<212> TYPE: PRT
<213> ORGANISM: Artificial sequence
<220> FEATURE:
<223> OTHER INFORMATION: Synthetic construct

<400> SEQUENCE: 53

Ser Tyr Trp Met His
1               5

<210> SEQ ID NO 54
<211> LENGTH: 5
<212> TYPE: PRT
<213> ORGANISM: Artificial sequence

```
<220> FEATURE:
<223> OTHER INFORMATION: Synthetic construct

<400> SEQUENCE: 54

Asp Phe Tyr Met Lys
1               5

<210> SEQ ID NO 55
<211> LENGTH: 5
<212> TYPE: PRT
<213> ORGANISM: Artificial sequence
<220> FEATURE:
<223> OTHER INFORMATION: Synthetic construct

<400> SEQUENCE: 55

Ser Tyr Ala Val His
1               5

<210> SEQ ID NO 56
<211> LENGTH: 4
<212> TYPE: PRT
<213> ORGANISM: Artificial sequence
<220> FEATURE:
<223> OTHER INFORMATION: Synthetic construct

<400> SEQUENCE: 56

His Gly Met Ser
1

<210> SEQ ID NO 57
<211> LENGTH: 5
<212> TYPE: PRT
<213> ORGANISM: Artificial sequence
<220> FEATURE:
<223> OTHER INFORMATION: Synthetic construct

<400> SEQUENCE: 57

Ser Tyr Trp Met Asn
1               5

<210> SEQ ID NO 58
<211> LENGTH: 7
<212> TYPE: PRT
<213> ORGANISM: Artificial sequence
<220> FEATURE:
<223> OTHER INFORMATION: Synthetic construct

<400> SEQUENCE: 58

Thr Phe Gly Met Gly Val Gly
1               5

<210> SEQ ID NO 59
<211> LENGTH: 5
<212> TYPE: PRT
<213> ORGANISM: Artificial sequence
<220> FEATURE:
<223> OTHER INFORMATION: Synthetic construct

<400> SEQUENCE: 59

Asp Tyr Asn Met Asp
1               5

<210> SEQ ID NO 60
<211> LENGTH: 17
<212> TYPE: PRT
<213> ORGANISM: Artificial sequence
<220> FEATURE:
```

-continued

<223> OTHER INFORMATION: Synthetic construct

<400> SEQUENCE: 60

Thr Ile Ser Ser Ser Gly Ser Tyr Thr Tyr Tyr Pro Asp Ser Val Lys
1               5                   10                  15
Gly

<210> SEQ ID NO 61
<211> LENGTH: 17
<212> TYPE: PRT
<213> ORGANISM: Artificial sequence
<220> FEATURE:
<223> OTHER INFORMATION: Synthetic construct

<400> SEQUENCE: 61

Tyr Ser Asn Ser Asp Ser Thr Thr Ile Tyr Tyr Ala Asp Thr Val Lys
1               5                   10                  15
Gly

<210> SEQ ID NO 62
<211> LENGTH: 17
<212> TYPE: PRT
<213> ORGANISM: Artificial sequence
<220> FEATURE:
<223> OTHER INFORMATION: Synthetic construct

<400> SEQUENCE: 62

Glu Ile Asn Pro Asp Gly Asn Ala Ile Asn Tyr Ala Pro Ser Leu Lys
1               5                   10                  15
Asp

<210> SEQ ID NO 63
<211> LENGTH: 16
<212> TYPE: PRT
<213> ORGANISM: Artificial sequence
<220> FEATURE:
<223> OTHER INFORMATION: Synthetic construct

<400> SEQUENCE: 63

Met Ile Trp Gly Asp Gly Ser Thr Asp Tyr Asn Ser Ala Leu Lys Ser
1               5                   10                  15

<210> SEQ ID NO 64
<211> LENGTH: 17
<212> TYPE: PRT
<213> ORGANISM: Artificial sequence
<220> FEATURE:
<223> OTHER INFORMATION: Synthetic construct

<400> SEQUENCE: 64

Met Ile Asp Pro Ser Asp Ser Glu Thr Arg Leu Asn Gln Lys Phe Lys
1               5                   10                  15
Asp

<210> SEQ ID NO 65
<211> LENGTH: 17
<212> TYPE: PRT
<213> ORGANISM: Artificial sequence
<220> FEATURE:
<223> OTHER INFORMATION: Synthetic construct

<400> SEQUENCE: 65

Asp Ile Asp Pro Asn Asn Gly Asp Thr Phe Tyr Asn Gln Lys Phe Lys
1               5                   10                  15

<210> SEQ ID NO 66
<211> LENGTH: 16
<212> TYPE: PRT
<213> ORGANISM: Artificial sequence
<220> FEATURE:
<223> OTHER INFORMATION: Synthetic construct

<400> SEQUENCE: 66

Val Met Trp Ser Gly Gly Ser Thr Asp Tyr Asn Ala Ala Phe Ile Ser
1               5                   10                  15

<210> SEQ ID NO 67
<211> LENGTH: 14
<212> TYPE: PRT
<213> ORGANISM: Artificial sequence
<220> FEATURE:
<223> OTHER INFORMATION: Synthetic construct

<400> SEQUENCE: 67

Thr Tyr Ser Gly Val Pro Thr Tyr Thr Asp Asp Phe Lys Gly
1               5                   10

<210> SEQ ID NO 68
<211> LENGTH: 17
<212> TYPE: PRT
<213> ORGANISM: Artificial sequence
<220> FEATURE:
<223> OTHER INFORMATION: Synthetic construct

<400> SEQUENCE: 68

Gln Ile Tyr Pro Gly Asp Gly Asp Thr Asp Tyr Asn Gly Lys Phe Lys
1               5                   10                  15
Gly

<210> SEQ ID NO 69
<211> LENGTH: 16
<212> TYPE: PRT
<213> ORGANISM: Artificial sequence
<220> FEATURE:
<223> OTHER INFORMATION: Synthetic construct

<400> SEQUENCE: 69

His Ile Trp Trp Asp Asp Asp Lys Tyr Tyr Asn Pro Ala Leu Lys Ser
1               5                   10                  15

<210> SEQ ID NO 70
<211> LENGTH: 17
<212> TYPE: PRT
<213> ORGANISM: Artificial sequence
<220> FEATURE:
<223> OTHER INFORMATION: Synthetic construct

<400> SEQUENCE: 70

Asp Ile Asn Pro Asn Thr Gly Gly Thr Ile Tyr Asn Gln Lys Phe Lys
1               5                   10                  15
Gly

<210> SEQ ID NO 71
<211> LENGTH: 8
<212> TYPE: PRT
<213> ORGANISM: Artificial sequence
<220> FEATURE:
<223> OTHER INFORMATION: Synthetic construct

<400> SEQUENCE: 71

Thr Tyr Tyr Gly Ala Met Asp Tyr
1               5

<210> SEQ ID NO 72
<211> LENGTH: 9
<212> TYPE: PRT
<213> ORGANISM: Artificial sequence
<220> FEATURE:
<223> OTHER INFORMATION: Synthetic construct

<400> SEQUENCE: 72

Ser Tyr Tyr Ser Asn Tyr Val Asp Tyr
1               5

<210> SEQ ID NO 73
<211> LENGTH: 5
<212> TYPE: PRT
<213> ORGANISM: Artificial sequence
<220> FEATURE:
<223> OTHER INFORMATION: Synthetic construct

<400> SEQUENCE: 73

Pro Phe Pro Ser Val
1               5

<210> SEQ ID NO 74
<211> LENGTH: 5
<212> TYPE: PRT
<213> ORGANISM: Artificial sequence
<220> FEATURE:
<223> OTHER INFORMATION: Synthetic construct

<400> SEQUENCE: 74

Trp Ala Phe Ala Tyr
1               5

<210> SEQ ID NO 75
<211> LENGTH: 7
<212> TYPE: PRT
<213> ORGANISM: Artificial sequence
<220> FEATURE:
<223> OTHER INFORMATION: Synthetic construct

<400> SEQUENCE: 75

Pro Tyr Gly Asp Leu Asp Tyr
1               5

<210> SEQ ID NO 76
<211> LENGTH: 3
<212> TYPE: PRT
<213> ORGANISM: Artificial sequence
<220> FEATURE:
<223> OTHER INFORMATION: Synthetic construct

<400> SEQUENCE: 76

Asp Leu Tyr
1

<210> SEQ ID NO 77
<211> LENGTH: 12
<212> TYPE: PRT
<213> ORGANISM: Artificial sequence
<220> FEATURE:
<223> OTHER INFORMATION: Synthetic construct

```
<400> SEQUENCE: 77

Met Gly Asp Tyr Asp Gly Val Ala Trp Phe Ala Tyr
1               5                   10

<210> SEQ ID NO 78
<211> LENGTH: 8
<212> TYPE: PRT
<213> ORGANISM: Artificial sequence
<220> FEATURE:
<223> OTHER INFORMATION: Synthetic construct

<400> SEQUENCE: 78

Ser Glu Leu Ser Trp Phe Ala Tyr
1               5

<210> SEQ ID NO 79
<211> LENGTH: 4
<212> TYPE: PRT
<213> ORGANISM: Artificial sequence
<220> FEATURE:
<223> OTHER INFORMATION: Synthetic construct

<400> SEQUENCE: 79

Arg Ser Pro Tyr
1

<210> SEQ ID NO 80
<211> LENGTH: 8
<212> TYPE: PRT
<213> ORGANISM: Artificial sequence
<220> FEATURE:
<223> OTHER INFORMATION: Synthetic construct

<400> SEQUENCE: 80

Arg Gly Ser Asn Ala Leu Asp Tyr
1               5

<210> SEQ ID NO 81
<211> LENGTH: 14
<212> TYPE: PRT
<213> ORGANISM: Artificial sequence
<220> FEATURE:
<223> OTHER INFORMATION: Synthetic construct

<400> SEQUENCE: 81

Glu Gly Pro Tyr Tyr Tyr Gly Thr Thr His Pro Phe Ala Tyr
1               5                   10

<210> SEQ ID NO 82
<211> LENGTH: 16
<212> TYPE: PRT
<213> ORGANISM: Artificial sequence
<220> FEATURE:
<223> OTHER INFORMATION: Synthetic construct

<400> SEQUENCE: 82

Arg Ser Ser Gln Thr Ile Val His Ser Asn Gly Asn Thr Tyr Leu Glu
1               5                   10                  15

<210> SEQ ID NO 83
<211> LENGTH: 16
<212> TYPE: PRT
<213> ORGANISM: Artificial sequence
<220> FEATURE:
<223> OTHER INFORMATION: Synthetic construct

<400> SEQUENCE: 83
```

Arg Ser Ser Gln Ser Leu Val His Ser Asn Gly Asn Thr Tyr Leu His
1               5                   10                  15

<210> SEQ ID NO 84
<211> LENGTH: 16
<212> TYPE: PRT
<213> ORGANISM: Artificial sequence
<220> FEATURE:
<223> OTHER INFORMATION: Synthetic construct

<400> SEQUENCE: 84

Arg Ser Ser Gln Ser Leu Val Arg Ser Asn Gly Asn Thr Tyr Leu Glu
1               5                   10                  15

<210> SEQ ID NO 85
<211> LENGTH: 16
<212> TYPE: PRT
<213> ORGANISM: Artificial sequence
<220> FEATURE:
<223> OTHER INFORMATION: Synthetic construct

<400> SEQUENCE: 85

Lys Ser Ser Gln Ser Leu Leu Asp Ser Gly Gly Lys Thr Tyr Leu Asn
1               5                   10                  15

<210> SEQ ID NO 86
<211> LENGTH: 16
<212> TYPE: PRT
<213> ORGANISM: Artificial sequence
<220> FEATURE:
<223> OTHER INFORMATION: Synthetic construct

<400> SEQUENCE: 86

Lys Ser Ser Gln Ser Leu Leu Asp Ser Asp Gly Lys Thr Tyr Leu Asn
1               5                   10                  15

<210> SEQ ID NO 87
<211> LENGTH: 16
<212> TYPE: PRT
<213> ORGANISM: Artificial sequence
<220> FEATURE:
<223> OTHER INFORMATION: Synthetic construct

<400> SEQUENCE: 87

Lys Ser Ser Gln Ser Leu Leu Tyr Ser Asn Gly Lys Thr Tyr Leu Asn
1               5                   10                  15

<210> SEQ ID NO 88
<211> LENGTH: 11
<212> TYPE: PRT
<213> ORGANISM: Artificial sequence
<220> FEATURE:
<223> OTHER INFORMATION: Synthetic construct

<400> SEQUENCE: 88

Arg Ala Ser Gln Ser Ile Ser Asp Tyr Leu His
1               5                   10

<210> SEQ ID NO 89
<211> LENGTH: 16
<212> TYPE: PRT
<213> ORGANISM: Artificial sequence
<220> FEATURE:
<223> OTHER INFORMATION: Synthetic construct

<400> SEQUENCE: 89

Arg Ser Ser Gln Ser Ile Val His Ser Asn Gly Asn Thr Tyr Leu Glu
1               5                   10                  15

<210> SEQ ID NO 90
<211> LENGTH: 16
<212> TYPE: PRT
<213> ORGANISM: Artificial sequence
<220> FEATURE:
<223> OTHER INFORMATION: Synthetic construct

<400> SEQUENCE: 90

Arg Ser Ser Gln Ser Leu Ala Asn Ser Tyr Gly Asn Thr Tyr Leu Ser
1               5                   10                  15

<210> SEQ ID NO 91
<211> LENGTH: 7
<212> TYPE: PRT
<213> ORGANISM: Artificial sequence
<220> FEATURE:
<223> OTHER INFORMATION: Synthetic construct

<400> SEQUENCE: 91

Lys Val Ser Asn Arg Phe Ser
1               5

<210> SEQ ID NO 92
<211> LENGTH: 11
<212> TYPE: PRT
<213> ORGANISM: Artificial sequence
<220> FEATURE:
<223> OTHER INFORMATION: Synthetic construct

<400> SEQUENCE: 92

Gln Val Ser Lys Leu Asp Ser Gly Val Pro Asp
1               5                   10

<210> SEQ ID NO 93
<211> LENGTH: 7
<212> TYPE: PRT
<213> ORGANISM: Artificial sequence
<220> FEATURE:
<223> OTHER INFORMATION: Synthetic construct

<400> SEQUENCE: 93

Leu Val Ser Lys Leu Asp Ser
1               5

<210> SEQ ID NO 94
<211> LENGTH: 7
<212> TYPE: PRT
<213> ORGANISM: Artificial sequence
<220> FEATURE:
<223> OTHER INFORMATION: Synthetic construct

<400> SEQUENCE: 94

Tyr Ala Ser Gln Ser Ile Ser
1               5

<210> SEQ ID NO 95
<211> LENGTH: 7
<212> TYPE: PRT
<213> ORGANISM: Artificial sequence
<220> FEATURE:
<223> OTHER INFORMATION: Synthetic construct

<400> SEQUENCE: 95

Gly Ile Ser Asn Arg Phe Ser 1               5

<210> SEQ ID NO 96
<211> LENGTH: 9
<212> TYPE: PRT
<213> ORGANISM: Artificial sequence
<220> FEATURE:
<223> OTHER INFORMATION: Synthetic construct

<400> SEQUENCE: 96

Phe Gln Gly Ser Leu Val Pro Trp Thr
1               5

<210> SEQ ID NO 97
<211> LENGTH: 9
<212> TYPE: PRT
<213> ORGANISM: Artificial sequence
<220> FEATURE:
<223> OTHER INFORMATION: Synthetic construct

<400> SEQUENCE: 97

Phe Gln Ser Thr His Val Pro Pro Thr
1               5

<210> SEQ ID NO 98
<211> LENGTH: 9
<212> TYPE: PRT
<213> ORGANISM: Artificial sequence
<220> FEATURE:
<223> OTHER INFORMATION: Synthetic construct

<400> SEQUENCE: 98

Phe Gln Gly Ser His Val Pro Tyr Thr
1               5

<210> SEQ ID NO 99
<211> LENGTH: 9
<212> TYPE: PRT
<213> ORGANISM: Artificial sequence
<220> FEATURE:
<223> OTHER INFORMATION: Synthetic construct

<400> SEQUENCE: 99

Trp Gln Gly Thr His Phe Pro Leu Thr
1               5

<210> SEQ ID NO 100
<211> LENGTH: 9
<212> TYPE: PRT
<213> ORGANISM: Artificial sequence
<220> FEATURE:
<223> OTHER INFORMATION: Synthetic construct

<400> SEQUENCE: 100

Trp Gln Gly Thr His Phe Pro Phe Thr
1               5

<210> SEQ ID NO 101
<211> LENGTH: 9
<212> TYPE: PRT
<213> ORGANISM: Artificial sequence
<220> FEATURE:
<223> OTHER INFORMATION: Synthetic construct

<400> SEQUENCE: 101

Val Gln Gly Thr His Phe Pro His Thr
1               5

```
<210> SEQ ID NO 102
<211> LENGTH: 10
<212> TYPE: PRT
<213> ORGANISM: Artificial sequence
<220> FEATURE:
<223> OTHER INFORMATION: Synthetic construct

<400> SEQUENCE: 102

Ser Gln Ser Thr His Val Pro Pro Trp Thr
1               5                   10

<210> SEQ ID NO 103
<211> LENGTH: 9
<212> TYPE: PRT
<213> ORGANISM: Artificial sequence
<220> FEATURE:
<223> OTHER INFORMATION: Synthetic construct

<400> SEQUENCE: 103

Gln Asn Gly His Ser Phe Pro Tyr Thr
1               5

<210> SEQ ID NO 104
<211> LENGTH: 9
<212> TYPE: PRT
<213> ORGANISM: Artificial sequence
<220> FEATURE:
<223> OTHER INFORMATION: Synthetic construct

<400> SEQUENCE: 104

Leu Gln Gly Thr His Gln Pro Trp Thr
1               5

<210> SEQ ID NO 105
<211> LENGTH: 9
<212> TYPE: PRT
<213> ORGANISM: Artificial sequence
<220> FEATURE:
<223> OTHER INFORMATION: Synthetic construct

<400> SEQUENCE: 105

Val Gln Gly Thr His Phe Pro Gln Thr
1               5

<210> SEQ ID NO 106
<211> LENGTH: 123
<212> TYPE: PRT
<213> ORGANISM: Artificial sequence
<220> FEATURE:
<223> OTHER INFORMATION: Synthetic construct

<400> SEQUENCE: 106

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala His Gly Gln Gly Leu Glu Trp Ile
        35                  40                  45

Gly Asp Ile Asn Pro Asn Thr Gly Gly Thr Ile Tyr Asn Gln Lys Phe
    50                  55                  60

Lys Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
```

```
                    85                  90                  95
Ala Gly Glu Gly Pro Tyr Tyr Tyr Gly Thr Thr His Pro Phe Ala Tyr
                100                 105                 110

Trp Gly Gln Gly Thr Leu Val Thr Val Ser Ser
        115                 120

<210> SEQ ID NO 107
<211> LENGTH: 112
<212> TYPE: PRT
<213> ORGANISM: Artificial sequence
<220> FEATURE:
<223> OTHER INFORMATION: Synthetic construct

<400> SEQUENCE: 107

Asp Val Val Met Thr Gln Ser Pro Leu Ser Leu Pro Val Thr Leu Gly
1               5                   10                  15

Gln Pro Ala Ser Ile Ser Cys Lys Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Gln Thr Phe Gly Gly Gly Thr Lys Leu Glu Ile Lys
            100                 105                 110

<210> SEQ ID NO 108
<211> LENGTH: 369
<212> TYPE: DNA
<213> ORGANISM: Artificial sequence
<220> FEATURE:
<223> OTHER INFORMATION: Synthetic construct

<400> SEQUENCE: 108
caagtgcagc tggtccagag cggcgccgag gtgaaaaagc ccggcgccag cgtgaaggtg      60
tcttgtaaag cctctggcta caccttcacc gactacaaca tggactgggt gcggcaggcc    120
cacggccagg gcctggaatg gatcggcgac atcaaccca  caccggcgg aacaatctac    180 aaccagaagt tcaagggcag agccaccctg acagtggaca ccagcatcag caccgcctac    240
atggaactga gcagactgag aagcgacgac acagccgtgt actactgcgc cggcgagggc    300
ccttactact acggcacgac ccacccttc  gcctactggg gccagggcac actggtgacc    360
gtgtccagc                                                            369

<210> SEQ ID NO 109
<211> LENGTH: 336
<212> TYPE: DNA
<213> ORGANISM: Artificial sequence
<220> FEATURE:
<223> OTHER INFORMATION: Synthetic construct

<400> SEQUENCE: 109
gatgtggtga tgacccagtc tccactgagc ctgcctgtga ccctgggcca acctgccagc     60
atcagctgta aaagcagcca gagcctgctg tacagcaacg gcaagaccta cctgaactgg    120
ctgctgcaga gacctggcca gagccctaga cggctgatct acctggtgtc caagctggac    180
```

```
agcggcgtcc ccgatagatt cagcggatct ggcagcggca ccgacttcac cctgaagatc      240
agtagagtgg aagccgagga cgtgggcgtg tactactgcg tgcagggcac acacttcccc      300
cagaccttcg gcggcggaac aaagctggaa atcaag                                336
```

ANTIBODIES THAT BIND TO PATHOLOGICAL TAU SPECIES AND USES THEREOF

CROSS-REFERENCES TO RELATED APPLICATIONS

This application is a continuation-in-part of International Application No. PCT/IB2020/057415, filed Aug. 5, 2020, which claims priority to U.S. Provisional Application No. 62/883,605, filed Aug. 6, 2019, each of which is incorporated herein by reference in its entirety.

SEQUENCE LISTING

This application contains a Sequence Listing in computer readable form as a ASCII text file named 056239_501001WO_ST25.txt; which is 55,716 bytes in size, created Aug. 1, 2020, and electronically submitted via ePCT herewith the application. The Sequence Listing is incorporated herein by reference in its entirety and forms part of the disclosure.

FIELD

The present disclosure generally relates to antibodies that bind pathological Tau species, including compositions and methods relating to the antibodies, such as for treating neurodegenerative diseases associated with pathological aggregation of Tau.

BACKGROUND

Neurodegenerative diseases affect an estimated 50 million Americans each year, exacting an incalculable personal toll and an annual economic cost of hundreds of billions of dollars in medical expenses and lost productivity. Tauopathies are a class of neurodegenerative diseases associated with pathological aggregation of Tau protein in the human brain, and include Alzheimer's disease (AD), progressive supranuclear palsy (PSP), Pick's Disease (PiD), and corticobasal degeneration (CBD). In tauopathy, aggregation of Tau spreads through the brain in a prion-like manner, such as seen in AD brain (Braak, H., & Braak, E. V. A. (1995). *Neurobiology of aging*, 16(3), 271-278; Braak, H., et al. (2006). *Acta neuropathologica*, 112(4), 389-404), where Tau pathology manifests in a consistent spatiotemporal pattern.

Tau is normally a highly soluble cytoplasmic protein, but in Alzheimer's disease, Tau is abnormally phosphorylated and accumulates at synapses to exert synaptotoxicity. Tau propagation seeds, consisting mainly of short fibrils, have been found to be significantly enriched in the synaptic fractions of brain regions lacking extensive cellular Tau pathology, indicating that Tau seeds are able to spread through the human brain along synaptically-connected neuronal networks.

Despite many therapeutic approaches aimed at removing aggregated Tau species that have been or are currently being investigated, at present there are no effective treatments for halting, preventing, or reversing the progression of such neurodegenerative diseases. Therefore, there is an urgent need for pharmaceutical agents capable of slowing the progression of these neurodegenerative diseases and/or preventing them from developing.

SUMMARY

This section provides a general summary of the disclosure, and is not comprehensive of its full scope or all of its features. The present application provides anti-Tau antibodies or antigen-binding moieties thereof (e.g., an isolated anti-Tau antibody or antigen-binding moiety thereof). Without being bound to theory, in some embodiments, the anti-Tau antibodies or antigen-binding moieties thereof are capable of binding selectively to Tau aggregates that are more abundant in human tauopathy disorders. In some embodiments, the anti-Tau antibodies or antigen-binding moieties thereof are capable of inhibiting Tau seeding and/or Tau aggregation, thus preventing the initiation and/or spreading of such human tauopathies.

In one aspect, provided herein is an anti-Tau antibody or antigen-binding moiety thereof (e.g., an isolated anti-Tau antibody or antigen-binding moiety thereof) comprising: a) a heavy chain variable region comprising i) a complementary determining region (CDR) 1 comprising the amino acid sequence of any one of SEQ ID NOs: 49-59 or a variant thereof having at least 80%, at least 90%, or at least 95% sequence identity to the amino acid sequence of any one of SEQ ID NOs: 49-59; ii) a CDR2 comprising the amino acid sequence of any one of SEQ ID NOs: 60-70 or a variant thereof having at least 80%, at least 90%, or at least 95% sequence identity to the amino acid sequence of any one of SEQ ID NOs: 60-70; and/or iii) a CDR3 comprising the amino acid sequence of any one of SEQ ID NOs: 71-81 or a variant thereof having at least 80%, at least 90%, or at least 95% sequence identity to the amino acid sequence of any one of SEQ ID NOs: 71-81; and/or b) a light chain variable region comprising iv) a CDR1 comprising the amino acid sequence of any one of SEQ ID NOs: 82-90 or a variant thereof having at least 80%, at least 90%, or at least 95% sequence identity to the amino acid sequence of any one of SEQ ID NOs: 82-90; v) a CDR2 comprising the amino acid sequence of any one of SEQ ID NOs: 91-95 or a variant thereof having at least 80%, at least 90%, or at least 95% sequence identity to the amino acid sequence of any one of SEQ ID NOs: 91-95; and/or vi) a CDR3 comprising the amino acid sequence of any one of SEQ ID NOs: 96-105 or a variant thereof having at least 80%, at least 90%, or at least 95% sequence identity to the amino acid sequence of any one of SEQ ID NOS: 96-105.

In some embodiments, according to any of the anti-Tau antibodies or antigen-binding moieties described above, 1) the heavy chain variable region CDR1, CDR2, and CDR3 comprise the amino acid sequences of SEQ ID NOs: 50, 61, and 72, respectively, or variants thereof having at least 80%, at least 90%, or at least 95% sequence identity to the amino acid sequences of SEQ ID NOs: 50, 61, and 72, respectively; and the light chain variable region CDR1, CDR2, and CDR3 comprise the amino acid sequences of SEQ ID NOs: 83, 91, and 97, respectively, or variants thereof having at least 80%, at least 90%, or at least 95% sequence identity to the amino acid sequences of SEQ ID NOs: 83, 91, and 97, respectively; 2) the heavy chain variable region CDR1, CDR2, and CDR3 comprise the amino acid sequences of SEQ ID NOs: 49, 60, and 71, respectively, or variants thereof having at least 80%, at least 90%, or at least 95% sequence identity to the amino acid sequences of SEQ ID NOs: 49, 60, and 71, respectively; and the light chain variable region CDR1, CDR2, and CDR3 comprise the amino acid sequences of SEQ ID NOs: 82, 91, and 96, respectively, or variants thereof having at least 80%, at least 90%, or at least 95% sequence identity to the amino acid sequences of SEQ ID NOs: 82, 91, and 96, respectively; 3) the heavy chain variable region CDR1, CDR2, and CDR3 comprise the amino acid sequences of SEQ ID NOs: 51, 62, and 73, respectively, or variants thereof having at least 80%, at least 90%, or at least 95% sequence identity to the amino acid sequences of SEQ ID NOs: 51, 62, and 73, respectively; and the light chain variable region CDR1, CDR2, and CDR3 comprise the amino acid sequences of SEQ ID NOs: 84, 91, and 98, respectively, or variants thereof having at least 80%, at least 90%, or at least 95% sequence identity to the amino acid sequences of SEQ ID NOs: 84, 91, and 98, respectively; 4) the heavy chain variable region CDR1, CDR2, and CDR3 comprise the amino acid sequences of SEQ ID NOs: 52, 63, and 74, respectively, or variants thereof having at least 80%, at least 90%, or at least 95% sequence identity to the amino acid sequences of SEQ ID NOs: 52, 63, and 74, respectively; and the light chain variable region CDR1, CDR2, and CDR3 comprise the amino acid sequences of SEQ ID NOs: 85, 92, and 99, respectively, respectively, or variants thereof having at least 80%, at least 90%, or at least 95% sequence identity to the amino acid sequences of SEQ ID NOs: 85, 92, and 99, respectively; 5) the heavy chain variable region CDR1, CDR2, and CDR3 comprise the amino acid sequences of SEQ ID NOs: 53, 64, and 75, respectively, or variants thereof having at least 80%, at least 90%, or at least 95% sequence identity to the amino acid sequences of SEQ ID NOs: 53, 64, and 75, respectively; and the light chain variable region CDR1, CDR2, and CDR3 comprise the amino acid sequences of SEQ ID NOs: 86, 93, and 100, respectively, or variants thereof having at least 80%, at least 90%, or at least 95% sequence identity to the amino acid sequences of SEQ ID NOs: 86, 93, and 100, respectively; 6) the heavy chain variable region CDR1, CDR2, and CDR3 comprise the amino acid sequences of SEQ ID NOs: 54, 65, and 76, respectively, or variants thereof having at least 80%, at least 90%, or at least 95% sequence identity to the amino acid sequences of SEQ ID NOs: 54, 65, and 76, respectively; and the light chain variable region CDR1, CDR2, and CDR3 comprise the amino acid sequences of SEQ ID NOs: 87, 93, and 101, respectively, or variants thereof having at least 80%, at least 90%, or at least 95% sequence identity to the amino acid sequences of SEQ ID NOs: 87, 93, and 101, respectively; 7) the heavy chain variable region CDR1, CDR2, and CDR3 comprise the amino acid sequences of SEQ ID NOs: 55, 66, and 77, respectively, or variants thereof having at least 80%, at least 90%, or at least 95% sequence identity to the amino acid sequences of SEQ ID NOs: 55, 66, and 77, respectively; and the light chain variable region CDR1, CDR2, and CDR3 comprise the amino acid sequences of SEQ ID NOs: 83, 91, and 102, respectively, or variants thereof having at least 80%, at least 90%, or at least 95% sequence identity to the amino acid sequences of SEQ ID NOs: 83, 91, and 102, respectively; 8) the heavy chain variable region CDR1, CDR2, and CDR3 comprise the amino acid sequences of SEQ ID NOs: 56, 67, and 78, respectively, or variants thereof having at least 80%, at least 90%, or at least 95% sequence identity to the amino acid sequences of SEQ ID NOs: 56, 67, and 78, respectively; and the light chain variable region CDR1, CDR2, and CDR3 comprise the amino acid sequences of SEQ ID NOs: 88, 94, and 103, respectively, or variants thereof having at least 80%, at least 90%, or at least 95% sequence identity to the amino acid sequences of SEQ ID NOs: 88, 94, and 103, respectively; 9) the heavy chain variable region CDR1, CDR2, and CDR3 comprise the amino acid sequences of SEQ ID NOs: 57, 68, and 79, respectively, or variants thereof having at least 80%, at least 90%, or at least 95% sequence identity to the amino acid sequences of SEQ ID NOs: 57, 68, and 79, respectively; and the light chain variable region CDR1, CDR2, and CDR3 comprise the amino acid sequences of SEQ ID NOs: 89, 91, and 98, respectively, or variants thereof having at least 80%, at least 90%, or at least 95% sequence identity to the amino acid sequences of SEQ ID NOs: 89, 91, and 98, respectively; 10) the heavy chain variable region CDR1, CDR2, and CDR3 comprise the amino acid sequences of SEQ ID NOs: 58, 69, and 80, respectively, or variants thereof having at least 80%, at least 90%, or at least 95% sequence identity to the amino acid sequences of SEQ ID NOs: 58, 69, and 80, respectively; and the light chain variable region CDR1, CDR2, and CDR3 comprise the amino acid sequences of SEQ ID NOs: 90, 95, and 104, respectively, or variants thereof having at least 80%, at least 90%, or at least 95% sequence identity to the amino acid sequences of SEQ ID NOs: 90, 95, and 104, respectively; or 11) the heavy chain variable region CDR1, CDR2, and CDR3 comprise the amino acid sequences of SEQ ID NOs: 59, 70, and 81, respectively, or variants thereof having at least 80%, at least 90%, or at least 95% sequence identity to the amino acid sequences of SEQ ID NOs: 59, 70, and 81, respectively; and the light chain variable region CDR1, CDR2, and CDR3 comprise the amino acid sequences of SEQ ID NOs: 87, 93, and 105, respectively, or variants thereof having at least 80%, at least 90%, or at least 95% sequence identity to the amino acid sequences of SEQ ID NOs: 87, 93, and 105, respectively.

In some embodiments, according to any of the anti-Tau antibodies or antigen-binding moieties described above, the heavy chain variable region CDR1, CDR2, and CDR3 comprise the amino acid sequences of SEQ ID NOs: 50, 61, and 72, respectively, or variants thereof having at least 80%, at least 90%, or at least 95% sequence identity to the amino acid sequences of SEQ ID NOs: 50, 61, and 72, respectively; and the light chain variable region CDR1, CDR2, and CDR3 comprise the amino acid sequences of SEQ ID NOs: 83, 91, and 97, respectively, or variants thereof having at least 80%, at least 90%, or at least 95% sequence identity to the amino acid sequences of SEQ ID NOs: 83, 91, and 97, respectively.

In some embodiments, according to any of the anti-Tau antibodies or antigen-binding moieties described above, the heavy chain variable region CDR1, CDR2, and CDR3 comprise the amino acid sequences of SEQ ID NOs: 50, 61, and 72, respectively; and the light chain variable region CDR1, CDR2, and CDR3 comprise the amino acid sequences of SEQ ID NOs: 83, 91, and 97, respectively.

In some embodiments, according to any of the anti-Tau antibodies or antigen-binding moieties described above, the heavy chain variable region CDR1, CDR2, and CDR3 comprise the amino acid sequences of SEQ ID NOs: 59, 70, and 81, respectively, or variants thereof having at least 80%, at least 90%, or at least 95% sequence identity to the amino acid sequences of SEQ ID NOs: 59, 70, and 81, respectively; and the light chain variable region CDR1, CDR2, and CDR3 comprise the amino acid sequences of SEQ ID NOs: 87, 93, and 105, respectively, or variants thereof having at least 80%, at least 90%, or at least 95% sequence identity to the amino acid sequences of SEQ ID NOs: 87, 93, and 105, respectively.

In some embodiments, according to any of the anti-Tau antibodies or antigen-binding moieties described above, the heavy chain variable region CDR1, CDR2, and CDR3 comprise the amino acid sequences of SEQ ID NOs: 59, 70, and 81, respectively; and the light chain variable region CDR1, CDR2, and CDR3 comprise the amino acid sequences of SEQ ID NOs: 87, 93, and 105, respectively.

In some embodiments, according to any of the anti-Tau antibodies or antigen-binding moieties described above, the heavy chain variable region comprises the amino acid sequence of any one of SEQ ID NOs: 1-12 and 106 or a variant thereof having at least 80%, at least 90%, at least 95%, at least 96%, at least 97%, at least 98%, or at least 99% sequence identity to the amino acid sequence of any one of SEQ ID NOs: 1-12 and 106; and/or the light chain variable region comprises the amino acid sequence of any one of SEQ ID NOs: 13-24 and 107 or a variant thereof having at least 80%, at least 90%, at least 95%, at least 96%, at least 97%, at least 98%, or at least 99% sequence identity to the amino acid sequence of any one of SEQ ID NOs: 13-24 and 107.

In some embodiments, according to any of the anti-Tau antibodies or antigen-binding moieties described above, 1) the heavy chain variable region comprises the amino acid sequence of SEQ ID NO: 3 or a variant thereof having at least 80%, at least 90%, at least 95%, at least 96%, at least 97%, at least 98%, or at least 99% sequence identity to the amino acid sequence of SEQ ID NO: 3; and the light chain variable region comprises the amino acid sequence of SEQ ID NO: 15 or a variant thereof having at least 80%, at least 90%, at least 95%, at least 96%, at least 97%, at least 98%, or at least 99% sequence identity to the amino acid sequence of SEQ ID NOs: 15; 2) the heavy chain variable region comprises the amino acid sequence of SEQ ID NO: 2 or a variant thereof having at least 80%, at least 90%, at least 95%, at least 96%, at least 97%, at least 98%, or at least 99% sequence identity to the amino acid sequence of SEQ ID NO: 2; and the light chain variable region comprises the amino acid sequence of SEQ ID NO: 14 or a variant thereof having at least 80%, at least 90%, at least 95%, at least 96%, at least 97%, at least 98%, or at least 99% sequence identity to the amino acid sequence of SEQ ID NOs: 14; 3) the heavy chain variable region comprises the amino acid sequence of SEQ ID NO: 1 or a variant thereof having at least 80%, at least 90%, at least 95%, at least 96%, at least 97%, at least 98%, or at least 99% sequence identity to the amino acid sequence of SEQ ID NO: 1; and the light chain variable region comprises the amino acid sequence of SEQ ID NO: 13 or a variant thereof having at least 80%, at least 90%, at least 95%, at least 96%, at least 97%, at least 98%, or at least 99% sequence identity to the amino acid sequence of SEQ ID NOs: 13; 4) the heavy chain variable region comprises the amino acid sequence of SEQ ID NO: 4 or a variant thereof having at least 80%, at least 90%, at least 95%, at least 96%, at least 97%, at least 98%, or at least 99% sequence identity to the amino acid sequence of SEQ ID NO: 4; and the light chain variable region comprises the amino acid sequence of SEQ ID NO: 16 or a variant thereof having at least 80%, at least 90%, at least 95%, at least 96%, at least 97%, at least 98%, or at least 99% sequence identity to the amino acid sequence of SEQ ID NOs: 16; 5) the heavy chain variable region comprises the amino acid sequence of SEQ ID NO: 5 or a variant thereof having at least 80%, at least 90%, at least 95%, at least 96%, at least 97%, at least 98%, or at least 99% sequence identity to the amino acid sequence of SEQ ID NO: 5; and the light chain variable region comprises the amino acid sequence of SEQ ID NO: 17 or a variant thereof having at least 80%, at least 90%, at least 95%, at least 96%, at least 97%, at least 98%, or at least 99% sequence identity to the amino acid sequence of SEQ ID NOs: 17; 6) the heavy chain variable region comprises the amino acid sequence of SEQ ID NO: 6 or a variant thereof having at least 80%, at least 90%, at least 95%, at least 96%, at least 97%, at least 98%, or at least 99% sequence identity to the amino acid sequence of SEQ ID NO: 6; and the light chain variable region comprises the amino acid sequence of SEQ ID NO: 18 or a variant thereof having at least 80%, at least 90%, at least 95%, at least 96%, at least 97%, at least 98%, or at least 99% sequence identity to the amino acid sequence of SEQ ID NOs: 18; 7) the heavy chain variable region comprises the amino acid sequence of SEQ ID NO: 7 or a variant thereof having at least 80%, at least 90%, at least 95%, at least 96%, at least 97%, at least 98%, or at least 99% sequence identity to the amino acid sequence of SEQ ID NO: 7; and the light chain variable region comprises the amino acid sequence of SEQ ID NO: 19 or a variant thereof having at least 80%, at least 90%, at least 95%, at least 96%, at least 97%, at least 98%, or at least 99% sequence identity to the amino acid sequence of SEQ ID NOs: 19; 8) the heavy chain variable region comprises the amino acid sequence of SEQ ID NO: 8 or a variant thereof having at least 80%, at least 90%, at least 95%, at least 96%, at least 97%, at least 98%, or at least 99% sequence identity to the amino acid sequence of SEQ ID NO: 8; and the light chain variable region comprises the amino acid sequence of SEQ ID NO: 20 or a variant thereof having at least 80%, at least 90%, at least 95%, at least 96%, at least 97%, at least 98%, or at least 99% sequence identity to the amino acid sequence of SEQ ID NOs: 20; 9) the heavy chain variable region comprises the amino acid sequence of SEQ ID NO: 9 or a variant thereof having at least 80%, at least 90%, at least 95%, at least 96%, at least 97%, at least 98%, or at least 99% sequence identity to the amino acid sequence of SEQ ID NO: 9; and the light chain variable region comprises the amino acid sequence of SEQ ID NO: 21 or a variant thereof having at least 80%, at least 90%, at least 95%, at least 96%, at least 97%, at least 98%, or at least 99% sequence identity to the amino acid sequence of SEQ ID NOs: 21; 10) the heavy chain variable region comprises the amino acid sequence of SEQ ID NO: 10 or a variant thereof having at least 80%, at least 90%, at least 95%, at least 96%, at least 97%, at least 98%, or at least 99% sequence identity to the amino acid sequence of SEQ ID NO: 10; and the light chain variable region comprises the amino acid sequence of SEQ ID NO: 22 or a variant thereof having at least 80%, at least 90%, at least 95%, at least 96%, at least 97%, at least 98%, or at least 99% sequence identity to the amino acid sequence of SEQ ID NOs: 22; 11) the heavy chain variable region comprises the amino acid sequence of SEQ ID NO: 11 or a variant thereof having at least 80%, at least 90%, at least 95%, at least 96%, at least 97%, at least 98%, or at least 99% sequence identity to the amino acid sequence of SEQ ID NO: 11; and the light chain variable region comprises the amino acid sequence of SEQ ID NO: 23 or a variant thereof having at least 80%, at least 90%, at least 95%, at least 96%, at least 97%, at least 98%, or at least 99% sequence identity to the amino acid sequence of SEQ ID NOs: 23; 12) the heavy chain variable region comprises the amino acid sequence of SEQ ID NO: 12 or a variant thereof having at least 80%, at least 90%, at least 95%, at least 96%, at least 97%, at least 98%, or at least 99% sequence identity to the amino acid sequence of SEQ ID NO: 12; and the light chain variable region comprises the amino acid sequence of SEQ ID NO: 24 or a variant thereof having at least 80%, at least 90%, at least 95%, at least 96%, at least 97%, at least 98%, or at least 99% sequence identity to the amino acid sequence of SEQ ID NOs: 24; or 13) the heavy chain variable region comprises the amino acid sequence of SEQ ID NO: 106 or a variant thereof having at least 80%, at least 90%, at least 95%, at least 96%, at least 97%, at least 98%, or at least 99% sequence identity to the amino acid sequence of SEQ ID NO: 106; and the light chain variable region comprises the amino acid sequence of SEQ ID NO: 107 or a variant thereof having at least 80%, at least 90%, at least 95%, at least 96%, at least 97%, at least 98%, or at least 99% sequence identity to the amino acid sequence of SEQ ID NOs: 107.

In some embodiments, according to any of the anti-Tau antibodies or antigen-binding moieties described above, the heavy chain variable region comprises the amino acid sequence of SEQ ID NO: 3 or a variant thereof having at least 80%, at least 90%, at least 95%, at least 96%, at least 97%, at least 98%, or at least 99% sequence identity to the amino acid sequence of SEQ ID NO: 3; and the light chain variable region comprises the amino acid sequence of SEQ ID NO: 15 or a variant thereof having at least 80%, at least 90%, at least 95%, at least 96%, at least 97%, at least 98%, or at least 99% sequence identity to the amino acid sequence of SEQ ID NO: 15.

In some embodiments, according to any of the anti-Tau antibodies or antigen-binding moieties described above, the heavy chain variable region comprises the amino acid sequence of SEQ ID NO: 3; and the light chain variable region comprises the amino acid sequence of SEQ ID NO: 15.

In some embodiments, according to any of the anti-Tau antibodies or antigen-binding moieties described above, the heavy chain variable region comprises the amino acid sequence of SEQ ID NO: 106 or a variant thereof having at least 80%, at least 90%, at least 95%, at least 96%, at least 97%, at least 98%, or at least 99% sequence identity to the amino acid sequence of SEQ ID NO: 106; and the light chain variable region comprises the amino acid sequence of SEQ ID NO: 107 or a variant thereof having at least 80%, at least 90%, at least 95%, at least 96%, at least 97%, at least 98%, or at least 99% sequence identity to the amino acid sequence of SEQ ID NO: 107.

In some embodiments, according to any of the anti-Tau antibodies or antigen-binding moieties described above, the heavy chain variable region comprises the amino acid sequence of SEQ ID NO: 106; and the light chain variable region comprises the amino acid sequence of SEQ ID NO: 107.

In some embodiments, the anti-Tau antibody or antigen-binding moiety binds at least one, at least two, at least three, at least four, or at least five of amino acid residues S131, K132, T135, S137 and R155 of human 2N4R Tau isoform. In some embodiments, the anti-Tau antibody or antigen-binding moiety binds to an epitope comprising S131 of human 2N4R Tau isoform. In some embodiments, the anti-Tau antibody or antigen-binding moiety binds to an epitope comprising K132 of human 2N4R Tau isoform. In some embodiments, the anti-Tau antibody or antigen-binding moiety binds to an epitope comprising T135 of human 2N4R Tau isoform. In some embodiments, the anti-Tau antibody or antigen-binding moiety binds to an epitope comprising S137 of human 2N4R Tau isoform. In some embodiments, the anti-Tau antibody or antigen-binding moiety binds to an epitope comprising R155 of human 2N4R Tau isoform.

In some embodiments, the anti-Tau antibody or antigen-binding moiety binds to at least one, at least two, at least three, at least four, at least five, or at least six of amino acid residues R230, T231, S237, T245, K281 and S289 of human 2N4R Tau isoform. In some embodiments, the anti-Tau antibody or antigen-binding moiety binds to an epitope comprising R230 of human 2N4R Tau isoform. In some embodiments, the anti-Tau antibody or antigen-binding moiety binds to an epitope comprising T231 of human 2N4R Tau isoform. In some embodiments, the anti-Tau antibody or antigen-binding moiety binds to an epitope comprising S237 of human 2N4R Tau isoform. In some embodiments, the anti-Tau antibody or antigen-binding moiety binds to an epitope comprising T245 of human 2N4R Tau isoform. In some embodiments, the anti-Tau antibody or antigen-binding moiety binds to an epitope comprising K281 of human 2N4R Tau isoform. In some embodiments, the anti-Tau antibody or antigen-binding moiety binds to an epitope comprising S289 of human 2N4R Tau isoform.

In some embodiments, the anti-Tau antibody or antigen-binding moiety comprises a heavy chain variable region comprising CDR1, CDR2, and CDR3 comprised in the amino acid sequence of SEQ ID NO: 3; and a light chain variable region comprising CDR1, CDR2, and CDR3 comprised in the amino acid sequence of SEQ ID NO: 15.

In some embodiments, the anti-Tau antibody or antigen-binding moiety comprises a heavy chain variable region comprising CDR1, CDR2, and CDR3 comprised in the amino acid sequence of SEQ ID NO: 2; and a light chain variable region comprising CDR1, CDR2, and CDR3 comprised in the amino acid sequence of SEQ ID NO: 14.

In some embodiments, the anti-Tau antibody or antigen-binding moiety comprises a heavy chain variable region comprising CDR1, CDR2, and CDR3 comprised in the amino acid sequence of SEQ ID NO: 1; and a light chain variable region comprising CDR1, CDR2, and CDR3 comprised in the amino acid sequence of SEQ ID NO: 13.

In some embodiments, the anti-Tau antibody or antigen-binding moiety comprises a heavy chain variable region comprising CDR1, CDR2, and CDR3 comprised in the amino acid sequence of SEQ ID NO: 4; and a light chain variable region comprising CDR1, CDR2, and CDR3 comprised in the amino acid sequence of SEQ ID NO: 16.

In some embodiments, the anti-Tau antibody or antigen-binding moiety comprises a heavy chain variable region comprising CDR1, CDR2, and CDR3 comprised in the amino acid sequence of SEQ ID NO: 5; and a light chain variable region comprising CDR1, CDR2, and CDR3 comprised in the amino acid sequence of SEQ ID NO: 17.

In some embodiments, the anti-Tau antibody or antigen-binding moiety comprises a heavy chain variable region comprising CDR1, CDR2, and CDR3 comprised in the amino acid sequence of SEQ ID NO: 6; and a light chain variable region comprising CDR1, CDR2, and CDR3 comprised in the amino acid sequence of SEQ ID NO: 18.

In some embodiments, the anti-Tau antibody or antigen-binding moiety comprises a heavy chain variable region comprising CDR1, CDR2, and CDR3 comprised in the amino acid sequence of SEQ ID NO: 7; and a light chain variable region comprising CDR1, CDR2, and CDR3 comprised in the amino acid sequence of SEQ ID NO: 19.

In some embodiments, the anti-Tau antibody or antigen-binding moiety comprises a heavy chain variable region comprising CDR1, CDR2, and CDR3 comprised in the amino acid sequence of SEQ ID NO: 8; and a light chain variable region comprising CDR1, CDR2, and CDR3 comprised in the amino acid sequence of SEQ ID NO: 20.

In some embodiments, the anti-Tau antibody or antigen-binding moiety comprises a heavy chain variable region comprising CDR1, CDR2, and CDR3 comprised in the amino acid sequence of SEQ ID NO: 9; and a light chain variable region comprising CDR1, CDR2, and CDR3 comprised in the amino acid sequence of SEQ ID NO: 21.

In some embodiments, the anti-Tau antibody or antigen-binding moiety comprises a heavy chain variable region comprising CDR1, CDR2, and CDR3 comprised in the amino acid sequence of SEQ ID NO: 10; and a light chain variable region comprising CDR1, CDR2, and CDR3 comprised in the amino acid sequence of SEQ ID NO: 22.

In some embodiments, the anti-Tau antibody or antigen-binding moiety comprises a heavy chain variable region comprising CDR1, CDR2, and CDR3 comprised in the amino acid sequence of SEQ ID NO: 11; and a light chain variable region comprising CDR1, CDR2, and CDR3 comprised in the amino acid sequence of SEQ ID NO: 23.

In some embodiments, the anti-Tau antibody or antigen-binding moiety comprises a heavy chain variable region comprising CDR1, CDR2, and CDR3 comprised in the amino acid sequence of SEQ ID NO: 12; and a light chain variable region comprising CDR1, CDR2, and CDR3 comprised in the amino acid sequence of SEQ ID NO: 24.

In some embodiments, the anti-Tau antibody or antigen-binding moiety comprises a heavy chain variable region comprising CDR1, CDR2, and CDR3 comprised in the amino acid sequence of SEQ ID NO: 106; and a light chain variable region comprising CDR1, CDR2, and CDR3 comprised in the amino acid sequence of SEQ ID NO: 107.

In some embodiments, according to any of the anti-Tau antibodies or antigen-binding moieties described above, the antibody or antigen-binding moiety is a monoclonal antibody.

In some embodiments, according to any of the anti-Tau antibodies or antigen-binding moieties described above, the antibody or antigen-binding moiety is a human, humanized, or chimeric antibody.

In some embodiments, according to any of the anti-Tau antibodies or antigen-binding moieties described above, the antibody or antigen-binding moiety preferably binds to pathological human Tau species relative to normal human Tau species. In some embodiments, according to any of the anti-Tau antibodies or antigen-binding moieties described above, the antibody or antigen-binding moiety specifically binds to pathological human Tau species relative to normal human Tau species. In some embodiments, the pathological human Tau species is from a tauopathy brain.

In some embodiments, according to any of the anti-Tau antibodies or antigen-binding moieties described above, the antibody or antigen-binding moiety is an IgG1, IgG2, IgG3 or an IgG4 antibody. In some embodiments, according to any of the anti-Tau antibodies or antigen-binding moieties described above, the antibody or antigen-binding moiety is an IgG1 or an IgG4 antibody.

In another aspect, provided herein is an isolated nucleic acid encoding an antibody or antigen-binding moiety according to any of the embodiments described above.

In another aspect, provided here is a host cell comprising a nucleic acid according to any of the embodiments described above.

In another aspect, provided herein is a method of producing an antibody or antigen-binding moiety comprising culturing a host cell according to any of the embodiments described above under conditions suitable for producing the antibody or antigen-binding moiety.

In another aspect, provided herein is an immunoconjugate comprising an antibody or antigen-binding moiety according to any of the embodiments described above and a second therapeutic agent.

In another aspect, provided herein is a labeled antibody comprising an antibody or antigen-binding moiety according to any of the embodiments described above and a detectable label.

In another aspect, provided herein is a pharmaceutical composition comprising an antibody or antigen-binding moiety according to any of the embodiments described above and a pharmaceutically acceptable carrier.

In another aspect, provided herein is a method of treating or preventing a Tau-associated neurodegenerative disease in a subject, comprising administering to the subject an antibody or antigen-binding moiety according to any of the embodiments described above or a pharmaceutical composition according to any of the embodiments described above.

In another aspect, provided herein is a method of retaining or increasing cognitive memory capacity or slowing memory loss in a subject having or at risk of developing a Tau-associated neurodegenerative disease, comprising administering to the subject an antibody or antigen-binding moiety according to any of the embodiments described above or a pharmaceutical composition according to any of the embodiments described above.

In another aspect, provided herein is a method of reducing the level of Tau aggregates in a subject having or at risk of developing a Tau-associated neurodegenerative disease, comprising administering to the subject an antibody or antigen-binding moiety according to any of the embodiments described above or a pharmaceutical composition according to any of the embodiments described above, wherein i) the level of Tau aggregates and/or abnormally phosphorylated Tau is reduced in the subject as compared to their levels in the subject prior to administration of the antibody or antigen-binding moiety; and/or ii) the level of Tau aggregates and/or abnormally phosphorylated Tau accumulated at synapses of brain is reduced in the subject as compared to its level in the subject prior to administration of the antibody or antigen-binding moiety.

In another aspect, provided herein is a method of inhibiting the propagation of Tau aggregation in a subject having or at risk of developing a Tau-associated neurodegenerative disease, comprising administering to the subject an antibody or antigen-binding moiety according to any of the embodiments described above or a pharmaceutical composition according to any of the embodiments described above.

In another aspect, provided herein is a method of inhibiting Tau seeding in a subject having or at risk of developing a Tau-associated neurodegenerative disease, comprising administering to the subject an antibody or antigen-binding moiety according to any of the embodiments described above or a pharmaceutical composition according to any of the embodiments described above.

In some embodiments, according to any of the methods described above, the Tau-associated neurodegenerative disease is a tauopathy.

In some embodiments, according to any of the methods described above, the method further comprises administering to the subject at least one additional therapy. In some embodiments, the at least one additional therapy is selected from neuroprotective agents, neurological drugs, corticosteroids, antibiotics, antiviral agents, anti-Tau antibodies, Tau inhibitors, anti-amyloid beta antibodies, beta-amyloid aggregation inhibitors, anti-BACE1 antibodies, and BACE1 inhibitors. In some embodiments, the at least one additional therapy is a neuroprotective agent for use of in a combination therapy for the prevention or therapeutic treatment of neurodegenerative diseases, including delaying the onset, slowing the progression or ameliorating symptoms of neurodegenerative diseases.

In some embodiments, according to any of the methods described above, the subject is diagnosed as having or being at risk of developing a Tau-associated neurodegenerative disease. In some embodiments, the subject is diagnosed as having or being at risk of developing a tauopathy.

In another aspect, provided herein is a method of detecting pathological human Tau in a sample comprising i)

contacting the sample with an antibody or antigen-binding moiety according to any of the embodiments described above and detecting, directly or indirectly, the antibody or antigen-binding moiety; or ii) contacting the sample with a labeled antibody or antigen-binding moiety according to any of the embodiments described above and detecting the label. In some embodiments, the pathological human Tau is from a tauopathy.

The pathological Tau species described in the present disclosure is Tau aggregates and/or abnormally phosphorylated Tau. In some embodiments, the Tau aggregates and/or abnormally phosphorylated Tau is accumulated at synapses of brain. In some embodiments, the Tau aggregates and/or abnormally phosphorylated Tau is accumulated at synapses of tauopathy brain.

Examples of pathological human Tau species described in the present disclosure include, but not limited to, misordered Tau; sarkosyl-insoluble Tau; an extracellular Tau deposit; a Tau aggregate; paired helical filaments; a neurofibrillary pathology; and a hyperphosphorylated form of truncated Tau or full-length Tau.

Examples of a tauopathy described in the present disclosure includes, but not limited to, Alzheimer's disease (AD), primary age-related tauopathy (PART), chronic traumatic encephalopathy (CTE), dementia pugilistica, progressive supranuclear palsy (PSP), corticobasal degeneration (CBD), frontotemporal dementia, frontotemporal dementias with parkinsonism linked to chromosome 17 (FTDP-17), Lytico-Bodig disease, meningioangiomatosis, postencephalitic parkinsonism, subacute sclerosing pan encephalitis, Pick's Disease (PiD), corticobasal degeneration, traumatic brain injury (TBI), argyrophilic grains disease, postencephalic parkinsonism (PEP), parkinsonism dementia complex of Guam (PDCG), tangle-dominant dementia, and globular glial tauopathies (GGTs).

In some embodiments, the sample is a brain sample, a cerebrospinal fluid sample, or a blood sample. In some embodiments, the detecting comprising producing a readout comprising information about the presence of pathological human Tau in the sample. In some embodiments, the sample is from a subject and the method further comprises diagnosing whether the subject has a tauopathy, or is likely to develop a tauopathy based on the readout.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

DETAILED DESCRIPTION OF THE DISCLOSURE

Figure 1:
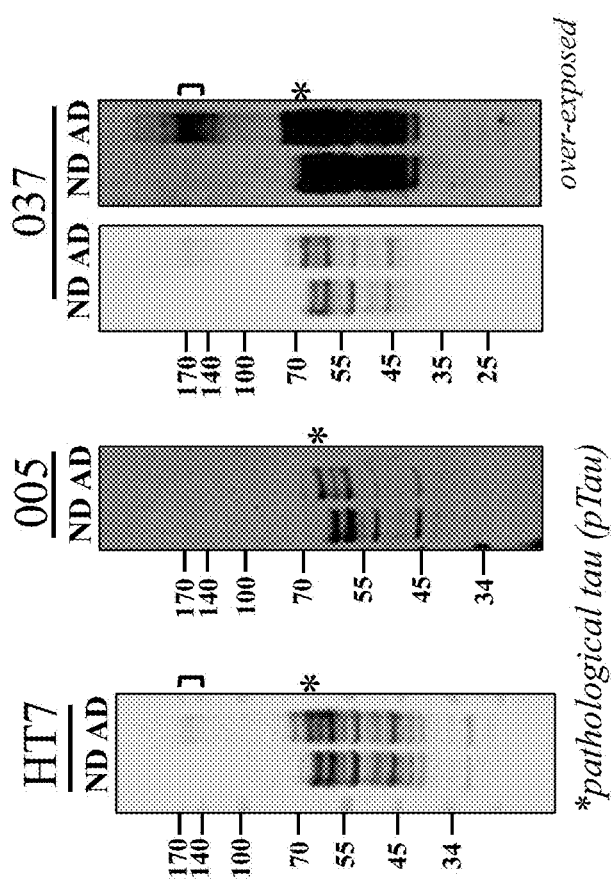
FIG. 1 shows the western blot analysis of Alzheimer's disease (AD) and Non-demented (ND) brain lysate against HT7, mAb005 and mAb037.

The present invention relates to antibodies that are capable of binding to pathological (disease-associated) Tau species, including antigen-binding moieties derived from such antibodies (e.g., antigen-binding fragments of the antibodies). Antibodies that bind pathological Tau species with minimal binding to normal (healthy) Tau species are highly desirable. Provided herein are antibodies and antigen-binding moieties that bind to human pathological Tau species and are capable of discriminating between normal and pathological Tau species. Antibodies described herein were found to preferentially bind Tau species located in synaptic fractions of tauopathy brain, and as synapse loss is an early pathological event in tauopathies, these results suggest the suitability of the antibodoes and antigen-binding derivatives thereof (such as humanized mAb005 and mAb037) for use in the clinic, where they have the potential for effecting clearance of pathological Tau with minimal effects on normal/physiological Tau species in the brains of human tauopathy patients.

Also provided are methods of using the antibodies and antigen-binding moieties described herein for eliminating and/or preventing Tau seeding and/or propagation, and methods of using the antibodies and antigen-binding moieties described herein for treating or preventing a tauopathy.

In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Definitions

The terms "pathological Tau" and "disease Tau" include pathological Tau conformers and structures and include, without limitation, all of the following: Tau Type 1A, IB, 11 A, and MB (described in detail in WO2004/007547), mis-ordered Tau, mis-disordered Tau (monomer, dimer, trimer, oligomer), mis-disordered soluble Tau, sarkosyl-insoluble Tau, extracellular Tau deposits, Tau aggregates, paired helical Tau filaments, Tau neurofibrillary pathologies, including neurofibrillary lesions, tangles, threads, fibrils, and axonal spheroids, highly phosphorylated forms of truncated or full-length Tau, or any other form of Tau associated with AD or another tauopathy that is detectable by the antibodies and/or Tau-binding fragments described herein.

"Tauopathy" or "tauopathies", as that term is used herein, defines a group of neurodegenerative diseases characterized by abnormal hyperphosphorylation of microtubule-associated protein Tau that leads to the formation of neurofibrillary tangles. Tauopathies may include, for example, Alzheimer's Disease (AD), primary age-related tauopathy (PART), chronic traumatic encephalopathy (CTE), dementia pugilistica, progressive supranuclear palsy, corticobasal degeneration, frontotemporal dementia, frontotemporal dementias with parkinsonism linked to chromosome 17 (FTDP-17), Lytico-Bodig disease, meningioangiomatosis, postencephalitic parkinsonism, subacute sclerosing pan encephalitis, Pick's Disease, corticobasal degeneration, traumatic brain injury (TBI), argyrophilic grains disease, postencephalic parkinsonism (PEP), parkinsonism dementia complex of Guam (PDCG), tangle-dominant dementia, and globular glial tauopathies (GGTs).

The terms "a Tau-associated neurodegenerative disease", "Tau-associated neurodegenerative diseases or disorders", "a Tau protein associated disease" and "Tau protein associated diseases or disorders" as used herein are meant to be tau-mediated or tau-associated neurodegenerative diseases and/or neurodegenerative pathological conditions, especially of neurodegenerative diseases and/or of neurodegenerative pathological conditions which are tauopathies and/or diseases and/or pathological conditions associated with and/or accompanied by tauopathies, preferably associated with and/or accompanied by tau aggregation.

The terms "soluble Tau" or "soluble Tau protein," as used herein, are meant to include solubilized protein species containing monomers and/or oligomers of Tau proteins/peptides, Tau-like peptides/proteins, modified or truncated Tau peptides/proteins, and/or other derivatives of Tau peptides/proteins.

The terms "insoluble Tau" or "insoluble Tau protein," as used herein, are meant to include protein species containing aggregated Tau peptides/proteins, Tau-like peptides/proteins, modified or truncated Tau peptides/proteins, and/or other derivatives of Tau peptides/proteins forming oligomeric or polymeric structures which are insoluble both in vitro in aqueous medium and in vivo in the mammalian body, more particularly in the mammalian brain. "Insoluble Tau" particularly includes neurofibrillary tangles (NFT).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "chimeric antibody" refers to an antibody in which portions of the heavy and/or light chain are derived from different sources or species.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve a desired therapeutic or prophylactic result.

The term "Fc region" herein is used to define a C-terminal region of an immunoglobulin heavy chain that contains at least a portion of the constant region. The term includes native sequence Fc regions and variant Fc regions. In some embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues or complementarity determining regions (CDRs). The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs or CDRs: three in the VH (H1, H2, H3), and three in the VL (L1, L2, L3). Exemplary CDRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)). Unless otherwise indicated, the CDRs are determined according to Kabat et al., supra. One of skill in the art will understand that the CDR designations can also be determined according to Chothia, supra, McCallum, supra, or any other scientifically accepted nomenclature system.

The terms "full-length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "variable region" or "variable domain" refers to the domain of an antibody heavy or light chain that is involved in binding of the antibody to antigen. The variable domains of the heavy chain and light chain (VH and VL, respectively) of a native antibody generally have similar structures, with each domain comprising four conserved framework regions (FRs) and three hypervariable regions (HVRs) or complementarity determining regions (CDRs).

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated" antibody is one which has been separated from a component of its natural environment.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

A "nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, such as where the individual antibodies of the population are identical and/or bind the same epitope, except for possible variant antibodies, e.g., containing naturally occurring mutations or arising during production of monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full-length of the sequences being compared.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. Pharmaceutically acceptable carriers include, but are not limited to, buffers, excipients, stabilizers, and preservatives.

The terms "treatment," "treating," and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, e.g., arresting its development; or (c) relieving the disease, e.g., causing regression of the disease. A therapeutic agent may be administered before, during, or after the onset of disease. In some embodiments, treatment inhibits one or more symptoms by at least 10%, 20%, 30%, 40%, 50%, 60%, 70%, 80%, 90%, or more. In some embodiments, treatment relieves one or more symptoms by at least 10%, 20%, 30%, 40%, 50%, 60%, 70%, 80%, 90%, or more.

As used herein, "preventing" relates to administration of a therapy (e.g., administration of an anti-Tau antibody or antigen-binding moiety thereof) to a subject before signs of the disease are detectable in the subject. The subject may be an individual at risk of developing the disease or disorder, such as an individual who has one or more risk factors known to be associated with development or onset of the disease or disorder. In some embodiments, preventing reduces one or more risk factors by at least 10%, 20%, 30%, 40%, 50%, 60%, 70%, 80%, 90%, or more. For example, in some embodiments, the preventing reduces the risk of a subject having a genetic risk factor to develop a tauopathy as known in the art. See, e.g., Avila, J. et al. *Front. Aging Neurosci.* 2015; 7:99.

The terms "individual" and "subject" are used interchangeably herein and refer to any mammalian subject, e.g., a human. In some cases, a subject for whom diagnosis, treatment, or therapy is desired is a human patient.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Anti-Tau Antibodies

In one aspect, provided herein is an antibody (e.g., an isolated antibody) or an antigen-binding moiety (e.g., an antigen-binding antibody fragment) that binds to one or more pathological Tau species (such pathological Tau species also referred to herein as "pTau," and such an antibody also referred to herein as an "anti-pTau antibody"). In some embodiments, the anti-pTau antibody or antigen-binding moiety is capable of discriminating between one or more pathological Tau species and one or more normal Tau species. In some embodiments, the anti-pTau antibody or antigen-binding moiety preferentially binds to Tau species from a tauopathy brain sample (e.g., sample from Alzheimer's disease (AD), progressive supranuclear palsy (PSP), corticobasal degeneration (CBD), or Pick's disease (PiD) brain) as compared to Tau species from a corresponding healthy brain sample. In some embodiments, the tauopathy brain sample is an AD, PSP, CBD, or PiD brain sample. In some embodiments, the brain sample is a whole brain lysate or a frontal cortex lysate, including synaptic fractions and/or sarkosyl-insoluble fractions thereof. In some embodiments, the brain sample is a sarkosyl-insoluble synaptic fraction of a brain lysate.

In some embodiments, according to any of the anti-pTau antibodies or antigen-binding moieties described herein, the anti-pTau antibody or antigen-binding moiety binds a hyperphosphorylated and sarkosyl-insoluble 64 kD Tau species from a human AD brain sample. In some embodiments, the anti-pTau antibody or antigen-binding moiety binds to a 68 kD Tau species from the human AD brain sample. In some embodiments, the anti-pTau antibody or antigen-binding moiety does not bind to a 140 kD Tau species from the human AD brain sample. In some embodiments, the anti-pTau antibody or antigen-binding moiety does not bind to a 170 kD Tau species from the human AD brain sample. In some embodiments, the brain sample is a brain lysate, such as a lysate prepared from whole brain, frontal cortex, mid brain, thalamus, putamen, or superior frontal gyrus tissue. In some embodiments, the brain sample is a sarkosyl-insoluble fraction of a brain lysate, such as a lysate prepared from whole brain, frontal cortex, mid brain, thalamus, putamen, or superior frontal gyrus tissue.

Exemplary Anti-pTau Antibodies

In some embodiments, provided herein is an anti-pTau antibody (e.g., an isolated anti-pTau antibody) or antigen-binding moiety thereof comprising: a) a heavy chain variable region comprising a complementary determining region (CDR) 3 comprising the amino acid sequence of any one of SEQ ID NOs: 71-81 or a variant thereof having at least 80%, at least 90%, or at least 95% sequence identity to the amino acid sequence of any one of SEQ ID NOs: 71-81; and/or b) a light chain variable region comprising a CDR3 comprising the amino acid sequence of any one of SEQ ID NOs: 96-105 or a variant thereof having at least 80%, at least 90%, or at least 95% sequence identity to the amino acid sequence of any one of SEQ ID NOS: 96-105. In some embodiments, the heavy chain variable region comprises a CDR3 comprising the amino acid sequence of any one of SEQ ID NOs: 71-81 or a variant thereof having no more than 3, no more than 2, or no more than 1 mismatches compared to the amino acid sequence of any one of SEQ ID NOs: 71-81; and/or b) a light chain variable region comprising a CDR3 comprising the amino acid sequence of any one of SEQ ID NOs: 96-105 or a variant thereof having no more than 3, no more than 2, or no more than 1 mismatches compared to the amino acid sequence of any one of SEQ ID NOs: 96-105. In some embodiments, the heavy chain variable region comprises a CDR3 comprising the amino acid sequence of any one of SEQ ID NOs: 71-81; and/or b) a light chain variable region comprising a CDR3 comprising the amino acid sequence of any one of SEQ ID NOs: 96-105.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 72 or a variant thereof having at least 80%, at least 90%, or at least 95% sequence identity to the amino acid sequence of SEQ ID NO: 72; and the light chain CDR3 comprises the amino acid sequence of SEQ ID NO: 97 or a variant thereof having at least 80%, at least 90%, or at least 95% sequence identity to the amino acid sequence of SEQ ID NO: 97. In some embodiments, the heavy chain CDR3 comprises the amino acid sequence of SEQ ID NO: 72 and the light chain CDR3 comprises the amino acid sequence of SEQ ID NO: 97. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 50 and 61, respectively, or variants thereof having at least 80%, at least 90%, or at least 95% sequence identity to the amino acid sequences of SEQ ID NOs: 50 and 61, respectively; and the light chain CDR1 and CDR2 comprise the amino acid sequences of SEQ ID NOs: 83 and 91, respectively, or variants thereof having at least 80%, at least 90%, or at least 95% sequence identity to the amino acid sequences of SEQ ID NOs: 83 and 91, respectively. In some embodiments, the heavy chain CDR1 and CDR2 comprise the amino acid sequences of SEQ ID NOs: 50 and 61, respectively; and the light chain CDR1 and CDR2 comprise the amino acid sequences of SEQ ID NOs: 83 and 91, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 71 or a variant thereof having at least 80%, at least 90%, or at least 95% sequence identity to the amino acid sequence of SEQ ID NO: 71; and the light chain CDR3 comprises the amino acid sequence of SEQ ID NO: 96 or a variant thereof having at least 80%, at least 90%, or at least 95% sequence identity to the amino acid sequence of SEQ ID NO: 96. In some embodiments, the heavy chain CDR3 comprises the amino acid sequence of SEQ ID NO: 71 and the light chain CDR3 comprises the amino acid sequence of SEQ ID NO: 96. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 49 and 60, respectively, or variants thereof having at least 80%, at least 90%, or at least 95% sequence identity to the amino acid sequences of SEQ ID NOs: 49 and 60, respectively; and the light chain CDR1 and CDR2 comprise the amino acid sequences of SEQ ID NOs: 82 and 91, respectively, or variants thereof having at least 80%, at least 90%, or at least 95% sequence identity to the amino acid sequences of SEQ ID NOs: 82 and 91, respectively. In some embodiments, the heavy chain CDR1 and CDR2 comprise the amino acid sequences of SEQ ID NOs: 49 and 60, respectively; and the light chain CDR1 and CDR2 comprise the amino acid sequences of SEQ ID NOs: 82 and 91, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 73 or a variant thereof having at least 80%, at least 90%, or at least 95% sequence identity to the amino acid sequence of SEQ ID NO: 73; and the light chain CDR3 comprises the amino acid sequence of SEQ ID NO: 98 or a variant thereof having at least 80%, at least 90%, or at least 95% sequence identity to the amino acid sequence of SEQ ID NO: 98. In some embodiments, the heavy chain CDR3 comprises the amino acid sequence of SEQ ID NO: 73 and the light chain CDR3 comprises the amino acid sequence of SEQ ID NO: 98. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 51 and 62, respectively, or variants thereof having at least 80%, at least 90%, or at least 95% sequence identity to the amino acid sequences of SEQ ID NOs: 51 and 62, respectively; and the light chain CDR1 and CDR2 comprise the amino acid sequences of SEQ ID NOs: 84 and 91, respectively, or variants thereof having at least 80%, at least 90%, or at least 95% sequence identity to the amino acid sequences of SEQ ID NOs: 84 and 91, respectively. In some embodiments, the heavy chain CDR1 and CDR2 comprise the amino acid sequences of SEQ ID NOs: 51 and 62, respectively; and the light chain CDR1 and CDR2 comprise the amino acid sequences of SEQ ID NOs: 84 and 91, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 74 or a variant thereof having at least 80%, at least 90%, or at least 95% sequence identity to the amino acid sequence of SEQ ID NO: 74; and the light chain CDR3 comprises the amino acid sequence of SEQ ID NO: 99 or a variant thereof having at least 80%, at least 90%, or at least 95% sequence identity to the amino acid sequence of SEQ ID NO: 99. In some embodiments, the heavy chain CDR3 comprises the amino acid sequence of SEQ ID NO: 74 and the light chain CDR3 comprises the amino acid sequence of SEQ ID NO: 99. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 52 and 63, respectively, or variants thereof having at least 80%, at least 90%, or at least 95% sequence identity to the amino acid sequences of SEQ ID NOs: 52 and 63, respectively; and the light chain CDR1 and CDR2 comprise the amino acid sequences of SEQ ID NOs: 85 and 92, respectively, or variants thereof having at least 80%, at least 90%, or at least 95% sequence identity to the amino acid sequences of SEQ ID NOs: 85 and 92, respectively. In some embodiments, the heavy chain CDR1 and CDR2 comprise the amino acid sequences of SEQ ID NOs: 52 and 63, respectively; and the light chain CDR1 and CDR2 comprise the amino acid sequences of SEQ ID NOs: 85 and 92, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 75 or a variant thereof having at least 80%, at least 90%, or at least 95% sequence identity to the amino acid sequence of SEQ ID NO: 75; and the light chain CDR3 comprises the amino acid sequence of SEQ ID NO: 100 or a variant thereof having at least 80%, at least 90%, or at least 95% sequence identity to the amino acid sequence of SEQ ID NO: 100. In some embodiments, the heavy chain CDR3 comprises the amino acid sequence of SEQ ID NO: 75 and the light chain CDR3 comprises the amino acid sequence of SEQ ID NO: 100. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 53 and 64, respectively, or variants thereof having at least 80%, at least 90%, or at least 95% sequence identity to the amino acid sequences of SEQ ID NOs: 53 and 64, respectively; and the light chain CDR1 and CDR2 comprise the amino acid sequences of SEQ ID NOs: 86 and 93, respectively, or variants thereof having at least 80%, at least 90%, or at least 95% sequence identity to the amino acid sequences of SEQ ID NOs: 86 and 93, respectively. In some embodiments, the heavy chain CDR1 and CDR2 comprise the amino acid sequences of SEQ ID NOs: 53 and 64, respectively; and the light chain CDR1 and CDR2 comprise the amino acid sequences of SEQ ID NOs: 86 and 93, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 76 or a variant thereof having at least 80%, at least 90%, or at least 95% sequence identity to the amino acid sequence of SEQ ID NO: 76; and the light chain CDR3 comprises the amino acid sequence of SEQ ID NO: 101 or a variant thereof having at least 80%, at least 90%, or at least 95% sequence identity to the amino acid sequence of SEQ ID NO: 101. In some embodiments, the heavy chain CDR3 comprises the amino acid sequence of SEQ ID NO: 76 and the light chain CDR3 comprises the amino acid sequence of SEQ ID NO: 101. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 54 and 65, respectively, or variants thereof having at least 80%, at least 90%, or at least 95% sequence identity to the amino acid sequences of SEQ ID NOs: 54 and 65, respectively; and the light chain CDR1 and CDR2 comprise the amino acid sequences of SEQ ID NOs: 87 and 93, respectively, or variants thereof having at least 80%, at least 90%, or at least 95% sequence identity to the amino acid sequences of SEQ ID NOs: 87 and 93, respectively. In some embodiments, the heavy chain CDR1 and CDR2 comprise the amino acid sequences of SEQ ID NOs: 54 and 65, respectively; and the light chain CDR1 and CDR2 comprise the amino acid sequences of SEQ ID NOs: 87 and 93, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 77 or a variant thereof having at least 80%, at least 90%, or at least 95% sequence identity to the amino acid sequence of SEQ ID NO: 77; and the light chain CDR3 comprises the amino acid sequence of SEQ ID NO: 102 or a variant thereof having at least 80%, at least 90%, or at least 95% sequence identity to the amino acid sequence of SEQ ID NO: 102. In some embodiments, the heavy chain CDR3 comprises the amino acid sequence of SEQ ID NO: 77 and the light chain CDR3 comprises the amino acid sequence of SEQ ID NO: 102. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 55 and 66, respectively, or variants thereof having at least 80%, at least 90%, or at least 95% sequence identity to the amino acid sequences of SEQ ID NOs: 55 and 66, respectively; and the light chain CDR1 and CDR2 comprise the amino acid sequences of SEQ ID NOs: 83 and 91, respectively, or variants thereof having at least 80%, at least 90%, or at least 95% sequence identity to the amino acid sequences of SEQ ID NOs: 83 and 91, respectively. In some embodiments, the heavy chain CDR1 and CDR2 comprise the amino acid sequences of SEQ ID NOs: 55 and 66, respectively; and the light chain CDR1 and CDR2 comprise the amino acid sequences of SEQ ID NOs: 83 and 91, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 78 or a variant thereof having at least 80%, at least 90%, or at least 95% sequence identity to the amino acid sequence of SEQ ID NO: 78; and the light chain CDR3 comprises the amino acid sequence of SEQ ID NO: 103 or a variant thereof having at least 80%, at least 90%, or at least 95% sequence identity to the amino acid sequence of SEQ ID NO: 103. In some embodiments, the heavy chain CDR3 comprises the amino acid sequence of SEQ ID NO: 78 and the light chain CDR3 comprises the amino acid sequence of SEQ ID NO: 103. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 56 and 67, respectively, or variants thereof having at least 80%, at least 90%, or at least 95% sequence identity to the amino acid sequences of SEQ ID NOs: 56 and 67, respectively; and the light chain CDR1 and CDR2 comprise the amino acid sequences of SEQ ID NOs: 88 and 94, respectively, or variants thereof having at least 80%, at least 90%, or at least 95% sequence identity to the amino acid sequences of SEQ ID NOs: 88 and 94, respectively. In some embodiments, the heavy chain CDR1 and CDR2 comprise the amino acid sequences of SEQ ID NOs: 56 and 67, respectively; and the light chain CDR1 and CDR2 comprise the amino acid sequences of SEQ ID NOs: 88 and 94, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 79 or a variant thereof having at least 80%, at least 90%, or at least 95% sequence identity to the amino acid sequence of SEQ ID NO: 79; and the light chain CDR3 comprises the amino acid sequence of SEQ ID NO: 98 or a variant thereof having at least 80%, at least 90%, or at least 95% sequence identity to the amino acid sequence of SEQ ID NO: 98. In some embodiments, the heavy chain CDR3 comprises the amino acid sequence of SEQ ID NO: 79 and the light chain CDR3 comprises the amino acid sequence of SEQ ID NO: 98. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 57 and 68, respectively, or variants thereof having at least 80%, at least 90%, or at least 95% sequence identity to the amino acid sequences of SEQ ID NOs: 57 and 68, respectively; and the light chain CDR1 and CDR2 comprise the amino acid sequences of SEQ ID NOs: 89 and 91, respectively, or variants thereof having at least 80%, at least 90%, or at least 95% sequence identity to the amino acid sequences of SEQ ID NOs: 89 and 91, respectively. In some embodiments, the heavy chain CDR1 and CDR2 comprise the amino acid sequences of SEQ ID NOs: 57 and 68, respectively; and the light chain CDR1 and CDR2 comprise the amino acid sequences of SEQ ID NOs: 89 and 91, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 80 or a variant thereof having at least 80%, at least 90%, or at least 95% sequence identity to the amino acid sequence of SEQ ID NO: 80; and the light chain CDR3 comprises the amino acid sequence of SEQ ID NO: 104 or a variant thereof having at least 80%, at least 90%, or at least 95% sequence identity to the amino acid sequence of SEQ ID NO: 104. In some embodiments, the heavy chain CDR3 comprises the amino acid sequence of SEQ ID NO: 80 and the light chain CDR3 comprises the amino acid sequence of SEQ ID NO: 104. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 58 and 69, respectively, or variants thereof having at least 80%, at least 90%, or at least 95% sequence identity to the amino acid sequences of SEQ ID NOs: 58 and 69, respectively; and the light chain CDR1 and CDR2 comprise the amino acid sequences of SEQ ID NOs: 90 and 95, respectively, or variants thereof having at least 80%, at least 90%, or at least 95% sequence identity to the amino acid sequences of SEQ ID NOs: 90 and 95, respectively. In some embodiments, the heavy chain CDR1 and CDR2 comprise the amino acid sequences of SEQ ID NOs: 58 and 69, respectively; and the light chain CDR1 and CDR2 comprise the amino acid sequences of SEQ ID NOs: 90 and 95, respectively.

In some embodiments, provided herein is an anti-pTau antibody (e.g., an isolated anti-pTau antibody) or antigen-binding moiety thereof comprising a heavy chain variable region comprising a CDR3 and a light chain variable region comprising a CDR3, wherein the heavy chain CDR3 comprises the amino acid sequence of SEQ ID NO: 81 or a variant thereof having at least 80%, at least 90%, or at least 95% sequence identity to the amino acid sequence of SEQ ID NO: 81; and the light chain CDR3 comprises the amino acid sequence of SEQ ID NO: 105 or a variant thereof having at least 80%, at least 90%, or at least 95% sequence identity to the amino acid sequence of SEQ ID NO: 105. In some embodiments, the heavy chain CDR3 comprises the amino acid sequence of SEQ ID NO: 81 and the light chain CDR3 comprises the amino acid sequence of SEQ ID NO: 105. In some embodiments, the heavy chain variable region further comprises a CDR1 and a CDR2 and the light chain variable region further comprises a CDR1 and a CDR2, wherein the heavy chain CDR1 and CDR2 comprise the amino acid sequences of SEQ ID NOs: 59 and 70, respectively, or variants thereof having at least 80%, at least 90%, or at least 95% sequence identity to the amino acid sequences of SEQ ID NOs: 59 and 70, respectively; and the light chain CDR1 and CDR2 comprise the amino acid sequences of SEQ ID NOs: 87 and 93, respectively, or variants thereof having at least 80%, at least 90%, or at least 95% sequence identity to the amino acid sequences of SEQ ID NOs: 87 and 93, respectively. In some embodiments, the heavy chain CDR1 and CDR2 comprise the amino acid sequences of SEQ ID NOs: 59 and 70, respectively; and the light chain CDR1 and CDR2 comprise the amino acid sequences of SEQ ID NOs: 87 and 93, respectively.

In some embodiments, provided herein is an anti-pTau antibody (e.g., an isolated anti-pTau antibody) or antigen-binding moiety thereof comprising: a) a heavy chain variable region comprising i) a CDR1 comprising the amino acid sequence of any one of SEQ ID NOs: 49-59 or a variant thereof having at least 80%, at least 90%, or at least 95% sequence identity to the amino acid sequence of any one of SEQ ID NOs: 49-59; ii) a CDR2 comprising the amino acid sequence of any one of SEQ ID NOs: 60-70 or a variant thereof having at least 80%, at least 90%, or at least 95% sequence identity to the amino acid sequence of any one of SEQ ID NOs: 60-70; and/or iii) a CDR3 comprising the amino acid sequence of any one of SEQ ID NOs: 71-81 or a variant thereof having at least 80%, at least 90%, or at least 95% sequence identity to the amino acid sequence of any one of SEQ ID NOs: 71-81; and/or b) a light chain variable region comprising iv) a CDR1 comprising the amino acid sequence of any one of SEQ ID NOs: 82-90 or a variant thereof having at least 80%, at least 90%, or at least 95% sequence identity to the amino acid sequence of any one of SEQ ID NOs: 82-90; v) a CDR2 comprising the amino acid sequence of any one of SEQ ID NOs: 91-95 or a variant thereof having at least 80%, at least 90%, or at least 95% sequence identity to the amino acid sequence of any one of SEQ ID NOs: 91-95; and/or vi) a CDR3 comprising the amino acid sequence of any one of SEQ ID NOs: 96-105 or a variant thereof having at least 80%, at least 90%, or at least 95% sequence identity to the amino acid sequence of any one of SEQ ID NOS: 96-105. In some embodiments, a) the heavy chain variable region comprises i) a CDR1 comprising the amino acid sequence of any one of SEQ ID NOs: 49-59 or a variant thereof having no more than 3, no more than 2, or no more than 1 mismatches compared to the amino acid sequence of any one of SEQ ID NOs: 49-59; ii) a CDR2 comprising the amino acid sequence of any one of SEQ ID NOs: 60-70 or a variant thereof having no more than 3, no more than 2, or no more than 1 mismatches compared to the amino acid sequence of any one of SEQ ID NOs: 60-70; and/or iii) a CDR3 comprising the amino acid sequence of any one of SEQ ID NOs: 71-81 or a variant thereof having no more than 3, no more than 2, or no more than 1 mismatches compared to the amino acid sequence of any one of SEQ ID NOs: 71-81; and/or b) the light chain variable region comprises iv) a CDR1 comprising the amino acid sequence of any one of SEQ ID NOs: 82-90 or a variant thereof having no more than 3, no more than 2, or no more than 1 mismatches compared to the amino acid sequence of any one of SEQ ID NOs: 82-90; v) a CDR2 comprising the amino acid sequence of any one of SEQ ID NOs: 91-95 or a variant thereof having no more than 3, no more than 2, or no more than 1 mismatches compared to the amino acid sequence of any one of SEQ ID NOs: 91-95; and/or vi) a CDR3 comprising the amino acid sequence of any one of SEQ ID NOs: 96-105 or a variant thereof having no more than 3, no more than 2, or no more than 1 mismatches compared to the amino acid sequence of any one of SEQ ID NOS: 96-105. In some embodiments, a) the heavy chain variable region comprises i) a CDR1 comprising the amino acid sequence of any one of SEQ ID NOs: 49-59; ii) a CDR2 comprising the amino acid sequence of any one of SEQ ID NOs: 60-70; and/or iii) a CDR3 comprising the amino acid sequence of any one of SEQ ID NOs: 71-81; and/or b) the light chain variable region comprises iv) a CDR1 comprising the amino acid sequence of any one of SEQ ID NOs: 82-90; v) a CDR2 comprising the amino acid sequence of any one of SEQ ID NOs: 91-95; and/or vi) a CDR3 comprising the amino acid sequence of any one of SEQ ID NOs: 96-105. In some embodiments, the heavy chain and/or light chain CDR sequences are as indicated for a given antibody clone shown in Tables 1 and 2.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 50, 61, and 72, respectively, or variants thereof having at least 80%, at least 90%, or at least 95% sequence identity to the amino acid sequences of SEQ ID NOs: 50, 61, and 72, respectively; and the light chain CDR1, CDR2, and CDR3 comprise the amino acid sequences of SEQ ID NOs: 83, 91, and 97, respectively, or variants thereof having at least 80%, at least 90%, or at least 95% sequence identity to the amino acid sequences of SEQ ID NOs: 83, 91, and 97, respectively. In some embodiments, the heavy chain CDR1, CDR2, and CDR3 comprise the amino acid sequences of SEQ ID NOs: 50, 61, and 72, respectively; and the light chain CDR1, CDR2, and CDR3 comprise the amino acid sequences of SEQ ID NOs: 83, 91, and 97, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 49, 60, and 71, respectively, or variants thereof having at least 80%, at least 90%, or at least 95% sequence identity to the amino acid sequences of SEQ ID NOs: 49, 60, and 71, respectively; and the light chain CDR1, CDR2, and CDR3 comprise the amino acid sequences of SEQ ID NOs: 82, 91, and 96, respectively, or variants thereof having at least 80%, at least 90%, or at least 95% sequence identity to the amino acid sequences of SEQ ID NOs: 82, 91, and 96, respectively. In some embodiments, the heavy chain CDR1, CDR2, and CDR3 comprise the amino acid sequences of SEQ ID NOs: 49, 60, and 71, respectively; and the light chain CDR1, CDR2, and CDR3 comprise the amino acid sequences of SEQ ID NOs: 82, 91, and 96, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 51, 62, and 73, respectively, or variants thereof having at least 80%, at least 90%, or at least 95% sequence identity to the amino acid sequences of SEQ ID NOs: 51, 62, and 73, respectively; and the light chain CDR1, CDR2, and CDR3 comprise the amino acid sequences of SEQ ID NOs: 84, 91, and 98, respectively, or variants thereof having at least 80%, at least 90%, or at least 95% sequence identity to the amino acid sequences of SEQ ID NOs: 84, 91, and 98, respectively. In some embodiments, the heavy chain CDR1, CDR2, and CDR3 comprise the amino acid sequences of SEQ ID NOs: 51, 62, and 73, respectively; and the light chain CDR1, CDR2, and CDR3 comprise the amino acid sequences of SEQ ID NOs: 84, 91, and 98, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 52, 63, and 74, respectively, or variants thereof having at least 80%, at least 90%, or at least 95% sequence identity to the amino acid sequences of SEQ ID NOs: 52, 63, and 74, respectively; and the light chain CDR1, CDR2, and CDR3 comprise the amino acid sequences of SEQ ID NOs: 85, 92, and 99, respectively, or variants thereof having at least 80%, at least 90%, or at least 95% sequence identity to the amino acid sequences of SEQ ID NOs: 85, 92, and 99, respectively. In some embodiments, the heavy chain CDR1, CDR2, and CDR3 comprise the amino acid sequences of SEQ ID NOs: 52, 63, and 74, respectively; and the light chain CDR1, CDR2, and CDR3 comprise the amino acid sequences of SEQ ID NOs: 85, 92, and 99, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 53, 64, and 75, respectively, or variants thereof having at least 80%, at least 90%, or at least 95% sequence identity to the amino acid sequences of SEQ ID NOs: 53, 64, and 75, respectively; and the light chain CDR1, CDR2, and CDR3 comprise the amino acid sequences of SEQ ID NOs: 86, 93, and 100, respectively, or variants thereof having at least 80%, at least 90%, or at least 95% sequence identity to the amino acid sequences of SEQ ID NOs: 86, 93, and 100, respectively. In some embodiments, the heavy chain CDR1, CDR2, and CDR3 comprise the amino acid sequences of SEQ ID NOs: 53, 64, and 75, respectively; and the light chain CDR1, CDR2, and CDR3 comprise the amino acid sequences of SEQ ID NOs: 86, 93, and 100, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 54, 65, and 76, respectively, or variants thereof having at least 80%, at least 90%, or at least 95% sequence identity to the amino acid sequences of SEQ ID NOs: 54, 65, and 76, respectively; and the light chain CDR1, CDR2, and CDR3 comprise the amino acid sequences of SEQ ID NOs: 87, 93, and 101, respectively, or variants thereof having at least 80%, at least 90%, or at least 95% sequence identity to the amino acid sequences of SEQ ID NOs: 87, 93, and 101, respectively. In some embodiments, the heavy chain CDR1, CDR2, and CDR3 comprise the amino acid sequences of SEQ ID NOs: 54, 65, and 76, respectively; and the light chain CDR1, CDR2, and CDR3 comprise the amino acid sequences of SEQ ID NOs: 87, 93, and 101, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 55, 66, and 77, respectively, or variants thereof having at least 80%, at least 90%, or at least 95% sequence identity to the amino acid sequences of SEQ ID NOs: 55, 66, and 77, respectively; and the light chain CDR1, CDR2, and CDR3 comprise the amino acid sequences of SEQ ID NOs: 83, 91, and 102, respectively, or variants thereof having at least 80%, at least 90%, or at least 95% sequence identity to the amino acid sequences of SEQ ID NOs: 83, 91, and 102, respectively. In some embodiments, the heavy chain CDR1, CDR2, and CDR3 comprise the amino acid sequences of SEQ ID NOs: 55, 66, and 77, respectively; and the light chain CDR1, CDR2, and CDR3 comprise the amino acid sequences of SEQ ID NOs: 83, 91, and 102, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 56, 67, and 78, respectively, or variants thereof having at least 80%, at least 90%, or at least 95% sequence identity to the amino acid sequences of SEQ ID NOs: 56, 67, and 78, respectively; and the light chain CDR1, CDR2, and CDR3 comprise the amino acid sequences of SEQ ID NOs: 88, 94, and 103, respectively, or variants thereof having at least 80%, at least 90%, or at least 95% sequence identity to the amino acid sequences of SEQ ID NOs: 88, 94, and 103, respectively. In some embodiments, the heavy chain CDR1, CDR2, and CDR3 comprise the amino acid sequences of SEQ ID NOs: 56, 67, and 78, respectively; and the light chain CDR1, CDR2, and CDR3 comprise the amino acid sequences of SEQ ID NOs: 88, 94, and 103, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 57, 68, and 79, respectively, or variants thereof having at least 80%, at least 90%, or at least 95% sequence identity to the amino acid sequences of SEQ ID NOs: 57, 68, and 79, respectively; and the light chain CDR1, CDR2, and CDR3 comprise the amino acid sequences of SEQ ID NOs: 89, 91, and 98, respectively, or variants thereof having at least 80%, at least 90%, or at least 95% sequence identity to the amino acid sequences of SEQ ID NOs: 89, 91, and 98, respectively. In some embodiments, the heavy chain CDR1, CDR2, and CDR3 comprise the amino acid sequences of SEQ ID NOs: 57, 68, and 79, respectively; and the light chain CDR1, CDR2, and CDR3 comprise the amino acid sequences of SEQ ID NOs: 89, 91, and 98, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 58, 69, and 80, respectively, or variants thereof having at least 80%, at least 90%, or at least 95% sequence identity to the amino acid sequences of SEQ ID NOs: 58, 69, and 80, respectively; and the light chain CDR1, CDR2, and CDR3 comprise the amino acid sequences of SEQ ID NOs: 90, 95, and 104, respectively, or variants thereof having at least 80%, at least 90%, or at least 95% sequence identity to the amino acid sequences of SEQ ID NOs: 90, 95, and 104, respectively. In some embodiments, the heavy chain CDR1, CDR2, and CDR3 comprise the amino acid sequences of SEQ ID NOs: 58, 69, and 80, respectively; and the light chain CDR1, CDR2, and CDR3 comprise the amino acid sequences of SEQ ID NOs: 90, 95, and 104, respectively.

In some embodiments, provided herein is an anti-pTau antibody (e.g., an isolated anti-pTau antibody) or antigen-binding moiety thereof comprising a heavy chain variable region comprising a CDR1, a CDR2, and a CDR3 and a light chain variable region comprising a CDR1, a CDR2, and a CDR3, wherein the heavy chain CDR1, CDR2, and CDR3 comprise the amino acid sequences of SEQ ID NOs: 59, 70, and 81, respectively, or variants thereof having at least 80%, at least 90%, or at least 95% sequence identity to the amino acid sequences of SEQ ID NOs: 59, 70, and 81, respectively; and the light chain CDR1, CDR2, and CDR3 comprise the amino acid sequences of SEQ ID NOs: 87, 93, and 105, respectively, or variants thereof having at least 80%, at least 90%, or at least 95% sequence identity to the amino acid sequences of SEQ ID NOs: 87, 93, and 105, respectively. In some embodiments, the heavy chain CDR1, CDR2, and CDR3 comprise the amino acid sequences of SEQ ID NOs: 59, 70, and 81, respectively; and the light chain CDR1, CDR2, and CDR3 comprise the amino acid sequences of SEQ ID NOs: 87, 93, and 105, respectively.

In some embodiments, provided herein is an anti-pTau antibody (e.g., an isolated anti-pTau antibody) or antigen-binding moiety thereof comprising a heavy chain variable region comprising the amino acid sequence of any one of SEQ ID NOs: 1-12 or a variant thereof having at least 80%, at least 90%, at least 95%, at least 96%, at least 97%, at least 98%, or at least 99% sequence identity to the amino acid sequence of any one of SEQ ID NOs: 1-12; and/or a light chain variable region comprising the amino acid sequence of any one of SEQ ID NOs: 13-24 or a variant thereof having at least 80%, at least 90%, at least 95%, at least 96%, at least 97%, at least 98%, or at least 99% sequence identity to the amino acid sequence of any one of SEQ ID NOs: 13-24. In some embodiments, where a variable region comprises a variant of a reference amino acid sequence disclosed herein, each of the CDRs in the variable region has at least 80%, at least 90%, or at least 95% sequence identity to the corresponding CDR in the reference amino acid sequence. In some embodiments, each of the CDRs in the variable region has 100% sequence identity to the corresponding CDR in the reference amino acid sequence. In some embodiments, the heavy chain variable region comprises the amino acid sequence of any one of SEQ ID NOs: 1-12; and/or the light chain variable region comprises the amino acid sequence of any one of SEQ ID NOs: 13-24. In some embodiments, the heavy chain and light chain variable regions are as indicated for a given antibody clone shown in Table 3.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 1 or a variant thereof having at least 80%, at least 90%, at least 95%, at least 96%, at least 97%, at least 98%, or at least 99% sequence identity to the amino acid sequence of SEQ ID NO: 1; and/or a light chain variable region comprising the amino acid sequence of SEQ ID NO: 13 or a variant thereof having at least 80%, at least 90%, at least 95%, at least 96%, at least 97%, at least 98%, or at least 99% sequence identity to the amino acid sequence of SEQ ID NO: 13. In some embodiments, the heavy chain variable region comprises the amino acid sequence of SEQ ID NOs: 1; and/or the light chain variable region comprises the amino acid sequence of SEQ ID NO: 13.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 2 or a variant thereof having at least 80%, at least 90%, at least 95%, at least 96%, at least 97%, at least 98%, or at least 99% sequence identity to the amino acid sequence of SEQ ID NO: 2; and/or a light chain variable region comprising the amino acid sequence of SEQ ID NO: 14 or a variant thereof having at least 80%, at least 90%, at least 95%, at least 96%, at least 97%, at least 98%, or at least 99% sequence identity to the amino acid sequence of SEQ ID NO: 14. In some embodiments, the heavy chain variable region comprises the amino acid sequence of SEQ ID NOs: 2; and/or the light chain variable region comprises the amino acid sequence of SEQ ID NO: 14.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 3 or a variant thereof having at least 80%, at least 90%, at least 95%, at least 96%, at least 97%, at least 98%, or at least 99% sequence identity to the amino acid sequence of SEQ ID NO: 3; and/or a light chain variable region comprising the amino acid sequence of SEQ ID NO: 15 or a variant thereof having at least 80%, at least 90%, at least 95%, at least 96%, at least 97%, at least 98%, or at least 99% sequence identity to the amino acid sequence of SEQ ID NO: 15. In some embodiments, the heavy chain variable region comprises the amino acid sequence of SEQ ID NOs: 3; and/or the light chain variable region comprises the amino acid sequence of SEQ ID NO: 15.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 4 or a variant thereof having at least 80%, at least 90%, at least 95%, at least 96%, at least 97%, at least 98%, or at least 99% sequence identity to the amino acid sequence of SEQ ID NO: 4; and/or a light chain variable region comprising the amino acid sequence of SEQ ID NO: 16 or a variant thereof having at least 80%, at least 90%, at least 95%, at least 96%, at least 97%, at least 98%, or at least 99% sequence identity to the amino acid sequence of SEQ ID NO: 16. In some embodiments, the heavy chain variable region comprises the amino acid sequence of SEQ ID NOs: 4; and/or the light chain variable region comprises the amino acid sequence of SEQ ID NO: 16.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 5 or a variant thereof having at least 80%, at least 90%, at least 95%, at least 96%, at least 97%, at least 98%, or at least 99% sequence identity to the amino acid sequence of SEQ ID NO: 5; and/or a light chain variable region comprising the amino acid sequence of SEQ ID NO: 17 or a variant thereof having at least 80%, at least 90%, at least 95%, at least 96%, at least 97%, at least 98%, or at least 99% sequence identity to the amino acid sequence of SEQ ID NO: 17. In some embodiments, the heavy chain variable region comprises the amino acid sequence of SEQ ID NOs: 5; and/or the light chain variable region comprises the amino acid sequence of SEQ ID NO: 17.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 6 or a variant thereof having at least 80%, at least 90%, at least 95%, at least 96%, at least 97%, at least 98%, or at least 99% sequence identity to the amino acid sequence of SEQ ID NO: 6; and/or a light chain variable region comprising the amino acid sequence of SEQ ID NO: 18 or a variant thereof having at least 80%, at least 90%, at least 95%, at least 96%, at least 97%, at least 98%, or at least 99% sequence identity to the amino acid sequence of SEQ ID NO: 18. In some embodiments, the heavy chain variable region comprises the amino acid sequence of SEQ ID NOs: 6; and/or the light chain variable region comprises the amino acid sequence of SEQ ID NO: 18.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 7 or a variant thereof having at least 80%, at least 90%, at least 95%, at least 96%, at least 97%, at least 98%, or at least 99% sequence identity to the amino acid sequence of SEQ ID NO: 7; and/or a light chain variable region comprising the amino acid sequence of SEQ ID NO: 19 or a variant thereof having at least 80%, at least 90%, at least 95%, at least 96%, at least 97%, at least 98%, or at least 99% sequence identity to the amino acid sequence of SEQ ID NO: 19. In some embodiments, the heavy chain variable region comprises the amino acid sequence of SEQ ID NOs: 7; and/or the light chain variable region comprises the amino acid sequence of SEQ ID NO: 19.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 8 or a variant thereof having at least 80%, at least 90%, at least 95%, at least 96%, at least 97%, at least 98%, or at least 99% sequence identity to the amino acid sequence of SEQ ID NO: 8; and/or a light chain variable region comprising the amino acid sequence of SEQ ID NO: 20 or a variant thereof having at least 80%, at least 90%, at least 95%, at least 96%, at least 97%, at least 98%, or at least 99% sequence identity to the amino acid sequence of SEQ ID NO: 20. In some embodiments, the heavy chain variable region comprises the amino acid sequence of SEQ ID NOs: 8; and/or the light chain variable region comprises the amino acid sequence of SEQ ID NO: 20.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 9 or a variant thereof having at least 80%, at least 90%, at least 95%, at least 96%, at least 97%, at least 98%, or at least 99% sequence identity to the amino acid sequence of SEQ ID NO: 9; and/or a light chain variable region comprising the amino acid sequence of SEQ ID NO: 21 or a variant thereof having at least 80%, at least 90%, at least 95%, at least 96%, at least 97%, at least 98%, or at least 99% sequence identity to the amino acid sequence of SEQ ID NO: 21. In some embodiments, the heavy chain variable region comprises the amino acid sequence of SEQ ID NOs: 9; and/or the light chain variable region comprises the amino acid sequence of SEQ ID NO: 21.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 10 or a variant thereof having at least 80%, at least 90%, at least 95%, at least 96%, at least 97%, at least 98%, or at least 99% sequence identity to the amino acid sequence of SEQ ID NO: 10; and/or a light chain variable region comprising the amino acid sequence of SEQ ID NO: 22 or a variant thereof having at least 80%, at least 90%, at least 95%, at least 96%, at least 97%, at least 98%, or at least 99% sequence identity to the amino acid sequence of SEQ ID NO: 22. In some embodiments, the heavy chain variable region comprises the amino acid sequence of SEQ ID NOs: 10; and/or the light chain variable region comprises the amino acid sequence of SEQ ID NO: 22.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 11 or a variant thereof having at least 80%, at least 90%, at least 95%, at least 96%, at least 97%, at least 98%, or at least 99% sequence identity to the amino acid sequence of SEQ ID NO: 11; and/or a light chain variable region comprising the amino acid sequence of SEQ ID NO: 23 or a variant thereof having at least 80%, at least 90%, at least 95%, at least 96%, at least 97%, at least 98%, or at least 99% sequence identity to the amino acid sequence of SEQ ID NO: 23. In some embodiments, the heavy chain variable region comprises the amino acid sequence of SEQ ID NOs: 11; and/or the light chain variable region comprises the amino acid sequence of SEQ ID NO: 23.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 12 or a variant thereof having at least 80%, at least 90%, at least 95%, at least 96%, at least 97%, at least 98%, or at least 99% sequence identity to the amino acid sequence of SEQ ID NO: 12; and/or a light chain variable region comprising the amino acid sequence of SEQ ID NO: 24 or a variant thereof having at least 80%, at least 90%, at least 95%, at least 96%, at least 97%, at least 98%, or at least 99% sequence identity to the amino acid sequence of SEQ ID NO: 24. In some embodiments, the heavy chain variable region comprises the amino acid sequence of SEQ ID NOs: 12; and/or the light chain variable region comprises the amino acid sequence of SEQ ID NO: 24.

In some embodiments, provided herein is an anti-pTau antibody (e.g., an isolated anti-pTau antibody) or antigen-binding moiety thereof comprising a heavy chain variable region comprising the amino acid sequence of SEQ ID NO: 106 or a variant thereof having at least 80%, at least 90%, at least 95%, at least 96%, at least 97%, at least 98%, or at least 99% sequence identity to the amino acid sequence of SEQ ID NO: 106; and/or a light chain variable region comprising the amino acid sequence of SEQ ID NO: 107 or a variant thereof having at least 80%, at least 90%, at least 95%, at least 96%, at least 97%, at least 98%, or at least 99% sequence identity to the amino acid sequence of SEQ ID NO: 107. In some embodiments, the heavy chain variable region comprises the amino acid sequence of SEQ ID NOs: 106; and/or the light chain variable region comprises the amino acid sequence of SEQ ID NO: 107.

In some embodiments, provided herein is an anti-pTau antibody (e.g., an isolated anti-pTau antibody) or antigen-binding moiety thereof comprising the heavy chain CDR1, CDR2, and CDR3 sequences and light chain CDR1, CDR2, and CDR3 sequences according to mAb004, mAb005, mAb008, mAb010, mAb011, mAb013, mAb020, mAb025, mAb032, mAb035, or mAb037 listed in Tables 1 and 2.

In some embodiments, provided herein is an anti-pTau antibody (e.g., an isolated anti-pTau antibody) or antigen-binding moiety thereof comprising the following heavy chain variable ($V_H$) sequences and light chain variable ($V_L$) sequences according to mAb004, mAb005, humanized mAb005, mAb008, mAb010, mAb011, mAb013, mAb020, mAb025, mAb032, mAb035, mAb037, or humanized mAb037 listed in Table 3.

In some embodiments, according to any of the anti-pTau antibodies or antigen-binding moieties described herein, the antibody or antigen-binding moiety is a monoclonal antibody.

In some embodiments, according to any of the anti-pTau antibodies or antigen-binding moieties described herein, the antibody or antigen-binding moiety is a human, humanized, or chimeric antibody.

In some embodiments, according to any of the anti-pTau antibodies or antigen-binding moieties described herein, the antibody or antigen-binding moiety is an antibody fragment, e.g., na Fv, Fab, Fab', scFv, diabody, or F(ab')2 fragment.

In some embodiments, according to any of the anti-pTau antibodies or antigen-binding moieties described herein, the antibody or antigen-binding moiety is a full-length antibody.

In some embodiments, according to any of the anti-pTau antibodies or antigen-binding moieties described herein, the antibody or antigen-binding moiety binds to one or more pathological human Tau species. In some embodiments, the pathological human Tau species is from a tauopathy brain. In some embodiments, the tauphopathy is selected from the group consisting of Alzheimer's disease (AD), primary age-related tauopathy (PART), chronic traumatic encephalopathy (CTE), dementia pugilistica, progressive supranuclear palsy, corticobasal degeneration, frontotemporal dementia, frontotemporal dementias with parkinsonism linked to chromosome 17 (FTDP-17), Lytico-Bodig disease, meningioangiomatosis, postencephalitic parkinsonism, subacute sclerosing pan encephalitis, Pick's Disease, corticobasal degeneration, traumatic brain injury (TBI), argyrophilic grains disease, postencephalic parkinsonism (PEP), parkinsonism dementia complex of Guam (PDCG), tangle-dominant dementia, and globular glial tauopathies (GGTs). In some embodiments, the tauphopathy is selected from the group consisting of Alzheimer's disease (AD), progressive supranuclear palsy (PSP), corticobasal degeneration (CBD), and Pick's disease (PiD).

In some embodiments, the pathological human Tau species is one or more of Tau Type 1A, IB, 11 A, and MB; misordered Tau; mis-disordered Tau; sarkosyl-insoluble Tau; an extracellular Tau deposit; a Tau aggregate; paired helical filaments; a neurofibrillary pathology; and a hyper-phosphorylated form of truncated Tau or full-length Tau. In some embodiments, the pathological human Tau is Tau aggregates and/or abnormally phosphorylated Tau. In some embodiments, the Tau aggregates and/or abnormally phosphorylated Tau is accumulated at synapses of brain. In some embodiments, the Tau aggregates and/or abnormally phosphorylated Tau is accumulated at synapses of tauopathy brain. In some embodiments, the antibody or antigen-binding moiety is capable of discriminating between one or more pathological Tau species and one or more normal Tau species. In some embodiments, the antibody or antigen-binding moiety preferentially binds to Tau species from a tauopathy brain sample (e.g., sample from Alzheimer's disease (AD), progressive supranuclear palsy (PSP), corticobasal degeneration (CBD), or Pick's disease (PiD) brain) as compared to Tau species from a corresponding healthy brain sample. In some embodiments, the antibody or antigen-binding moiety binds fewer normal Tau species from a healthy brain sample as compared to a reference anti-Tau antibody. In some embodiments, the tauopathy brain sample is a tauopathy brain sample. In some embodiments, the tauopathy brain sample is an AD, PSP, CBD, or PiD brain sample. In some embodiments, the brain sample is a whole brain lysate or a frontal cortex lysate, including synaptic fractions and/or sarkosyl-insoluble fractions thereof. In some embodiments, the brain sample is a sarkosyl-insoluble synaptic fraction of a brain lysate.

In some embodiments, according to any of the anti-pTau antibodies or antigen-binding moieties described herein, the antibody or antigen-binding moiety is an IgG1, IgG2, IgG3 or an IgG4 antibody. In some embodiments, the antibody or antigen-binding moiety is an IgG1 or an IgG4 antibody.

In some embodiments, according to any of the anti-pTau antibodies or antigen-binding moieties described herein, the antibody or antigen-binding moiety is capable of inhibiting Tau seeding. In some embodiments, the inhibition after administration of the anti-pTau antibody or antigen-binding moiety described herein is at least 10%, 20%, 30%, 40%, 50%, 60%, 70%, 80%, or 90% higher than after administration of a reference antibody or antigen-binding moiety, as measured by any of the assays known in the art.

In some embodiments, according to any of the anti-pTau antibodies or antigen-binding moieties described herein, the antibody or antigen-binding moiety is capable of inhibiting Tau propagation. In some embodiments, the inhibition after administration of the anti-pTau antibody or antigen-binding moiety described herein is at least 10%, 20%, 30%, 40%, 50%, 60%, 70%, 80%, or 90% higher than after administration of a reference antibody or antigen-binding moiety, as measured by any of the assays known in the art.

Antibody Affinity

In certain embodiments, an anti-pTau antibody or antigen-binding moiety provided herein has a dissociation constant (KD) of ≤1 µM, <100 nM, <10 nM, <1 nM, <0.1 nM, <0.01 nM, or <0.001 nM. KD can be measured using any technique known in the art, e.g., by surface plasmon resonance (SPR), radioimmunoassay (RIA), or Kinetic Exclusion Assay (KinExA®).

In some embodiments, the anti-pTau antibody or antigen-binding moiety has a binding affinity with an $EC_{50}$ value of between $1\times10^{-11}$ M and $1\times10^{-10}$ M to AD brain homogenate. In some embodiments, the anti-pTau antibody or antigen-binding moiety has a binding affinity with an $EC_{50}$ value of between $1\times10^{-10}$ M and $1\times10^{-9}$ M to AD brain homogenate. In some embodiments, the anti-pTau antibody or antigen-binding moiety has a binding affinity with an $EC_{50}$ value of between $1\times10^{-9}$ M and $1\times10^{-8}$ M to AD brain homogenate.

Humanized Antibodies

A non-human antibody may be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., Nature 332:323-329 (1988); Queen et al., Proc. Nat'l Acad. Sci. USA 86: 10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13: 1619-1633 (2008)); and framework regions derived from screening FR libraries (see, e.g., Baca et al., J. Biol. Chem. 272: 10678-10684 (1997) and Rosok et al., J. Biol. Chem. 271: 22611-22618 (1996)).

In some embodiments, provided herein is a humanized anti-pTau antibody (e.g., an isolated anti-pTau antibody) or antigen-binding moiety thereof that is a humanized mAb004, mAb005, mAb008, mAb010, mAb011, mAb013, mAb020, mAb025, mAb032, mAb035, or mAb037. In some embodiments, the humanized anti-pTau antibody is a humanized mAb005. In some embodiments, the humanized anti-pTau antibody is a humanized mAb037.

Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. Methods in Molecular Biology 178: 1-37 (O'Brien et al, ed., Human Press, Totowa, N.J., 2001) and further described, e.g., in the McCafferty et al., Nature 348:552-554; Clackson et al, Nature 352: 624-628 (1991); Marks et al., J. Mol. Biol. 222: 581-597 (1992); Marks and Bradbury, m Methods in Molecular Biology 248: 161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101 (34): 12467-12472 (2004); and Lee et al., J. Immunol. Methods 284(1-2): 1 19-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol, 227: 381-388 (1992). Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Tau and the other is for any other antigen. In certain embodiments, one of the binding specificities is for Tau and the other is for amyloid beta. In certain embodiments, bispecific antibodies may bind to two different epitopes of Tau. Bispecific antibodies may also be used to localize cytotoxic agents to cells which express Tau. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004 A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol, 148(5): 1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol, 152:5368 (1994)); and preparing trispecific antibodies as described, e.g., in Tutt et al. J. Immunol. 147: 60 (1991).

Antibody Variants

In certain embodiments, amino acid sequence variants of the antibodies provided herein are contemplated. For example, it may be desirable to improve the binding affinity and/or other biological properties of the antibody, Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions, such as conservative substitutions, are provided. Sites of interest for substitutional mutagenesis include the HVRs and FRs. Amino acid substitutions may be introduced into an antibody of interest and the products screened for a desired activity, e.g., retained/improved antigen binding, decreased immunogenicity, or improved ADCC or CDC.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207: 179-196 (2008)), and/or residues that contact antigen, with the resulting variant VH or VL being tested for binding affinity. Affinity maturation by constructing and reselecting from secondary libraries has been described, e.g., in Hoogenboom et al. Methods in Molecular Biology 178: 1-37 (O'Brien et al., ed., Human Press, Totowa, N.J., (2001) .) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244: 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., U.S. Patent Publication Nos. U.S. 2003/0157108 (Presta, L.); U.S. 2004/0093621 (Kyowa Hakko Kogyo Co., Ltd). Examples of publications related to "defucosylated" or "fucose-deficient" antibody variants include: U.S. 2003/0157108; WO 2000/61739; WO 2001/29246; US 2003/0115614; U.S. 2002/0164328; U.S. 2004/0093621; U.S. 2004/0132140; U.S. 2004/0110704; U.S. 2004/0110282; U.S. 2004/0109865; WO 2003/085119; WO 2003/084570; WO 2005/035586; WO 2005/035778; WO2005/053742; WO2002/031140; Okazaki et al. J. Mol. Biol. 336: 1239-1249 (2004); Yamane-Ohnuki et al. Biotech. Bioeng. 87: 614 (2004). Examples of cell lines capable of producing defucosylated antibodies include Led 3 CHO cells deficient in protein fucosylation (Ripka et al. Arch. Biochem. Biophys. 249:533-545 (1986); U.S. Publication No. 2003/0157108 A1, Presta, L.; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4): 680-688 (2006); and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and U.S. Publication No. 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FCYRIII. FCR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I. et al., Proc. Nat'l Acad. Sci. USA 82: 1499-1502 (1985); 5,821,337 (see Bruggemann, M. et al., J. Exp. Med. 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al., J. Immunol. Methods 202: 163 (1996); Cragg, M. S. et al., Blood 101: 1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001)).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in U.S. Publication No. 2005/0014934 A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371, 826).

See also Duncan & Winter, Nature 322:738-40 (1988); U.S. Pat. Nos. 5,648,260; 5,624,821; and WO 94/29351 concerning other examples of Fc region variants.

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A1 1 8 (EU numbering) of the heavy chain; and S400 (EU numbering) of the heavy chain Fc region. Cysteine engineered antibodies may be generated as described, e.g., in U.S. Pat. No. 7,521,541.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1, 3, 6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof.

Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In some embodiments, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Assays

Anti-Tau antibodies and antigen-binding moieties provided herein may be identified, screened for, and/or characterized for their physical/chemical properties and/or biological activities by various assays known in the art.

In one aspect, an antibody or antigen-binding moiety of the invention is tested for its antigen-binding activity, e.g., by known methods such as ELISA, western blot, etc.

In another aspect, competition assays may be used to identify an antibody or antigen-binding moiety that competes with an antibody or antigen-binding moiety described herein for binding to Tau. Detailed exemplary methods for mapping an epitope to which an antibody binds are provided in Morris (1996) "Epitope Mapping Protocols," Methods in Molecular Biology vol. 66 (Humana Press, Totowa, N.J.).

In an exemplary competition assay, an immobilized Tau species (e.g., a pathological Tau species) is incubated in a solution comprising a first labeled antibody that binds to the Tau species (e.g., any antibody described herein, such as mAb005 and mAb037) and a second unlabeled antibody that is being tested for its ability to compete with the first antibody for binding to the Tau species. The second antibody may be present in a hybridoma supernatant. As a control, the immobilized Tau species is incubated in a solution comprising the first labeled antibody but not the second unlabeled antibody. After incubation under conditions permissive for binding of the first antibody to the Tau species, excess unbound antibody is removed, and the amount of label associated with the immobilized Tau species is measured. If the amount of label associated with the immobilized Tau species is substantially reduced in the test sample relative to the control sample, then that indicates that the second antibody is competing with the first antibody for binding to the Tau species. See Harlow and Lane (1988) Antibodies: A Laboratory Manual ch. 14 (Cold Spring Harbor Laboratory, Cold Spring Harbor, N.Y.).

In one aspect, assays are provided for identifying anti-Tau antibodies having biological activity. Biological activity may include, e.g., binding of such antibodies to multiple forms of Tau (e.g., monomeric Tau, oligomeric Tau, non-phosphorylated Tau, and phosphorylated Tau) and reducing the level of Tau protein (e.g., total Tau, total soluble Tau, soluble non-phosphorylated Tau, soluble phosphorylated Tau, total insoluble Tau, insoluble non-phosphorylated Tau, insoluble phosphorylated Tau, hyperphosphorylated Tau, or paired helical filaments containing hyperphosphorylated Tau, in the brain, e.g., in the brain synapses, cortex and/or hippocampus).

In certain embodiments, an antibody of the invention is tested for such biological activity. For example, an animal model of tauopathy, such as a Tau transgenic mouse (e.g., P301L), can be used to detect binding of anti-Tau antibodies to brain sections, and for example, to pathological Tau species (e.g., neurofibrillary tangles) in the brains of the transgenic mice. Further, an animal model of tauopathy, such as a Tau transgenic mouse (e.g., P301L), can be treated with anti-Tau antibodies and experimental techniques known in the art can be used to assess whether such treatment reduces the level of Tau protein (e.g., total Tau, total soluble Tau, soluble phosphorylated Tau, soluble non-phosphorylated Tau, total insoluble Tau, insoluble phosphorylated Tau, insoluble non-phosphorylated Tau, hyperphosphorylated Tau, or paired helical filaments containing hyperphosphorylated Tau) in the mouse brain (e.g., in the brain cortex and/or hippocampus).

Immunoconjugates

The invention also provides immunoconjugates comprising an anti-Tau antibody herein conjugated to one or more other therapeutic agents or radioactive isotopes.

In some embodiments, an immunoconjugate comprises an antibody or antigen-binding moiety as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody or antigen-binding moiety may be made using a variety of functional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), Afunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldi ethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52: 127-131 (1992); U.S. Pat. No. 5,208,020) may be used.

The immunuoconjugates herein expressly contemplate, but are not limited to, such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinyl sulfone) benzoate) which are commercially available (e.g., from Pierce Biotechnology, Inc., Rockford, Ill., U.S.A.).

Nucleic Acids

In another aspect, provided herein is nucleic acid encoding an anti-pTau antibody or antigen-binding moiety according to any of the embodiments described herein. In some embodiments, such nucleic acid is a vector (e.g., a recombinant expression vector).

In some embodiments, provided herein is nucleic acid encoding an anti-pTau antibody or antigen-binding moiety thereof, wherein the anti-pTau antibody or antigen-binding moiety comprises a) a heavy chain variable region comprising i) a CDR1 comprising the amino acid sequence of any one of SEQ ID NOs: 49-59 or a variant thereof having at least 80%, at least 90%, or at least 95% sequence identity to the amino acid sequence of any one of SEQ ID NOs: 49-59; ii) a CDR2 comprising the amino acid sequence of any one of SEQ ID NOs: 60-70 or a variant thereof having at least 80%, at least 90%, or at least 95% sequence identity to the amino acid sequence of any one of SEQ ID NOs: 60-70; and/or iii) a CDR3 comprising the amino acid sequence of any one of SEQ ID NOs: 71-81 or a variant thereof having at least 80%, at least 90%, or at least 95% sequence identity to the amino acid sequence of any one of SEQ ID NOs: 71-81; and/or b) a light chain variable region comprising iv) a CDR1 comprising the amino acid sequence of any one of SEQ ID NOs: 82-90 or a variant thereof having at least 80%, at least 90%, or at least 95% sequence identity to the amino acid sequence of any one of SEQ ID NOs: 82-90; v) a CDR2 comprising the amino acid sequence of any one of SEQ ID NOs: 91-95 or a variant thereof having at least 80%, at least 90%, or at least 95% sequence identity to the amino acid sequence of any one of SEQ ID NOs: 91-95; and/or vi) a CDR3 comprising the amino acid sequence of any one of SEQ ID NOs: 96-105 or a variant thereof having at least 80%, at least 90%, or at least 95% sequence identity to the amino acid sequence of any one of SEQ ID NOS: 96-105. In some embodiments, the heavy chain and/or light chain CDR sequences are as indicated for a given antibody clone shown in Tables 1 and 2. In some embodiments, the heavy chain variable region and the light chain variable region are encoded in the same nucleic acid molecule. In some embodiments, the heavy chain variable region and the light chain variable region are encoded in different nucleic acid molecules. In some embodiments, the heavy chain and the light chain are encoded in the same nucleic acid molecule. In some embodiments, the heavy chain and the light chain are encoded in different nucleic acid molecules.

In some embodiments, provided herein is nucleic acid encoding an anti-pTau antibody or antigen-binding moiety thereof comprising a heavy chain variable region comprising the amino acid sequence of any one of SEQ ID NOs: 1-12 and 106 or a variant thereof having at least 80%, at least 90%, at least 95%, at least 96%, at least 97%, at least 98%, or at least 99% sequence identity to the amino acid sequence of any one of SEQ ID NOs: 1-12 and 106; and/or a light chain variable region comprising the amino acid sequence of any one of SEQ ID NOs: 13-24 and 107 or a variant thereof having at least 80%, at least 90%, at least 95%, at least 96%, at least 97%, at least 98%, or at least 99% sequence identity to the amino acid sequence of any one of SEQ ID NOs: 13-24 and 107. In some embodiments, the heavy chain variable region comprises the amino acid sequence of any one of SEQ ID NOs: 1-12 and 106; and/or the light chain variable region comprises the amino acid sequence of any one of SEQ ID NOs: 13-24 and 107. In some embodiments, the heavy chain and light chain variable regions are as indicated for a given antibody clone shown in Table 3. In some embodiments, the heavy chain variable region and the light chain variable region are encoded in the same nucleic acid molecule. In some embodiments, the heavy chain variable region and the light chain variable region are encoded in different nucleic acid molecules. In some embodiments, the heavy chain and the light chain are encoded in the same nucleic acid molecule. In some embodiments, the heavy chain and the light chain are encoded in different nucleic acid molecules.

In some embodiments, provided herein is nucleic acid encoding an anti-pTau antibody or antigen-binding moiety thereof, wherein the nucleic acid comprises a first coding sequence encoding a heavy chain variable region, wherein the first coding sequence comprises the nucleotide sequence of any one of SEQ ID NOs: 25-36 and 108 or a variant thereof having at least 80%, at least 90%, at least 95%, at least 96%, at least 97%, at least 98%, or at least 99% sequence identity to the nucleotide sequence of any one of SEQ ID NOs: 25-36 and 108; and/or a second coding sequence encoding a light chain variable region, wherein the second coding sequence comprises the nucleotide sequence of any one of SEQ ID NOs: 37-48 and 109 or a variant thereof having at least 80%, at least 90%, at least 95%, at least 96%, at least 97%, at least 98%, or at least 99% sequence identity to the nucleotide sequence of any one of SEQ ID NOs: 37-48 and 109. In some embodiments, the first coding sequence comprises the nucleotide sequence of any one of SEQ ID NOs: 25-36 and 108; and/or the second coding sequence comprises the nucleotide sequence of any one of SEQ ID NOs: 37-48 and 109. In some embodiments, the heavy chain variable region and the light chain variable region are encoded in the same nucleic acid molecule. In some embodiments, the heavy chain variable region and the light chain variable region are encoded in different nucleic acid molecules. In some embodiments, the heavy chain and the light chain are encoded in the same nucleic acid molecule. In some embodiments, the heavy chain and the light chain are encoded in different nucleic acid molecules.

In some embodiments, provided herein nucleic acid encoding an anti-pTau antibody or antigen-binding moiety thereof, wherein the nucleic acid comprises a first coding sequence encoding a heavy chain variable region, and a second coding sequence encoding a light chain variable region, wherein the heavy chain variable region and the light chain variable region is any one of mAb004, mAb005, humanized mAb005, mAb008, mAb010, mAb011, mAb013, mAb020, mAb025, mAb032, mAb033, mAb037, or humanized mAb037.

In some embodiments, according to any nucleic acid encoding an anti-pTau antibody or antigen-binding moiety described herein, the nucleic acid is a vector. In some embodiments, the heavy chain variable region and the light chain variable region are encoded in the same vector. In some embodiments, the heavy chain variable region and the light chain variable region are encoded in different vectors. In some embodiments, the heavy chain and the light chain are encoded in the same vector. In some embodiments, the heavy chain and the light chain are encoded in different vectors.

In some embodiments, the vector is an expression vector for expression of the anti-pTau antibody or antigen-binding moiety in a host cell. Expression vectors contemplated include, but are not limited to, viral vectors based on vaccinia virus, poliovirus, adenovirus, AAV, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors can be used so long as they are compatible with the host cell.

In some embodiments, a vector according to any of the embodiments described herein comprises one or more transcription and/or translation control elements. Depending on the host/vector system utilized, any of a number of suitable transcription and translation control elements, including constitutive and inducible promoters, transcription enhancer elements, transcription terminators, etc. can be used in the expression vector.

In some embodiments, a vector according to any of the embodiments described herein comprises a ribosome binding site for translation initiation and a transcription terminator. In some embodiments, the vector comprises appropriate sequences for amplifying expression. In some embodiments, the vector comprises nucleotide sequences encoding non-native tags (e.g., histidine tags, hemagglutinin tags, green fluorescent proteins, etc.) that are fused to nucleotide sequences encoding a polypeptide of interest (e.g., an antigen-binding construct), thus allowing for expression of fusion proteins comprising the tags.

In some embodiments, according to any of the vectors described herein comprising a promoter, the promoter is an inducible promoter (e.g., a heat shock promoter, tetracycline-regulated promoter, steroid-regulated promoter, metal-regulated promoter, estrogen receptor-regulated promoter, etc.) or a constitutive promoter (e.g., CMV promoter, UBC promoter, etc.). In some embodiments, the promoter is a spatially restricted and/or temporally restricted promoter (e.g., a tissue specific promoter, a cell type specific promoter, etc.).

Codon-Optimization

In some embodiments, nucleic acid encoding an anti-pTau antibody or antigen-binding moiety as described herein is codon-optimized, e.g., codon-optimized based on specific host cells in which the anti-pTau antibody or antigen-binding moiety is to be expressed. It will be appreciated by the skilled artisan that any nucleotide sequence of the present disclosure can be codon optimized for expression in any species of interest. Codon optimization is well known in the art and involves modification of a nucleotide sequence for codon usage bias using species-specific codon usage tables. Codon usage tables can be generated based on a sequence analysis of the most highly expressed genes for the species of interest. The modifications of the nucleotide sequences can be determined by comparing a species specific codon usage table with the codons present in the native polynucleotide sequences.

Strategies and methodologies for codon optimization are known in the art and are available for various systems. In some embodiments, a nucleic acid described herein is codon-optimized for increased expression in a host cell.

As is well understood in the art, codon optimization of a nucleotide sequence results in a nucleotide sequence having less than 100% identity (e.g., less than 70%, 71%. 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) to the native nucleotide sequence, but which still encodes a polypeptide having the same function as that encoded by the original, native nucleotide sequence.

Host Cells

In another aspect, provided herein is a host cell comprising or capable of expressing an anti-pTau antibody or antigen-binding moiety according to any of the embodiments described herein. In some embodiments, the host cell comprises nucleic acid (e.g., a vector) encoding an anti-pTau antibody or antigen-binding moiety as described herein, such as heterologous nucleic acid. In some embodiments, the host cell is eukaryotic, e.g., a Chinese Hamster Ovary (CHO) cell or lymphoid cell (e.g., Y0, NS0, Sp20 cell).

Suitable host cells for cloning or expression of vectors encoding an anti-pTau antibody or antigen-binding moiety include prokaryotic and eukaryotic cells. For example, antibodies or antigen-binding moieties thereof may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B.K.C. Lo, ed., Humana Press, Totowa, N.J., 2003), pp. 245-254, describing expression of antibody fragments in *E. coli*). After expression, the antibody or antigen-binding moiety may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22: 1409-1414 (2004), and Li et al., Nat. Biotech. 24:210-215 (2006).

Suitable host cells for the expression of glycosylated antibody may also be derived from multicellular organisms. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Examples of useful mammalian host cell lines include monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse Sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3 A); human lung cells (W138); human liver cells (Hep G2); mouse mammary tumor (MMT 060562); TRI cells, as described, e.g., in Mather et al., Annals N. Y. Acad. Sci. 383:44-68 (1982); MRC 5 cells; and FS4 cells. Other useful mammalian host cell lines include Chinese hamster ovary (CHO) cells, including DHFR" CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In some embodiments, provided herein is a host cell comprising nucleic acid encoding an anti-pTau antibody or antigen-binding moiety, wherein the anti-pTau antibody or antigen-binding moiety comprises a) a heavy chain variable region comprising i) a CDR1 comprising the amino acid sequence of any one of SEQ ID NOs: 49-59 or a variant thereof having at least 80%, at least 90%, or at least 95% sequence identity to the amino acid sequence of any one of SEQ ID NOs: 49-59; ii) a CDR2 comprising the amino acid sequence of any one of SEQ ID NOs: 60-70 or a variant thereof having at least 80%, at least 90%, or at least 95% sequence identity to the amino acid sequence of any one of SEQ ID NOs: 60-70; and/or iii) a CDR3 comprising the amino acid sequence of any one of SEQ ID NOs: 71-81 or a variant thereof having at least 80%, at least 90%, or at least 95% sequence identity to the amino acid sequence of any one of SEQ ID NOs: 71-81; and/or b) a light chain variable region comprising iv) a CDR1 comprising the amino acid sequence of any one of SEQ ID NOs: 82-90 or a variant thereof having at least 80%, at least 90%, or at least 95% sequence identity to the amino acid sequence of any one of SEQ ID NOs: 82-90; v) a CDR2 comprising the amino acid sequence of any one of SEQ ID NOs: 91-95 or a variant thereof having at least 80%, at least 90%, or at least 95% sequence identity to the amino acid sequence of any one of SEQ ID NOs: 91-95; and/or vi) a CDR3 comprising the amino acid sequence of any one of SEQ ID NOs: 96-105 or a variant thereof having at least 80%, at least 90%, or at least 95% sequence identity to the amino acid sequence of any one of SEQ ID NOS: 96-105. In some embodiments, the heavy chain and/or light chain CDR sequences are as indicated for a given antibody clone shown in Tables 1 and 2. In some embodiments, the heavy chain variable region and the light chain variable region are produced in the same host cell. In some embodiments, the heavy chain variable region and the light chain variable region are produced in different host cells. In some embodiments, the heavy chain and the light chain are produced in the same host cell. In some embodiments, the heavy chain and the light chain are produced in different host cells.

In some embodiments, provided herein is a host cell comprising nucleic acid encoding an anti-pTau antibody or antigen-binding moiety, wherein the anti-pTau antibody or antigen-binding moiety comprises a heavy chain variable region comprising the amino acid sequence of any one of SEQ ID NOs: 1-12 and 106 or a variant thereof having at least 80%, at least 90%, at least 95%, at least 96%, at least 97%, at least 98%, or at least 99% sequence identity to the amino acid sequence of any one of SEQ ID NOs: 1-12 and 106; and/or a light chain variable region comprising the amino acid sequence of any one of SEQ ID NOs: 13-24 and 107 or a variant thereof having at least 80%, at least 90%, at least 95%, at least 96%, at least 97%, at least 98%, or at least 99% sequence identity to the amino acid sequence of any one of SEQ ID NOs: 13-24 and 107. In some embodiments, the heavy chain variable region comprises the amino acid sequence of any one of SEQ ID NOs: 1-12 and 106; and/or the light chain variable region comprises the amino acid sequence of any one of SEQ ID NOs: 13-24 and 107. In some embodiments, the heavy chain and light chain variable regions are as indicated for a given antibody clone shown in Table 3. In some embodiments, the heavy chain variable region and the light chain variable region are produced in the same host cell. In some embodiments, the heavy chain variable region and the light chain variable region are produced in different host cells. In some embodiments, the heavy chain and the light chain are produced in the same host cell. In some embodiments, the heavy chain and the light chain are produced in different host cells.

In some embodiments, provided herein is a host cell comprising nucleic acid encoding an anti-pTau antibody or antigen-binding moiety, wherein the nucleic acid comprises a first coding sequence encoding a heavy chain variable region, wherein the first coding sequence comprises the nucleotide sequence of any one of SEQ ID NOs: 25-36 and 108 or a variant thereof having at least 80%, at least 90%, at least 95%, at least 96%, at least 97%, at least 98%, or at least 99% sequence identity to the nucleotide sequence of any one of SEQ ID NOs: 25-36 and 108; and/or a second coding sequence encoding a light chain variable region, wherein the second coding sequence comprises the nucleotide sequence of any one of SEQ ID NOs: 37-48 and 109 or a variant thereof having at least 80%, at least 90%, at least 95%, at least 96%, at least 97%, at least 98%, or at least 99% sequence identity to the nucleotide sequence of any one of SEQ ID NOs: 37-48 and 109. In some embodiments, the first coding sequence comprises the nucleotide sequence of any one of SEQ ID NOs: 25-36 and 108; and/or the second coding sequence comprises the nucleotide sequence of any one of SEQ ID NOs: 37-48 and 109. In some embodiments, the heavy chain variable region and the light chain variable region are produced in the same host cell. In some embodiments, the heavy chain variable region and the light chain variable region are produced in different host cells. In some embodiments, the heavy chain and the light chain are produced in the same host cell. In some embodiments, the heavy chain and the light chain are produced in different host cells.

Nucleic acids and vectors as described herein may be provided to the cells using well-developed transfection techniques; see, e.g., Angel, M. et al. (2010). *PLoS ONE,* 5(7):e11756, and the commercially available TransMessenger® reagents from Qiagen, Stemfect™ RNA Transfection Kit from Stemgent, and TransiT®-mRNA Transfection Kit from Mims Bio. See also Beumer, K. J. et al. (2008). *Proc. Natl. Acad. Sci. USA,* 105(50):19821-19826. Many vectors, e.g., plasmids, cosmids, minicircles, phage, viruses, etc., useful for transferring nucleic acids into host cells are available. The vectors comprising the nucleic acid(s) may be maintained episomally, e.g., as plasmids, minicircle DNAs, viruses such cytomegalovirus, adenovirus, etc., or they may be integrated into the host cell genome, through homologous recombination or random integration, e.g., retrovirus-derived vectors such as MMLV, HIV-1, ALV, etc.

Vectors may be provided directly to the cells. In other words, the cells are contacted with vectors such that the vectors are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising nucleic acid as described herein. Retroviruses, for example, lentiviruses, are particularly suitable to the method of the present disclosure. Commonly used retroviral vectors are "defective", e.g., unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also be introduced by direct micro-injection (e.g., injection of RNA into a zebrafish embryo).

Vectors will generally comprise suitable promoters for driving the expression, that is, transcriptional activation, of the nucleic acid of interest. In other words, the nucleic acid of interest will be operably linked to a promoter. This may include ubiquitously active promoters, for example, the CMV-13-actin promoter, or inducible promoters, such as promoters that are active in particular cell populations or that respond to the presence of drugs such as tetracycline. By transcriptional activation, it is intended that transcription will be increased above basal levels in the host cell by at least about 10-fold (such as by at least about any of 100-fold, 1000-fold, or greater). In addition, vectors may include nucleic acid sequences that code for selectable markers in the host cells.

Methods of the Disclosure
Methods of Preparing an Anti-pTau Antibody or Antigen-Binding Moiety Antibodies and antigen-binding moieties thereof as described herein may be produced using recombinant methods and compositions, e.g., as described in U.S. Pat. No. 4,816,567. In some embodiments, the methods employ nucleic acid encoding an anti-pTau antibody or antigen-binding moiety described herein. In some embodiments, the nucleic acid is one or more vectors (e.g., expression vectors). In some embodiments, a host cell comprising such nucleic acid is employed. In one such embodiment, the host cell comprises (e.g., has been transformed with): (1) a vector comprising nucleic acid encoding an amino acid sequence comprising a light chain variable region of the anti-pTau antibody or antigen-binding moiety and an amino acid sequence comprising the heavy chain variable region of the anti-pTau antibody or antigen-binding moiety, or (2) a first vector comprising nucleic acid encoding an amino acid sequence comprising the light chain variable region of the anti-pTau antibody or antigen-binding moiety and a second vector comprising nucleic acid encoding an amino acid sequence comprising the heavy chain variable region of the anti-pTau antibody or antigen-binding moiety. In some embodiments, the host cell is eukaryotic, e.g. a Chinese Hamster Ovary (CHO) cell or lymphoid cell (e.g., Y0, NS0, Sp20 cell). In some embodiments, a method of preparing an anti-pTau antibody or antigen-binding moiety is provided, wherein the method comprises culturing a host cell comprising nucleic acid encoding the anti-pTau antibody or antigen-binding moiety, as provided herein, under conditions suitable for expression of the anti-pTau antibody or antigen-binding moiety, and optionally recovering the anti-pTau antibody or antigen-binding moiety from the host cell (or host cell culture medium).

For recombinant production of an anti-pTau antibody or antigen-binding moiety, nucleic acid encoding the anti-pTau antibody or antigen-binding moiety, e.g., as described herein, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

In another aspect, provided herein are anti-pTau antibodies or antigen-binding moieties prepared according to any of the methods described herein.

Methods of Detecting Pathological Tau

In certain embodiments, any of the anti-pTau antibodies provided herein is useful for detecting the presence of one or more pathological Tau species in a biological sample. The term "detecting" as used herein encompasses quantitative or qualitative detection. In certain embodiments, a biological sample comprises a cell or tissue, such as cerebrospinal fluid, a cell or tissue of the brain (e.g., brain cortex or hippocampus), or blood. In some embodiments, a biological sample is cerebrospinal fluid.

In some embodiments, an anti-pTau antibody for use in a method of diagnosis or detection is provided. In a further aspect, a method of detecting the presence of one or more pathological Tau species in a biological sample is provided. In certain embodiments, the method comprises contacting the biological sample with an anti-pTau antibody as described herein under conditions permissive for binding of the anti-pTau antibody to the one or more pathological Tau species, and detecting whether a complex is formed between the anti-pTau antibody and the one or more pathological Tau species. Such method may be an in vitro or in vivo method. Further, the complex formed between the anti-pTau antibody and the one or more pathological Tau species in a test biological sample can be compared to the complex formed in a control biological sample (e.g., a biological sample from a healthy subject or subjects). The amount of the complex formed between the anti-pTau antibody and the one or more pathological Tau species in a test biological sample can also be quantified and compared to the amount of the complex formed in a control biological sample (e.g., a biological sample from a healthy subject or subjects) or to the average amount of the complex known to be formed in healthy subjects.

In some embodiments, an anti-pTau antibody is used to select subjects eligible for therapy with an anti-pTau antibody, e.g. where one or more pathological Tau species is a biomarker for selection of patients. For example, in some embodiments, an anti-pTau antibody is used to detect whether the subject has a Tau protein disease or disorder, or whether the subject is at high risk (or predisposed to) a Tau protein disease or disorder.

In some embodiments, the one or more pathological Tau species are selected from Tau Type 1A, IB, 11 A, and MB; misordered Tau; mis-disordered Tau; sarkosyl-insoluble Tau; an extracellular Tau deposit; a Tau aggregate; paired helical filaments; a neurofibrillary pathology; and a hyperphosphorylated form of truncated Tau or full-length Tau. In some embodiments, the one or more pathological Tau species includes hyperphosphorylated and sarkosyl-insoluble Tau.

Exemplary diseases or disorders that may be diagnosed using an antibody of the invention include Tau protein-associated diseases or disorders, and diseases or disorders caused by or associated with the formation of one or more pathological Tau species. In some embodiments, diseases or disorders that may be diagnosed using an antibody of the invention include Tau protein associated diseases or disorders that are manifested in an impairment or loss of cognitive functions including reasoning, situational judgement, memory capacity, learning, and/or special navigation. In particular, diseases or disorders that may be diagnosed using an antibody of the invention include tauopathies such as neurodegenerative tauopathies. Exemplary diseases or disorders that may be diagnosed using an antibody of the invention include, but are not limited to, Alzheimer's Disease (AD), primary age-related tauopathy (PART), chronic traumatic encephalopathy (CTE), dementia pugilistica, progressive supranuclear palsy, corticobasal degeneration, frontotemporal dementia, frontotemporal dementias with parkinsonism linked to chromosome 17 (FTDP-17), Lytico-Bodig disease, meningioangiomatosis, postencephalitic parkinsonism, subacute sclerosing pan encephalitis, Pick's Disease, corticobasal degeneration, traumatic brain injury (TBI), argyrophilic grains disease, postencephalic parkinsonism (PEP), parkinsonism dementia complex of Guam (PDCG), tangle-dominant dementia, and globular glial tauopathies (GGTs).

In certain embodiments, labeled anti-pTau antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Methods of Treating Tau Protein Associated Disease

In some aspects of the disclosure, an anti-pTau antibody or antigen-binding moiety according to any of the embodiments described herein is employed for purposes of treating or preventing a Tau-associated neurodegenerative disease in a subject. In some embodiments, the disease is a tauopathy. In some embodiments, the tauopathy is a neurodegenerative tauopathy. In some embodiments, the tauopathy is Alzheimer's Disease (AD), primary age-related tauopathy (PART), chronic traumatic encephalopathy (CTE), dementia pugilistica, progressive supranuclear palsy, corticobasal degeneration, frontotemporal dementia, frontotemporal dementias with parkinsonism linked to chromosome 17 (FTDP-17), Lytico-Bodig disease, meningioangiomatosis, postencephalitic parkinsonism, subacute sclerosing pan encephalitis, Pick's Disease, corticobasal degeneration, traumatic brain injury (TBI), argyrophilic grains disease, postencephalic parkinsonism (PEP), parkinsonism dementia complex of Guam (PDCG), tangle-dominant dementia, or globular glial tauopathies (GGTs). The anti-pTau antibody or antigen-binding moiety can be incorporated into a variety of formulations, including those comprising the anti-pTau antibody or antigen-binding moiety, nucleic acid encoding the anti-pTau antibody or antigen-binding moiety, and/or host cells capable of expressing the anti-pTau antibody or antigen-binding moiety. More particularly, the anti-pTau antibody or antigen-binding moiety can be formulated into pharmaceutical compositions by combination with appropriate pharmaceutically acceptable carriers or diluents. In some embodiments, administration of the anti-pTau antibody or antigen-binding moiety to the subject has one or more of the following effects: retention or increase of cognitive memory capacity, slowing of memory loss, reduction in the level of Tau protein, inhibition of the propagation of Tau aggregation, and inhibition of Tau seeding. In some embodiments, administration of the anti-pTau antibody or antigen-binding moiety to the subject has one or more of the following effects: retention or increase of cognitive memory capacity, slowing of memory loss, reduction in the level of Tau protein, inhibition of the propagation of Tau aggregation, and inhibition of Tau seeding. In some embodiments, the change in effect after administration is at least 10%, 20%, 30%, 40%, 50%, 60%, 70%, 80%, or 90% lower than before administration of the anti-pTau antibody or antigen-binding moiety, as measured by assays known in the art. In some embodiments, the change in effect after administration is at least 10%, 20%, 30%, 40%, 50%, 60%, 70%, 80%, or 90% higher than before administration of the anti-pTau antibody or antigen-binding moiety, as measured by assays known in the art.

In some embodiments, provided herein is a method of treating or preventing a tauopathy in a subject in need thereof, the method comprising administering to the subject an anti-pTau antibody or antigen-binding moiety according to any of the embodiments described herein. In some embodiments, administration of the anti-pTau antibody or antigen-binding moiety to the subject has one or more of the following effects: retention or increase of cognitive memory capacity, slowing of memory loss, reduction in the level of Tau aggregates, inhibition of the propagation of Tau aggregation, and inhibition of Tau seeding. In some embodiments, administration of the anti-pTau antibody or antigen-binding moiety to the subject has one or more of the following effects: retention or increase of cognitive memory capacity, slowing of memory loss, reduction in the level of Tau protein aggregates, inhibition of the propagation of Tau aggregation, and inhibition of Tau seeding. In some embodiments, the change in effect after administration is at least 10%, 20%, 30%, 40%, 50%, 60%, 70%, 80%, or 90% lower than before administration of the anti-pTau antibody or antigen-binding moiety, as measured by assays known in the art. In some embodiments, the change in effect after administration is at least 10%, 20%, 30%, 40%, 50%, 60%, 70%, 80%, or 90% higher than before administration of the anti-pTau antibody or antigen-binding moiety, as measured by assays known in the art.

In some embodiments, provided herein is a method of retaining or increasing cognitive memory capacity or slowing memory loss in a subject having or at risk of developing a Tau-associated neurodegenerative disease, the method comprising administering to the subject an anti-pTau antibody or antigen-binding moiety according to any of the embodiments described herein.

In some embodiments, provided herein is a method of reducing the level of Tau aggregates in a subject having or at risk of developing a Tau-associated neurodegenerative disease, the method comprising administering to the subject an anti-pTau antibody or antigen-binding moiety according to any of the embodiments described herein. In some embodiments, the level of Tau aggregates (such as abnormally phosphorylated Tau) is reduced in the subject as compared to their levels in the subject prior to administration of the antibody or antigen-binding moiety. In some embodiments, the Tau aggregates and/or abnormally phosphorylated Tau proteins are accumulated at synapses of brain. In some embodiments, the Tau aggregates and/or abnormally phosphorylated Tau proteins are accumulated at synapses of tauopathy brain. In some embodiments, the level of a pathological Tau species is reduced in the subject as compared to its level in the subject prior to administration of the antibody or antigen-binding moiety. In some embodiments, the Tau aggregates and/or abnormally phosphorylated Tau proteins are accumulated at synapses of brain. In some embodiments, the Tau aggregates and/or abnormally phosphorylated Tau proteins are accumulated at synapses of tauopathy brain. In some embodiments, the level of a pathological Tau species is reduced in the subject as compared to its level in the subject prior to administration of the antibody or antigen-binding moiety. In some embodiments, the change in effect after administration is at least 10%, 20%, 30%, 40%, 50%, 60%, 70%, 80%, or 90% lower than before administration of the anti-pTau antibody or antigen-binding moiety, as measured by assays known in the art.

In some embodiments, provided herein is a method of inhibiting the propagation of Tau aggregation in a subject having or at risk of developing a Tau-associated neurodegenerative disease, the method comprising administering to the subject an anti-pTau antibody or antigen-binding moiety according to any of the embodiments described herein. In some embodiments, the change in effect after administration is at least 10%, 20%, 30%, 40%, 50%, 60%, 70%, 80%, or 90% lower than before administration of the anti-pTau antibody or antigen-binding moiety, as measured by assays known in the art.

In some embodiments, provided herein is a method of inhibiting Tau seeding in a subject having or at risk of developing a Tau-associated neurodegenerative disease, the method comprising administering to the subject an anti-pTau antibody or antigen-binding moiety according to any of the embodiments described herein. In some embodiments, the change in effect after administration is at least 10%, 20%, 30%, 40%, 50%, 60%, 70%, 80%, or 90% lower than before administration of the anti-pTau antibody or antigen-binding moiety, as measured by assays known in the art.

In some embodiments, according to any of the methods comprising administration of an anti-pTau antibody or antigen-binding moiety to a subject, the Tau-associated neurodegenerative disease is a tauopathy. In some embodiments, the tauopathy is a neurodegenerative tauopathy. In some embodiments, the tauopathy is Alzheimer's Disease (AD), primary age-related tauopathy (PART), chronic traumatic encephalopathy (CTE), dementia pugilistica, progressive supranuclear palsy, corticobasal degeneration, frontotemporal dementia, frontotemporal dementias with parkinsonism linked to chromosome 17 (FTDP-17), Lytico-Bodig disease, meningioangiomatosis, postencephalitic parkinsonism, subacute sclerosing pan encephalitis, Pick's Disease, corticobasal degeneration, traumatic brain injury (TBI), argyrophilic grains disease, postencephalic parkinsonism (PEP), parkinsonism dementia complex of Guam (PDCG), tangle-dominant dementia, or globular glial tauopathies (GGTs).

In some embodiments, according to any of the methods comprising administration of an anti-pTau antibody or antigen-binding moiety to a subject, the anti-pTau antibody or antigen-binding moiety is incorporated into a formulation comprising the anti-pTau antibody or antigen-binding moiety, nucleic acid encoding the anti-pTau antibody or antigen-binding moiety, and/or host cells capable of expressing the anti-pTau antibody or antigen-binding moiety. In some embodiments, the anti-pTau antibody or antigen-binding moiety is formulated into a pharmaceutical composition by combination with appropriate pharmaceutically acceptable carriers or diluents.

In some embodiments, according to any of the methods comprising administration of an anti-pTau antibody or antigen-binding moiety to a subject, the method further comprises administering to the subject at least one additional therapeutic agent, such as a biologically active substance or compound including, for example, a known compound used in the medication of tauopathies and/or of amyloidoses, a group of diseases and disorders associated with amyloid or amyloid-like protein such as the amyloid β protein involved in Alzheimer's Disease. In some embodiments, the at least one additional therapeutic agent is selected from neurological drugs, corticosteroids, antibiotics, antiviral agents, anti-pTau antibodies, Tau inhibitors, anti-amyloid beta antibodies, beta-amyloid aggregation inhibitors, anti-BACE1 antibodies, and BACE1 inhibitors. In some embodiments, the at least one additional therapeutic agent is selected from neuron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, nonsteroidal anti-inflammatory drugs, antioxidants, serotonergic receptor antagonists, or other therapeutic agents. In particular, the biologically active agent or compound may comprise at least one compound selected from compounds against oxidative stress, anti-apoptotic compounds, metal chelators, inhibitors of DNA repair such as pirenzepine and metabolites, 3-amino-1-propanesulfonic acid (3 APS), 1,3-propanedisulfonate (1,3PDS), secretase activators, beta- and gamma-secretase inhibitors, tau proteins, anti-Tau antibodies (including, but not limited to, antibodies disclosed in WO 2012049570, WO 2014028777, WO 2014165271, WO 2014100600, WO 2015200806, U.S. Pat. Nos. 8,980,270 and 8,980,271), neurotransmitter, beta-sheet breakers, antiinflammatory molecules, "atypical anti-psychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, choline, Ginkgo biloba, acyetyl-L-carnitine, idebenone, propentofylline, or a xanthine derivative.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In some embodiments, administration of the anti-pTau antibody and administration of an additional therapeutic agent occur within about one month, or within about one, two or three weeks, or within about one, two, three, four, five, or six days, of each other.

In some embodiments, according to any of the methods comprising administration of an anti-pTau antibody or antigen-binding moiety to a subject, the subject is diagnosed as having or being at risk of developing a Tau-associated neurodegenerative disease, such as a tauopathy, including those described herein. In some embodiments, the subject is diagnosed as having or being at risk of developing a tauopathy. In some embodiments, according to any of the methods comprising administration of an anti-pTau antibody or antigen-binding moiety to a subject, the Tau-associated neurodegenerative disease is a tauopathy. In some embodiments, the tauopathy is a neurodegenerative tauopathy. In some embodiments, the tauopathy is Alzheimer's Disease (AD), primary age-related tauopathy (PART), chronic traumatic encephalopathy (CTE), dementia pugilistica, progressive supranuclear palsy, corticobasal degeneration, frontotemporal dementia, frontotemporal dementias with parkinsonism linked to chromosome 17 (FTDP-17), Lytico-Bodig disease, meningioangiomatosis, postencephalitic parkinsonism, subacute sclerosing pan encephalitis, Pick's Disease, corticobasal degeneration, traumatic brain injury (TBI), argyrophilic grains disease, postencephalic parkinsonism (PEP), parkinsonism dementia complex of Guam (PDCG), tangle-dominant dementia, or globular glial tauopathies (GGTs). In some embodiments, the tauopathy is Alzheimer's disease (AD), progressive supranuclear palsy (PSP), corticobasal degeneration (CBD), or Pick's disease (PiD).

In some embodiments, according to any of the methods comprising administration of an anti-pTau antibody or antigen-binding moiety to a subject, the anti-pTau antibody or antigen-binding moiety comprises a) a heavy chain variable region comprising i) a CDR1 comprising the amino acid sequence of any one of SEQ ID NOs: 49-59 or a variant thereof having at least 80%, at least 90%, or at least 95% sequence identity to the amino acid sequence of any one of SEQ ID NOs: 49-59; ii) a CDR2 comprising the amino acid sequence of any one of SEQ ID NOs: 60-70 or a variant thereof having at least 80%, at least 90%, or at least 95% sequence identity to the amino acid sequence of any one of SEQ ID NOs: 60-70; and/or iii) a CDR3 comprising the amino acid sequence of any one of SEQ ID NOs: 71-81 or a variant thereof having at least 80%, at least 90%, or at least 95% sequence identity to the amino acid sequence of any one of SEQ ID NOs: 71-81; and/or b) a light chain variable region comprising iv) a CDR1 comprising the amino acid sequence of any one of SEQ ID NOs: 82-90 or a variant thereof having at least 80%, at least 90%, or at least 95% sequence identity to the amino acid sequence of any one of SEQ ID NOs: 82-90; v) a CDR2 comprising the amino acid sequence of any one of SEQ ID NOs: 91-95 or a variant thereof having at least 80%, at least 90%, or at least 95% sequence identity to the amino acid sequence of any one of SEQ ID NOs: 91-95; and/or vi) a CDR3 comprising the amino acid sequence of any one of SEQ ID NOs: 96-105 or a variant thereof having at least 80%, at least 90%, or at least 95% sequence identity to the amino acid sequence of any one of SEQ ID NOS: 96-105. In some embodiments, the heavy chain and/or light chain CDR sequences are as indicated for a given antibody clone shown in Tables 1 and 2.

In some embodiments, according to any of the methods comprising administration of an anti-pTau antibody or antigen-binding moiety to a subject, the anti-pTau antibody or antigen-binding moiety thereof comprises a heavy chain variable region comprising the amino acid sequence of any one of SEQ ID NOs: 1-12 and 106 or a variant thereof having at least 80%, at least 90%, at least 95%, at least 96%, at least 97%, at least 98%, or at least 99% sequence identity to the amino acid sequence of any one of SEQ ID NOs: 1-12 and 106; and/or a light chain variable region comprising the amino acid sequence of any one of SEQ ID NOs: 13-24 and 107 or a variant thereof having at least 80%, at least 90%, at least 95%, at least 96%, at least 97%, at least 98%, or at least 99% sequence identity to the amino acid sequence of any one of SEQ ID NOs: 13-24 and 107. In some embodiments, the heavy chain variable region comprises the amino acid sequence of any one of SEQ ID NOs: 1-12 and 106; and/or the light chain variable region comprises the amino acid sequence of any one of SEQ ID NOs: 13-24 and 107. In some embodiments, the heavy chain and light chain variable regions are as indicated for a given antibody clone shown in Table 3.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. In some embodiments, the administration of an anti-pTau antibody or antigen-binding moiety to a subject is intravenous. In some embodiments, the administration of an anti-pTau antibody or antigen-binding moiety to a subject is subcutaneous. Various dosing schedules including but not limited to single or multiple administrations over various time-points, bolus administration, and pulse infusion are contemplated herein.

Antibodies of the invention may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg to 10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment may generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy can be monitored by conventional techniques and assays.

It is understood that any of the above formulations or therapeutic methods may be carried out using an immunoconjugate of the invention in place of or in addition to an anti-pTau antibody.

In some embodiments, provided herein is an anti-pTau antibody or antigen-binding moiety according to any of the embodiments described herein, nucleic acid encoding the anti-pTau antibody or antigen-binding moiety, and/or host cells capable of expressing the anti-pTau antibody or antigen-binding moiety for use in the treatment of a Tau protein-associated disease in a subject, such as for use in the manufacture of a medicament for the treatment of a Tau protein-associated disease. In some embodiments, the disease is a tauopathy, including any of the tauopathies described herein.

Compositions

In another aspect, provided herein is a composition comprising one or more of: an anti-pTau antibody or antigen-binding moiety as described herein; nucleic acid encoding an anti-pTau antibody or antigen-binding moiety as described herein; and a host cell capable of expressing an anti-pTau antibody or antigen-binding moiety as described herein. In some embodiments, the composition is a pharmaceutical composition and further comprises a pharmaceutically acceptable excipient and/or carrier.

In some embodiments, provided herein are pharmaceutical preparations or compositions comprising an anti-pTau antibody or antigen-binding moiety according to any of the embodiments described herein, nucleic acid encoding the anti-pTau antibody or antigen-binding moiety, and/or host cells capable of expressing the anti-pTau antibody or antigen-binding moiety present in a pharmaceutically acceptable vehicle. "Pharmaceutically acceptable vehicles" may be vehicles approved by a regulatory agency of the Federal or a state government or listed in the US Pharmacopeia or other generally recognized pharmacopeia for use in mammals, such as humans. The term "vehicle" refers to a diluent, adjuvant, excipient, or carrier with which a compound of the disclosure is formulated for administration to a mammal. Such pharmaceutical vehicles can be lipids, e.g., liposomes, e.g., liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semisolid, liquid or gaseous forms, such as tablets, capsules, powders, granules, ointments, solutions, suppositories, injections, inhalants, gels, microspheres, and aerosols. As such, administration of the anti-pTau antibody or antigen-binding moiety, nucleic acid encoding the anti-pTau antibody or antigen-binding moiety, and/or host cells capable of expressing the anti-pTau antibody or antigen-binding moiety can be achieved in various ways, including by intravenous, oral, buccal, rectal, parenteral, intraperitoneal, intradermal, transdermal, intratracheal, intraocular, etc., administration. For example, administration of the anti-pTau antibody or antigen-binding moiety, nucleic acid encoding the anti-pTau antibody or antigen-binding moiety, and/or host cells capable of expressing the anti-pTau antibody or antigen-binding moiety can be achieved by intravenous or subcutaneous administration. In some embodiments, the composition of an anti-pTau antibody or antigen-binding moiety is suitable for intravenous administration to a subject. In some embodiments, the composition of an anti-pTau antibody or antigen-binding moiety is suitable for subcutaneous administration to a subject. The active agent may be systemic after administration or may be localized by the use of regional administration, intramural administration, or use of an implant that acts to retain the active dose at the site of implantation. The active agent may be formulated for immediate activity or it may be formulated for sustained release.

Pharmaceutical compositions can include, depending on the formulation desired, pharmaceutically acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and/or enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Kits

In another aspect, provided herein are kits for carrying out a method described herein. A kit can include one or more of: an anti-pTau antibody or antigen-binding moiety as described herein; nucleic acid encoding an anti-pTau antibody or antigen-binding moiety as described herein; and a host cell capable of expressing an anti-pTau antibody or antigen-binding moiety as described herein. In some embodiments, the kit further comprises a reagent for reconstituting and/or diluting one or more of the kits components.

A kit as described herein can further include one or more additional reagents, where such additional reagents can be selected from: a dilution buffer; a reconstitution solution; a wash buffer; a control reagent; a control expression vector or polyribonucleotide; a reagent for in vitro production of the anti-pTau antibody or antigen-binding moiety from DNA, and the like.

Components of a kit can be in separate containers; or can be combined in a single container.

In addition to the above-mentioned components, a kit can further include instructions for using the components of the kit to practice the methods. The instructions for practicing the methods are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or sub-packaging) etc. In some embodiments, the instructions are present as an electronic storage data file present on a suitable computer readable storage medium, e.g., CD-ROM, diskette, flash drive, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as Sambrook, J., & Russell, D. W. (2012). *Molecular Cloning: A Laboratory Manual* (4th ed.). Cold Spring Harbor, N.Y.: Cold Spring Harbor Laboratory and Sambrook, J., & Russel, D. W. (2001). *Molecular Cloning: A Laboratory Manual* (3rd ed.). Cold Spring Harbor, N.Y.: Cold Spring Harbor Laboratory (jointly referred to herein as "Sambrook"); Ausubel, F. M. (1987). *Current Protocols in Molecular Biology*. New York, N.Y.: Wiley (including supplements through 2014); Bollag, D. M. et al. (1996). *Protein Methods*. New York, N.Y.: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, Calif.: Academic Press; Lefkovits, I. (1997). *The Immunology Methods Manual: The Comprehensive Sourcebook of Techniques*. San Diego, Calif.: Academic Press; Doyle, A. et al. (1998). *Cell and Tissue Culture: Laboratory Procedures in Biotechnology*. New York, N.Y.: Wiley; Mullis, K. B., Ferré, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, N.Y.: Cold Spring Harbor Laboratory Press; Beaucage, S. L. et al. (2000). *Current Protocols in Nucleic Acid Chemistry*. New York, N.Y.: Wiley, (including supplements through 2014); and Makrides, S. C. (2003). *Gene Transfer and Expression in Mammalian Cells*. Amsterdam, NL: Elsevier Sciences B.V., the disclosures of which are incorporated herein by reference.

Additional embodiments are disclosed in further detail in the following examples, which are provided by way of illustration and are not in any way intended to limit the scope of this disclosure or the claims.

Materials and Methods
Human Brain Lysate Preparation

Brain tissues as indicated were purchased from Banner Health Institute (AZ, USA). Brain homogenate were prepared from frontal cortexes of 3 AD (Alzheimer's Disease, Braak Stage V & VI) patients and 3 ND (non-demented, Braak Stage III) individuals. Lysis buffer (50 mM Tris pH 8.0, 274 mM NaCl, 5 mM KCl, 2 mM EGTA, 2 mM EDTA, protease and phosphatase inhibitor (Pierce, 88668)) was added to the brain tissue at ~5 ml/g. ZrO2 beads were then added and Bullet Blender (Next Advance) was set at level 9 for 2 min to generate homogenate. Homogenate was spun at 13,000×g for 15 min at 4° C. Supernatant was collected as total lysate. Protein concentration was determined by Bradford Protein Assay.

Sarkosyl Extraction to Generate S1 and P2 Fractions 1 mg total lysate in 0.9 ml lysis buffer was incubated with 0.1 ml 10% N-laurylsarcosine (dissolved in lysis buffer) for 1 hr at room temperature. Mixture was spun at 150,000×g for 20 min at 4° C. Supernatant was collected as 51 fraction, whereas the pellet was resuspended in 500 µl PBS and spun at 150,000×g for 20 min at 4° C. 100 µl PBS was used to resuspend the pellet as P2.

Western Blot

Frozen brain lysates were thawed on ice and 15 µg was aliquoted and PBS was added to 15 µL. Five µL of NuPAGE® LDS sample buffer (Invitrogen) and 2 µL of NuPAGE® Sample Reducing Agent (Invitrogen) were then added and the tube was boiled at 100° C. for 5 min. Boiled samples were loaded into the wells of a Bolt™ 4-12% Bis-Tris Plus Gels in a Mini Gel Tank (Invitrogen). PageRuler prestained protein ladder (Invitrogen) was loaded as the molecular weight marker to visualize the progression of protein migration at a constant voltage set at 150V. After the dye front was migrated out of the gel, gel running was stopped, followed by protein band transfer onto a precut PVDF membrane using a preset P0 program (20V, 1 min; 23V, 4 mins; 25V, 2 mins) of a iBlot 2 Dry Blotting System (Invitrogen). Membrane was then blocked by blocking buffer (LI-COR) for 30 min at room temperature. 0.2 µg/mL of the first antibodies (prepared in blocking buffer) were incubated with membrane for 1 hr at room temperature. Membrane were washed with PBS for 5 min at room temperature 3 times. Secondary antibody (LI-COR, diluted at 1:10,000 by blocking buffer) was incubated with membrane for 1 hr at room temperature. Membrane were washed again with PBS for 5 min at room temperature 3 times. Odyssey Imaging Systems scanning was performed to visualize proteins on the membrane.

S1 and P2 Tau Quantification by Western Blot

Briefly, recombinant full-length Tau (1.25 to 40 ng Tau, 2-fold increment), S1 and P2 are mixed with reducing agent (Invitrogen, NP009), LDS sample buffer (Invitrogen, NP007) and boiled at 100° C. for 5 min. Samples were separated by Bolt™ 4-12% Bis-Tris Plus Gels (Invitrogen, NW04125BOX) and transferred to PVDF membrane by iBlot 2 Dry Blotting System (Invitrogen). Intensities of serially diluted recombinant full-length Tau protein were used to plot calibration curve, and the equation of linear regression was used to determine Tau concentrations in the samples.

Synaptoneurosome and Cytosol Preparation

Brain piece was transferred into a cold 2 mL glass homogenizer with cold buffer A ((25 mM HEPES, pH7.5. 120 mM NaCl, 5 mM KCl, 1 mM MgCl2, 2 mM CaCl2, protease and phosphatase inhibitor (Thermo, 88668) were added freshly)). Teflon pestle was attached to the stirring motor and set the speed at 170 rpm. First, short strokes were applied to disrupt the tissue completely until no large pieces left, and then apply 7 up-and-down strokes to homogenize. Homogenate was added into the 3 mL syringe with 80 µm filters (Millipore, #NY8002500) and filtrate the homogenate by pushing gently through the 80 µm filter. The filtrated homogenate was load onto a syringe with 5 µm filter gently. Filtrate was spun at 1000 g for 10 mins, pellet and supernatant is collected as P1 and S1. P1 was wash by buffer A and spun at 1000 g for 10 mins. Pellet was collected as synaptoneurosome fraction. S1 was centrifuged at 100,000 g for 30 mins to remove all organelles and collect supernatant as the cytosol fraction.

Example 1: Selection of Antibodies that Bind Pathological Tau Species

Antibodies that bind pathological Tau species were generated by employing conventional hybridoma techniques. Antibodies were identified as described in Tables 1-3.

TABLE 1

Antibody heavy chain CDRs

| Antibody clone | Heavy chain CDR1 | Heavy chain CDR2 | Heavy chain CDR3 |
|---|---|---|---|
| mAb004 | SYGMS (SEQ ID NO: 49) | TISSSGSYTYYPDSVKG (SEQ ID NO: 60) | TYYGAMDY (SEQ ID NO: 71) |
| mAb005 | DYGMH (SEQ ID NO: 50) | YSNSDSTTIYYADTVKG (SEQ ID NO: 61) | SYYSNYVDY (SEQ ID NO: 72) |
| mAb008 | RYWMS (SEQ ID NO: 51) | EINPDGNAINYAPSLKD (SEQ ID NO: 62) | PFPSV (SEQ ID NO: 73) |
| mAb010 | GYGVN (SEQ ID NO: 52) | MIWGDGSTDYNSALKS (SEQ ID NO: 63) | WAFAY (SEQ ID NO: 74) |
| mAb011 | SYWMH (SEQ ID NO: 53) | MIDPSDSETRLNQKFKD (SEQ ID NO: 64) | PYGDLDY (SEQ ID NO: 75) |
| mAb013 | DFYMK (SEQ ID NO: 54) | DIDPNNGDTFYNQKFKG (SEQ ID NO: 65) | DLY (SEQ ID NO: 76) |
| mAb020 | SYAVH (SEQ ID NO: 55) | VMWSGGSTDYNAAFIS (SEQ ID NO: 66) | MGDYDGVAWFAY (SEQ ID NO: 77) |

TABLE 1-continued

Antibody heavy chain CDRs

| Antibody clone | Heavy chain CDR1 | Heavy chain CDR2 | Heavy chain CDR3 |
|---|---|---|---|
| mAb025 | THGMS (SEQ ID NO: 56) | TYSGVPTYTDDFKG (SEQ ID NO: 67) | SELSWFAY (SEQ ID NO: 78) |
| mAb032 | SYWMN (SEQ ID NO: 57) | QIYPGDGDTDYNGKFKG (SEQ ID NO: 68) | RSPY (SEQ ID NO: 79) |
| mAb033 | TFGMGVG (SEQ ID NO: 58) | HIWWDDDKYYNPALKS (SEQ ID NO: 69) | RGSNALDY (SEQ ID NO: 80) |
| mAb037 | DYNMD (SEQ ID NO: 59) | DINPNTGGTIYNQKFKG (SEQ ID NO: 70) | EGPYYYGTTHPFAY (SEQ ID NO: 81) |

TABLE 2

Antibody light chain CDRs

| Antibody clone | Light chain CDR1 | Light chain CDR2 | Light chain CDR3 |
|---|---|---|---|
| mAb004 | RSSQTIVHSNGNTYLE (SEQ ID NO: 82) | KVSNRFS (SEQ ID NO: 91) | FQGSLVPWT (SEQ ID NO: 96) |
| mAb005 | RSSQSLVHSNGNTYLH (SEQ ID NO: 83) | KVSNRFS (SEQ ID NO: 91) | FQSTHVPPT (SEQ ID NO: 97) |
| mAb008 | RSSQSLVRSNGNTYLE (SEQ ID NO: 84) | KVSNRFS (SEQ ID NO: 91) | FQGSHVPYT (SEQ ID NO: 98) |
| mAb010 | KSSQSLLDSGGKTYLN (SEQ ID NO: 85) | QVSKLDSGVPD (SEQ ID NO: 92) | WQGTHFPLT (SEQ ID NO: 99) |
| mAb011 | KSSQSLLDSDGKTYLN (SEQ ID NO: 86) | LVSKLDS (SEQ ID NO: 93) | WQGTHFPFT (SEQ ID NO: 100) |
| mAb013 | KSSQSLLYSNGKTYLN (SEQ ID NO: 87) | LVSKLDS (SEQ ID NO: 93) | VQGTHFPHT (SEQ ID NO: 101) |
| mAb020 | RSSQSLVHSNGNTYLH (SEQ ID NO: 83) | KVSNRFS (SEQ ID NO: 91) | SQSTHVPPWT (SEQ ID NO: 102) |
| mAb025 | RASQSISDYLH (SEQ ID NO: 88) | YASQSIS (SEQ ID NO: 94) | QNGHSFPYT (SEQ ID NO: 103) |
| mAb032 | RSSQSIVHSNGNTYLE (SEQ ID NO: 89) | KVSNRFS (SEQ ID NO: 91) | FQGSHVPYT (SEQ ID NO: 98) |
| mAb033 | RSSQSLANSYGNTYLS (SEQ ID NO: 90) | GISNRFS (SEQ ID NO: 95) | LQGTHQPWT (SEQ ID NO: 104) |
| mAb037 | KSSQSLLYSNGKTYLN (SEQ ID NO: 87) | LVSKLDS (SEQ ID NO: 93) | VQGTHFPQT (SEQ ID NO: 105) |

TABLE 3

Antibody variable regions

| Antibody clone (variable region) | Sequence |
|---|---|
| mAb004 ($V_H$) | EVQLVESGGDLVESGGSLKLSCAASGFTFSSYGMSWVRQTPDKRLEWVATISSS GSYTYYPDSVKGRFTISRDNAKNTLYLQMSSLNSEDTAMYYCADTYYGAMDY WGQGTSVTVSS (SEQ ID NO: 1) |
| mAb004 ($V_L$) | DVLMTQTPLSLPVSLGDQASISCRSSQTIVHSNGNTYLEWYLQKPGQSPKLLIYK VSNRFSGVPDRFSGSGSGTDFTLKISRVEAEDLGVYYCFQGSLVPWTFGGGTQLE IR (SEQ ID NO: 13) |

TABLE 3-continued

Antibody variable regions

| Antibody clone (variable region) | Sequence |
|---|---|
| mAb005 (V$_H$) | EVQLVESGGGLVKPGGSLKLSCAASGFTFSDYGMHWVRQAPEKGLEWVAYSN SDSTTIYYADTVKGRFTISRDNAKSTLFLQMTSLRSEDTAMYYCGRSYYSNYVD YWGQGTTLTVSS (SEQ ID NO: 2) |
| mAb005 (V$_L$) | DIVMTQIPLSLPVSLGDQASISCRSSQSLVHSNGNTYLHWYLQKPGQSPKLLIYK VSNRFSGVPDRFSGSGSGTDFTLKISRVEAEDLGVYFCFQSTHVPPTFGGGTKLEI K (SEQ ID NO: 14) |
| Humanized mAb005, (V$_H$) | EVQLVESGGGLVQPGGSLRLSCAASGFTFSDYGMHWVRQAPGKGLEWVAYSN SDSTTIYYADTVKGRFTISRDNAKNSLYLQMNSLRAEDTAVYYCGRSYYSNYVD YWGQGTLVTVSS (SEQ ID NO: 3) |
| Humanized mAb005, (V$_L$) | DVVMTQSPLSLPVTLGQPASISCRSSQSLVHSNGNTYLHWYLQRPGQSPRLLIYK VSNRFSGVPDRFSGSGSGTDFTLKISRVEAEDVGVYFCFQSTHVPPTFGQGTKLEI K (SEQ ID NO: 15) |
| mAb008 (V$_H$) | EVKLLQSGGGLVQPGGSLKVSCAASGFDFSRYWMSWVRRAPGKGLEWIGEINP DGNAINYAPSLKDKFIVSRDNAKNTLYLQMSNVRSEDTALYYCARPFPSVWGT GTTVTVSS (SEQ ID NO: 4) |
| mAb008 (V$_L$) | DVLMTQTPLSLPVSLGDQASISCRSSQSLVRSNGNTYLEWYLQNPGQSPKLLIYK VSNRFSGVPDRFSGSGSGTDFTLKISRVEAEDLGVYYCFQGSHVPYTFGGGTKLE IK (SEQ ID NO: 16) |
| mAb010 (V$_H$) | QVQLKESGPGLVAPSQSLSITCTVSGFSLTGYGVNWVRQPPGKGLEWLGMIWG DGSTDYNSALKSRLSISKDNSKSQVFLKMNSLQTDDTARYYCANWAFAYWGQ GTLVTVSA (SEQ ID NO: 5) |
| mAb010 (V$_L$) | DVVMTQTPLTLSVTIGQPASISCKSSQSLLDSGGKTYLNWLLQRPGQSPKRLIYQ VSKLDSGVPDRFTGSGSGTDFTLKISRVEAEDLGVYYCWQGTHFPLTFGAGTKL ELK (SEQ ID NO: 17) |
| mAb011 (V$_H$) | QVQLQQSGPQLVRPGASVKISCKASGYSFTSYWMHWLKQRPGQGLEWIGMIDP SDSETRLNQKFKDKATLTVDKSSSTVYMHLSSPTSEDSAVYYCVRPYGDLDYW GQGTTLTVSS (SEQ ID NO: 6) |
| mAb011 (V$_L$) | DVVMTQTPLTLSVTIGQPASISCKSSQSLLDSDGKTYLNWLLQRPGQSPKRLIYL VSKLDSGVPDRFTGSGSGTDFTLKISRVEAEDLGVYYCWQGTHFPFTFGSGTKLE IK (SEQ ID NO: 18) |
| mAb013 (V$_H$) | EVQLQQSGPELVKPGASVKMSCKASGYTFTDFYMKWVKQSHGKSFEWIGDIDP NNGDTFYNQKFKGKATLTVDKSSSTAYMQLNSLTSEDSAVYYCARDLYWGQG TTLTVSS (SEQ ID NO: 7) |
| mAb013 (V$_L$) | DVVMTQTPLTLSVTIGQPASISCKSSQSLLYSNGKTYLNWLLQRPGQSPKRLIYL VSKLDSGVPDRFTGSGSGTDFTLKISRVEAEDLGVYYCVQGTHFPHTFGGGTKL EIK (SEQ ID NO: 19) |
| mAb020 (V$_H$) | QVQLKQSGPGLVQPSQSLSITCTVSGFSLTSYAVHWVRQSPGKGLEWLGVMWS GGSTDYNAAFISRLSISKDNSKSQVFFKMNSLQADDTAIYYCARMGDYDGVAW FAYWGQGTLVTVSA (SEQ ID NO: 8) |
| mAb020 (V$_L$) | DVVMTQTPLSLPVSLGDQASISCRSSQSLVHSNGNTYLHWYLQKPGQSPKLLIY KVSNRFSGVPDRSGSGSGTDFTLKISRVEAEDLGVYFCSQSTHVPPWTFGGGTK LEIK (SEQ ID NO: 20) |
| mAb025 (V$_H$) | QIQLVQSGPELKKPGETVKISCKASGYTFTTHGMSWVKQAPGKGLKWMGWINT YSGVPTYTDDFKGRFAFSLETSASTAYLQINNLKNEDTATYFCARSELSWFAYW GQGTLVTVSA (SEQ ID NO: 9) |
| mAb025 (V$_L$) | DIVMTQSPATLSVTPGDRVSLSCRASQSISDYLHWYQQKSHESPRLLIKYASQSIS GIPSRFSGSGSGSDFTLSINSVEPEDVGVYYCQNGHSFPYTFGGGTKLEIK (SEQ ID NO: 21) |
| mAb032 (V$_H$) | QVQLQQSGAELVKPGASVKISCKASGYAFSSYWMNWVKQRPGKGLEWIGQIYP GDGDTDYNGKFKGKATLTADTSSSTAYMQLSSLTSEDSAVYFCASRSPYWGQG TLVTVSA (SEQ ID NO: 10) |
| mAb032 (V$_L$) | DILMTQTPLSLPVSLGDQASISCRSSQSIVHSNGNTYLEWYLQKPGQSPKLLIYKV SNRFSGVPDRFSGSGSGTDFTLKISRVEAEDLGVYYCFQGSHVPYTFGGGTKLEI K (SEQ ID NO: 22) |

TABLE 3-continued

Antibody variable regions

| Antibody clone (variable region) | Sequence |
|---|---|
| mAb033 (V$_H$) | QVTLKESGPGILQPSQTLSLTCSFSGFSLSTFGMGVGWFRQPSGKGLEWLAHIW WDDDKYYNPALKSRLTISKDTSKNQVFLKIANVDTADTATYYCARRGSNALDY WGQGTSVTVSS (SEQ ID NO: 11) |
| mAb033 (V$_L$) | DVVVTQTPLSLPVSFGDQVSISCRSSQSLANSYGNTYLSWYLHKPGQSPQLLIYGI SNRFSGVPDRFSGSGSGTDFTLKISTIKPEDLGMYYCLQGTHQPWTFGGGTKLEI K (SEQ ID NO: 23) |
| mAb037 (V$_H$) | EVQLQQSGPELVKPGASVKIPCKASGYTFTDYNMDWVKQSHGKSLEWIGDINP NTGGTIYNQKFKGKATLTVDKSSSTAYMELRSLTSEDTAVYYCAGEGPYYYGT THPFAYWGQGTLVTVSA (SEQ ID NO: 12) |
| mAb037 (V$_L$) | DVVMTQTPLTLSVTIGQPASISCKSSQSLLYSNGKTYLNWLLQRPGQSPKRLIYL VSKLDSGVPDRFTGSGSGTDFTLKISRVEAEDLGVYYCVQGTHFPQTFGGGTKL EIK (SEQ ID NO: 24) |
| Humanized mAb037 (V$_H$) | QVQLVQSGAEVKKPGASVKVSCKASGYTFTDYNMDWVRQAHGQGLEWIGDIN PNTGGTIYNQKFKGRATLTVDTSISTAYMELSRLRSDDTAVYYCAGEGPYYYGT THPFAYWGQGTLVTVSS (SEQ ID NO: 106) |
| Humanized mAb037 (V$_L$) | DVVMTQSPLSLPVTLGQPAISCKSSQSLLYSNGKTYLNWLLQRPGQSPRRLIYL VSKLDSGVPDRFSGSGSGTDFTLKISRVEAEDVGVYYCVQGTHFPQTFGGGTKL EIK (SEQ ID NO: 107) |

Example 2: Antibody Binding Profile in AD Brains in Comparison with ND Brains

To characterize the human Tau species recognized by mAb005 and mAb037 in healthy and diseased human brain tissues, western blot assays were performed using AD brain lysates and non-demented (ND) brain samples with HT7, mAb005 and mAb037 staining. FIG. 1 shows the results of western blots of AD and ND brain lysates stained by HT7, mAb005 and mAb037. Three ND (Non-demented; Braak Stage III) and three AD (Alzheimer's Disease, Braak Stage V-VI) frozen frontal cortices were obtained from Banner Sun Health Research Institute (AZ, USA) and equal amounts of tissues were dissected out for homogenization in Tris buffer and then combined for subsequent protein quantification. 15 μg of total lysates were resolved by SDS-PAGE and the western blot analysis was conducted for HT7 (left panel), mAb005 (middle panel) and mAb037 (right panel). Asterisk denotes 64 kD Tau species, and bracket denotes 140/170 kD Tau species. Over-exposed images are shown to illuminate weak signals.

In ND brain sample, a few Tau species (MW between 45 kD to 62 kD) were recognized by mAb005 and mAb037 whereas more Tau species (MW between 30 kD to 68 kD) were recognized by HT7. In AD brain lysates, mAb005 and mAb037 further recognized two Tau species (MW: 64 kD and 68 kD). The Tau species (MW: 64 kD) (FIG. 1, asterisk-marked band) corresponds to a hyperphosphorylated and sarkosyl-insoluble pathological Tau species (known in the art). In AD brain sample, HT7-bound Tau species (MW: 140/170 kD) (FIG. 1, bracket-marked bands) were not identified by mAb005, but detected by mAb037. Results showed that mAb005 and mAb037 recognized a sub-population of pathological Tau species (MW between 45 kD to 68 kD), including the Tau species (MW: 64 kD) in AD brain.

Figure 2:
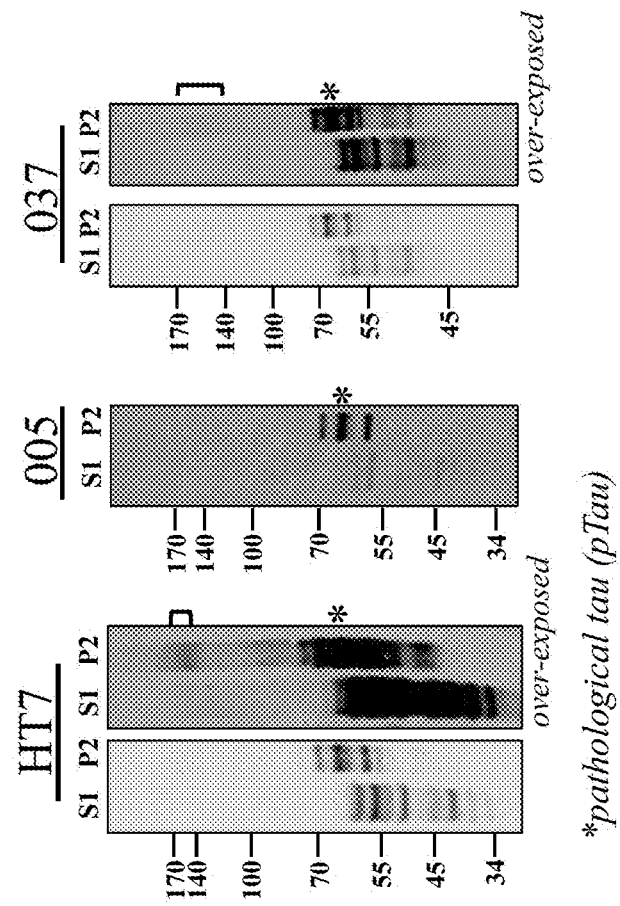
FIG. 2 shows the western blot analysis of Alzheimer's disease (AD) brain in sarkosyl-soluble and -insoluble fractions against mAb005 and mAb037.

Example 3: Antibody Binding Profile in Sarkosyl-Soluble and -Insoluble Fractions of AD Human Brains Since mAb005 and mAb037 binds to a 64 kD Tau species in AD diseased brain, corresponding to a sarkosyl-insoluble hyperphosphorylated form of Tau, western blot analysis was conducted on 10% sarkosyl-extracted AD brain lysate prepared by fractionation using high-speed centrifugation. FIG. 2 shows western blots of sarkosyl-soluble and -insoluble AD brain fractions. AD brain lysate was subjected to 10% sarkosyl extraction followed by a 150k×g centrifugation to obtain supernatant 1 (S1) and pellet 1 (P1). P1 was resuspended in PBS and spun again to obtain pellet 2 (P2). S1 denotes the sarkosyl-soluble fraction and P2 denotes the sarkosyl-insoluble fraction. Both S1 and P2 were loaded after being normalized to 10 ng of Tau for the western blot. Tau level measurements in these fractions were obtained by a separate western blot of these fractions together with a purified monomeric Tau protein in two-fold serial dilutions from 2.5 to 40 ng. Quantification was performed by Odyssey Imaging Systems (LI-COR). Asterisks denote 64 kD Tau species and 140/170 kD Tau species. Over-exposed images are shown to confirm the lack of binding of mAb005 and mAb037 to certain Tau species.

Other than mAb005 binding to the 64 kD Tau species (FIG. 2, asterisks) in the sarkosyl-insoluble fraction (P2), two major Tau species at 68 and 58 kD were also detected. Only a small number of sarkosyl-soluble (S1) Tau species were recognized by mAb005, and their molecular weights, identified as 45, 57 and 59 kD, are different than the Tau species recognized in the P2 fraction. Unlike mAb005, HT7 and mAb037 did not show a preference for Tau species present in either S1 or P2 fractions, recognizing a larger number of Tau species in the S1 fraction. In summary, mAb005 preferentially recognized three major Tau species, 58, 64, and 68 kD, in sarkosyl-insoluble fractions of AD brains, whereas HT7 and mAb037 showed no such preference.

Example 4: Antibody Binding Profile in Cytosol and Synaptoneurosome Fractions of ND and AD Human Brain Lysates Pathological Tau is known to accumulate at the synapses in AD brains (Tai, H. C., et al. (2012). *The American journal of pathology*, 181(4), 1426-1435). Dot-blot analysis was performed to address whether Tau species recognized by the antibodies described herein are enriched at synapses and whether the Tau species identified by western blot can be detected by Dot-blot under non-denaturing conditions.

Figure 3:
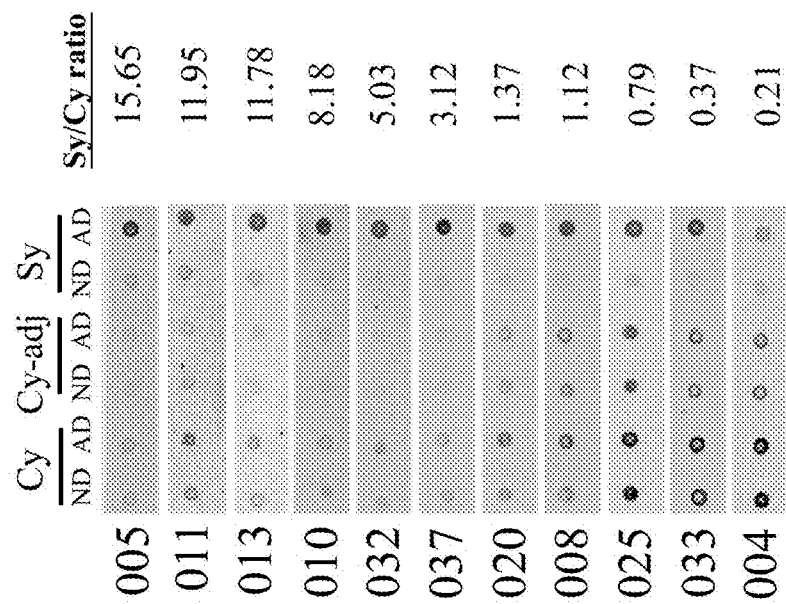
FIG. 3 shows subcellular fractionation and dot-blot analysis of Non-demented (ND) and Alzheimer's disease (AD) brain against mAbs 004, 005, 008, 010, 011, 013, 020, 025, 032, 033 and 037.

AD and ND brain lysates described herein were subjected to subcellular fractionation. Specifically, separation of cytosol and synaptoneurosome was carried out by two filtrations and several centrifugations. The protein level in each fraction was measured by Bradford Protein Assay (Bio-Rad), and equal amounts of protein (0.4 μg) were spotted onto a piece of nitrocellulose membrane and immunoblotting was performed after a brief air-dry period for the membrane. Enrichment of a synaptic marker, synaptophysin, and a cytosolic marker, GAPDH, was observed in synaptoneurosomal and cytosolic fractions, respectively (FIG. 3). Abbreviations: Cy: cytosol; Cy adj.: reduced amount of cytosol loaded to facilitate side-by-side comparison; Sy: synaptoneurosome. As shown in FIG. 3, mAbs 005, 008, 010, 011, 013, 020, 025, 032 and 037 showed preferential binding to Tau species localized at the synapses of AD brains but not of ND brains. Ratio of Sy to Cy was measured from 3 independent experiments shown by mean value for each antibody from top to bottom to demonstrate the synaptic preferences. Further, the antibodies described herein showed preferential binding to Tau species in AD total brain lysate, in agreement with the previous finding, whereas both reference antibodies showed preferential binding to Tau species in ND total brain lysate.

Example 5: Antibody Binding Profile in Tauopathy Human Brain Lysates

Figure 4:
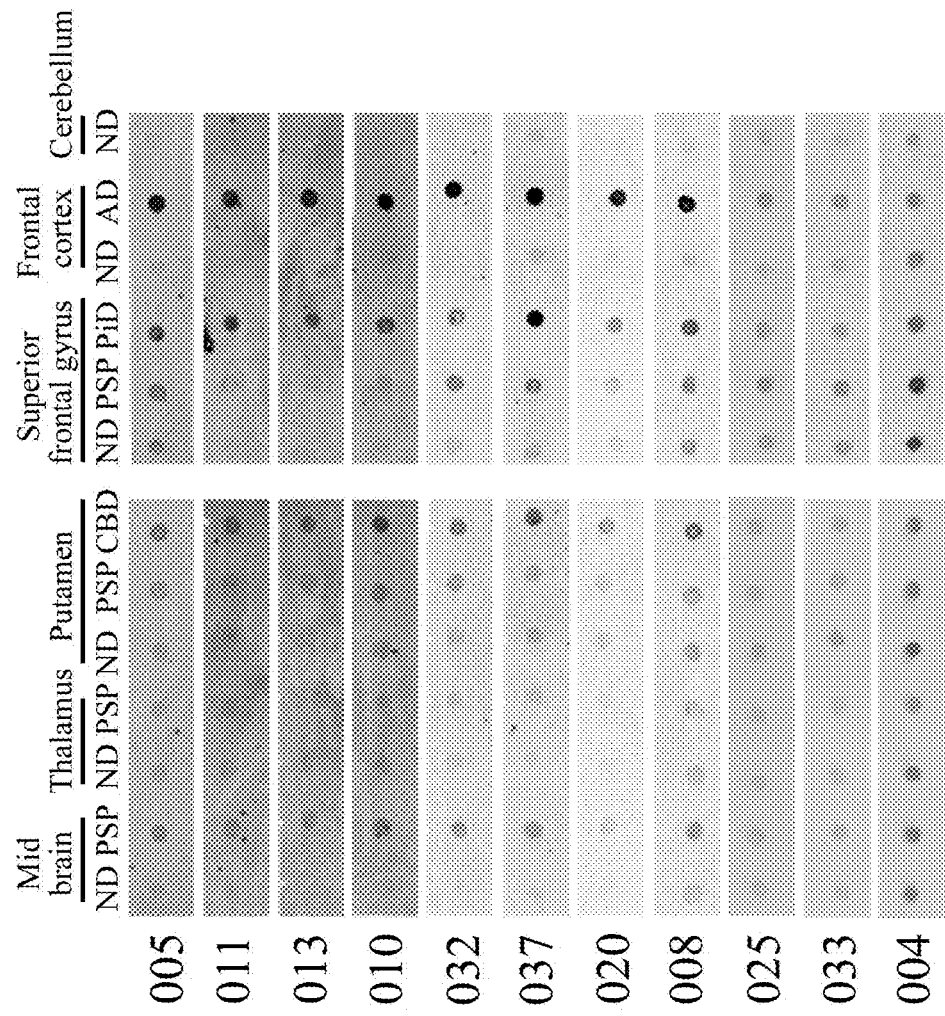
FIG. 4 shows dot-blot assays on brain tissues of Non-demented (ND), Alzheimer's disease (AD), progressive supranuclear palsy (PSP), Pick's Disease (PiD) and corticobasal degeneration (CBD) against mAbs 004, 005, 008, 010, 011, 013, 020, 025, 032, 033 and 037.

Pathological Tau species have been shown in the literature to accumulate in several tauopathies, including AD, progressive supranuclear palsy (PSP), corticobasal degeneration (CBD), and Pick's disease (PiD). To examine whether antibodies listed in FIG. 3 recognize Tau species in tauopathies other than AD, frozen brain tissues from PSP, CBD, and PiD brains were obtained from Banner Sun Health Research Institute (AZ, USA) for Dot-blot analysis as described in Example 4. As shown in FIG. 4, order of antibodies was the same as FIG. 3. Higher signals in PSP, CBD and PiD diseased brain were observed for those antibodies toward the top of the list, and higher discriminating ability of antibodies was observed for AD brains.

Figure 5:
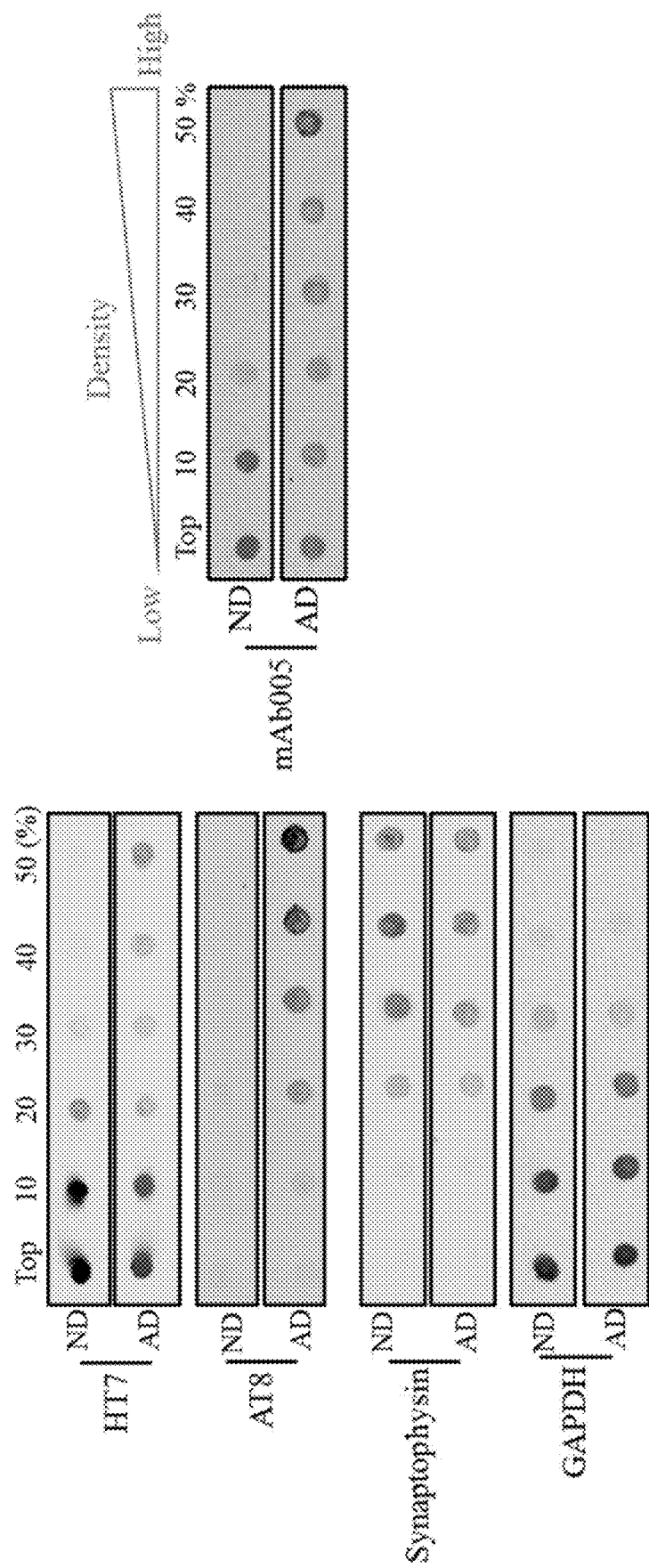
FIG. 5 shows the sucrose-gradient-centrifugation (SGC) and dot-blot analysis of Non-demented (ND) and Alzheimer's disease (AD) brain lysates, probed with mAb005.

Example 6: Antibody Binding Profile in Sucrose-Gradient Fractionated AD and ND Brain Lysates Seed-competent forms of pathological Tau species have been found in the high-density fraction of sucrose gradient fractionated Tau transgenic mouse brain lysates (Jackson et al., 2016 JN). Sucrose gradient analysis was performed to evaluate the densities of mAb005-positive Tau species in human brain lysates. Dot-blot assay of the sucrose-gradient fractionated brain lysates under non-denaturing conditions was performed with antibodies including: HT7, AT8, synaptophysin, GAPDH, and mAb005 (FIG. 5).

Dot-blot analysis was performed for SEC-fractionated samples without heat-denaturation, probing with HT7, AT8, synaptophysin, GAPDH, and mAb005. HT7 had a similar fluctuation pattern of signals to AT8 across all fractions in western blot (FIG. 6), whereas AT8's signals in both Top and 10% fractions were absent in Dot-blot. Synaptophysin, a synaptic marker, was mostly present in the 20-50%, whereas the cytosolic marker GAPDH was more enriched in the low-density fractions from top to 20%.

In summary, mAb005-positive Tau species were observed to be present in all fractions in AD with an increased signal at the highest density fraction (50%), suggesting the mAb005-positive Tau species were incorporated into multiple complexes with a widely diverse nature, more so than HT7 and AT8.

Figure 6:
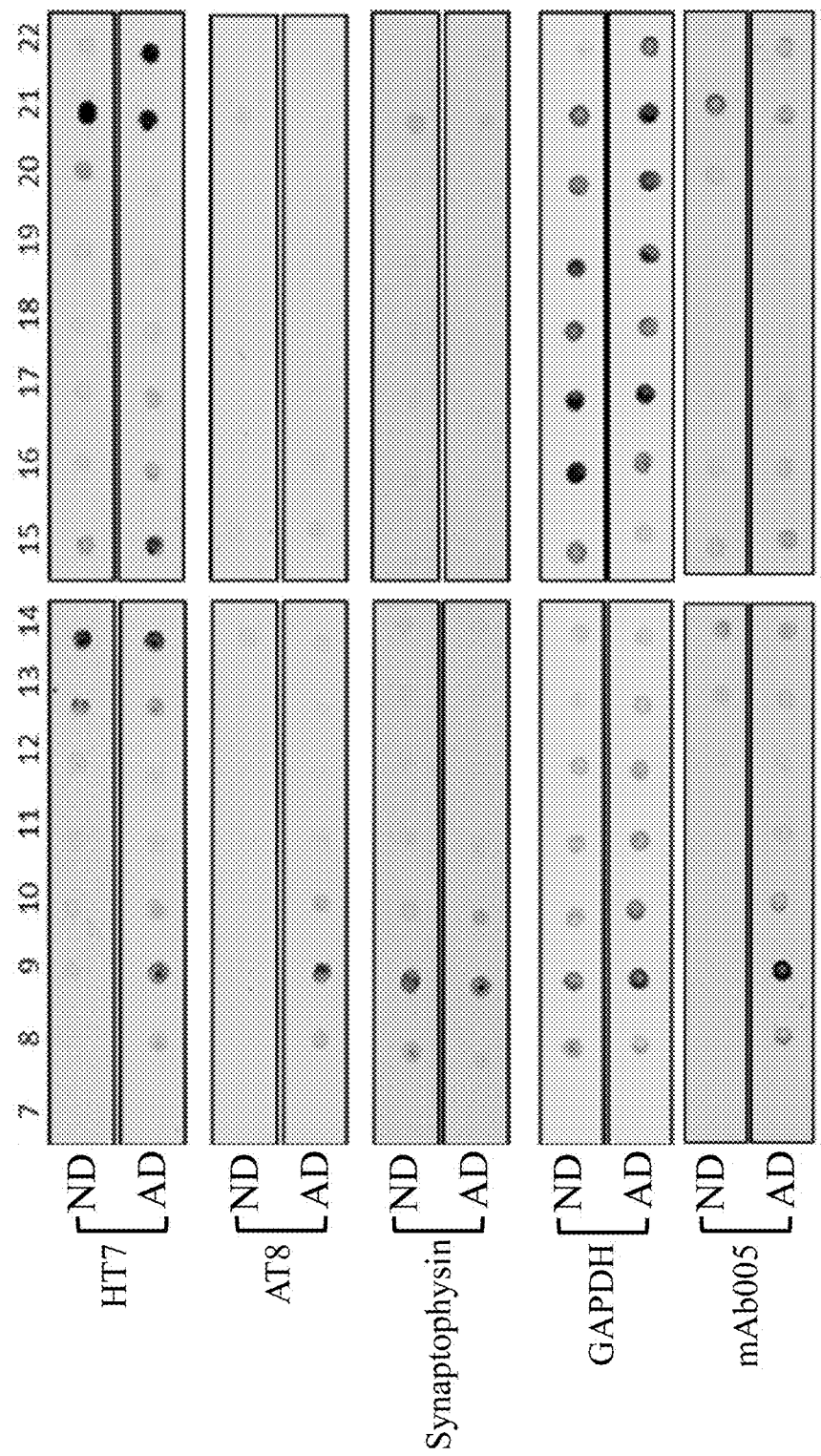
FIG. 6 shows the dot-blot analysis of Non-demented (ND) and Alzheimer's disease (AD) brain lysates for mAb005 after size exclusion chromatography (SEC).

Example 7: Antibody Binding Profile in SEC Fractionated AD and ND Brain Lysates To gain insight into the complex nature of mAb005-positive Tau species, SEC analysis of ND and AD brain lysates was performed to separate different Tau species according to their molecular weights. FIG. 6 shows the dot-blot analysis of ND and AD brain lysates after size exclusion chromatography (SEC). Calibration by molecular size marker revealed that fraction 11, 15 and 17 correspond to 769 kD, 158 kD and approximately 66 kD, respectively. Note that very-large aggregates were excluded due to a required pre-filter step before SEC to prevent column clogging. HT7 signals in 8-10 fractions (>670 kD) were prominent only in the AD samples. Highest signals of mAb005 was observed in fraction 9, indicating the mAb005 recognizes tau species in a protein complex larger than 670 kD.

Example 8: Immunohistochemical Analysis of PSP and AD Brains

Figure 7A:
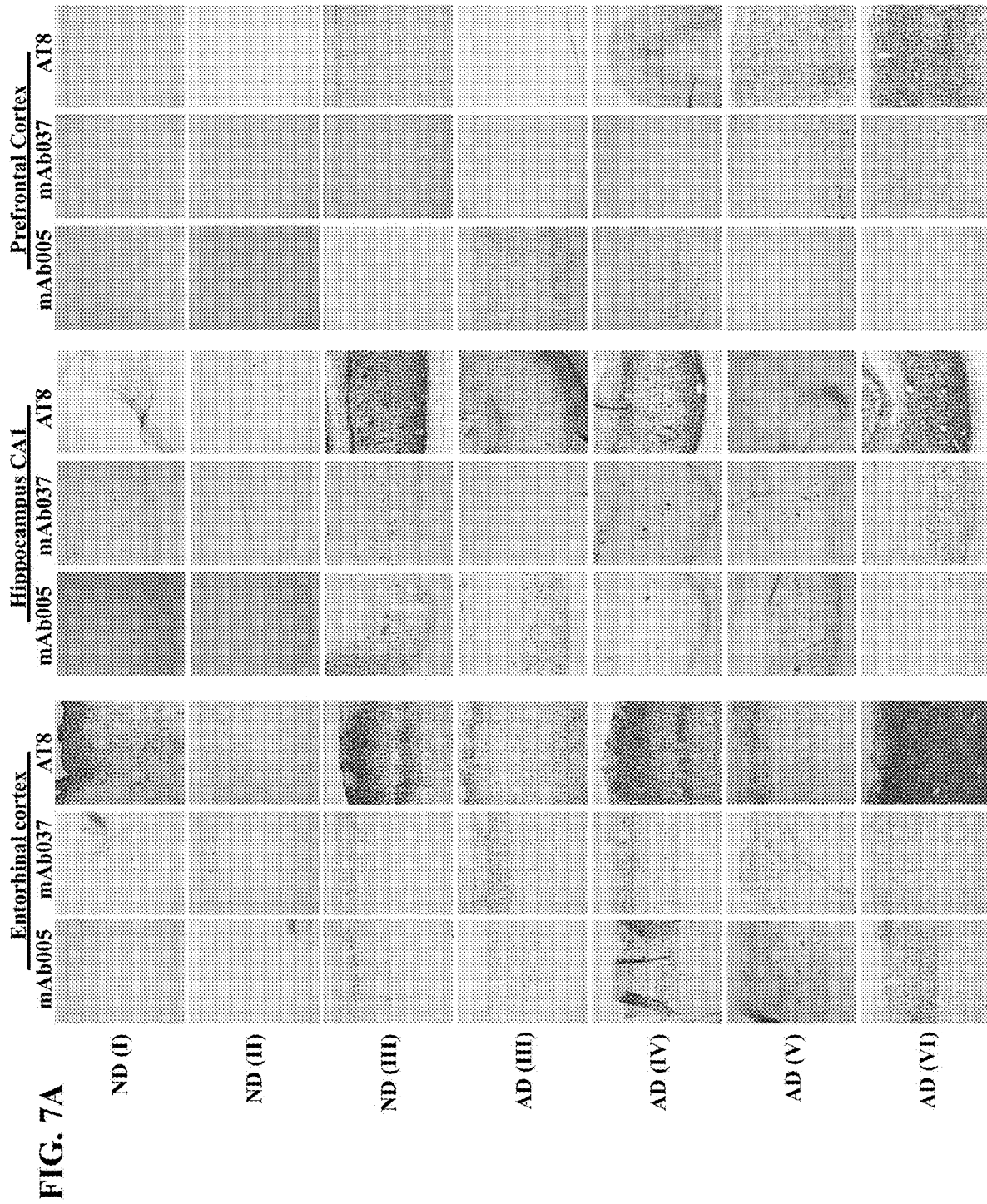
FIG. 7A shows the immunohistochemical (IHC) staining with mAb005 and mAb037 of indicated brain areas of human brain slices with their disease status (ND vs. AD), Braak Stage (I-VI), and patient's identification number (ID) labelled on the top.
Figure 7B:
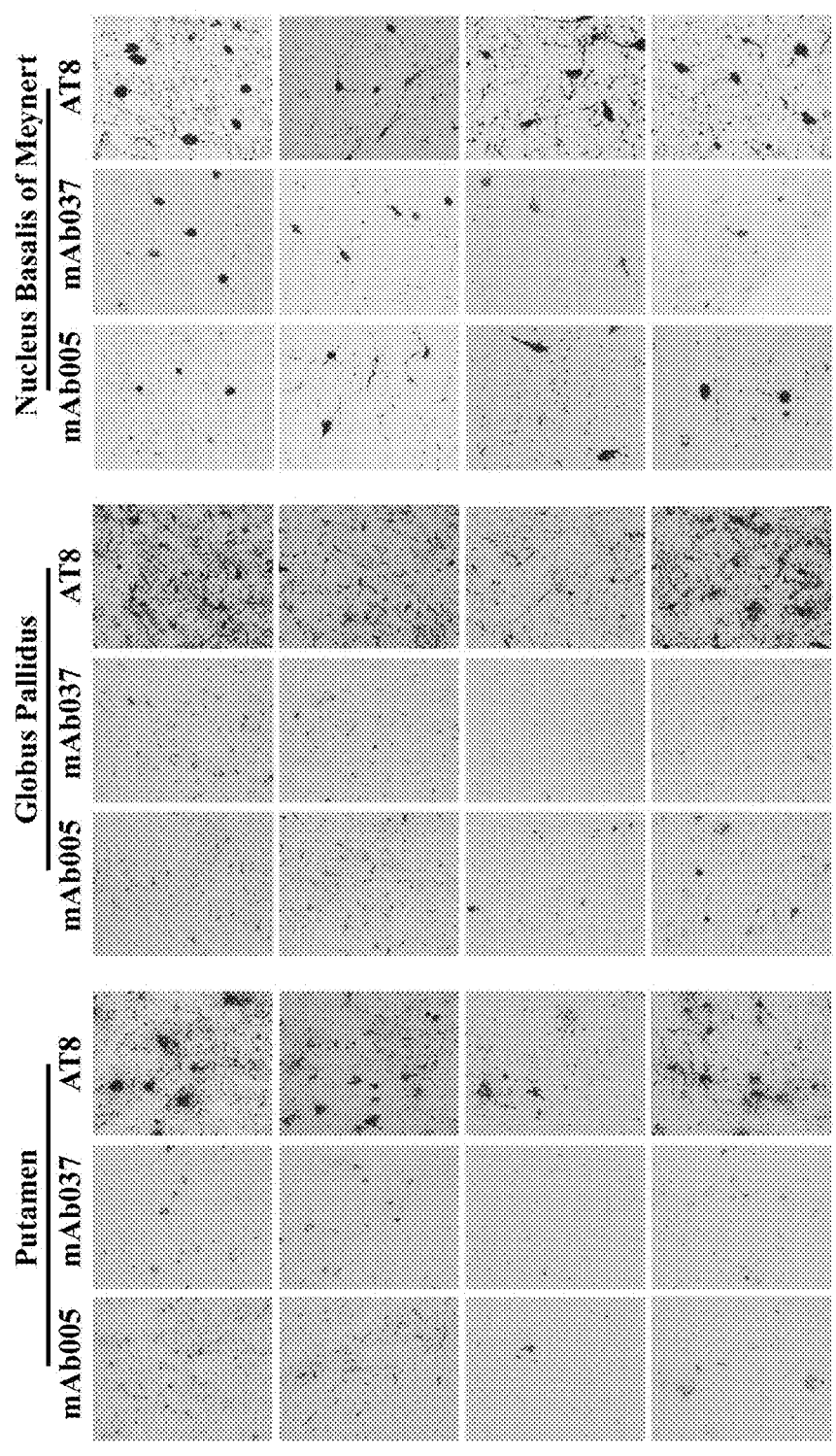
FIG. 7B shows the IHC staining with mAb005 and mAb037 of indicated putamen, globus pallidus and nucleus basalis of Meynert regions of PSP brains.

To determine whether mAb005 and mAb037 could bind to pathological Tau in diseased brains in regional-specific and Braak stage-specific manners, an immunohistochemical analysis was performed in AD and PSP brain slices (conducted at Banner Sun Health Research Institute (AZ, USA)). FIG. 7A shows enlarged photos of indicated brain areas of human brain slices with their disease status (ND vs. AD), Braak Stage (I-VI) and patient's ID labelled on top. mAb005 and mAb037 labelled Tau tangles as shown by purple punctate and diffused signals in all Braak Stages including ND individuals, indicating the ability of mAb005 and mab037 in binding to pathological tau species prior to disease onset. FIG. 7B indicated PSP brain tissues from four patients were all positive for mAb005 and mAb037 signals. Three brain regions include putamen, globus pallidus and nucleus basalis of Meynert were stained to show astrocytes and neurons with tau tangles recognized by mAb005 and mAb037.

Example 9: Selection and Characterization of Humanized mAb005 and mAb037

Figure 8A:
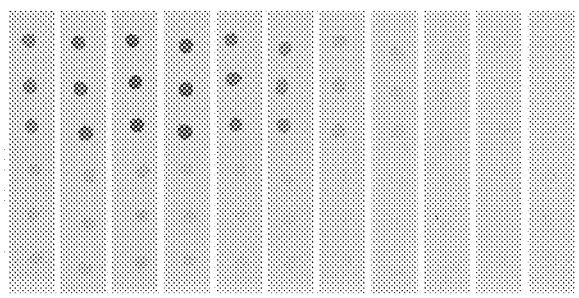
FIG. 8A shows the binding affinity of mouse mAb005 and humanized mAb005 to AD and ND brain homogenate.
Figure 8A:
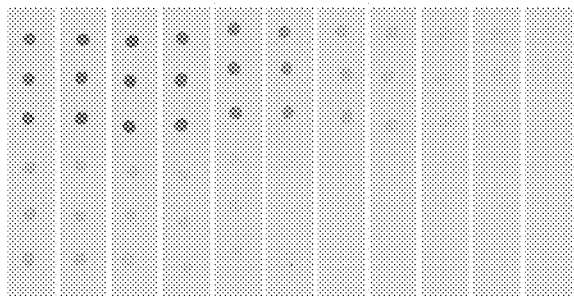
Figure 8A:
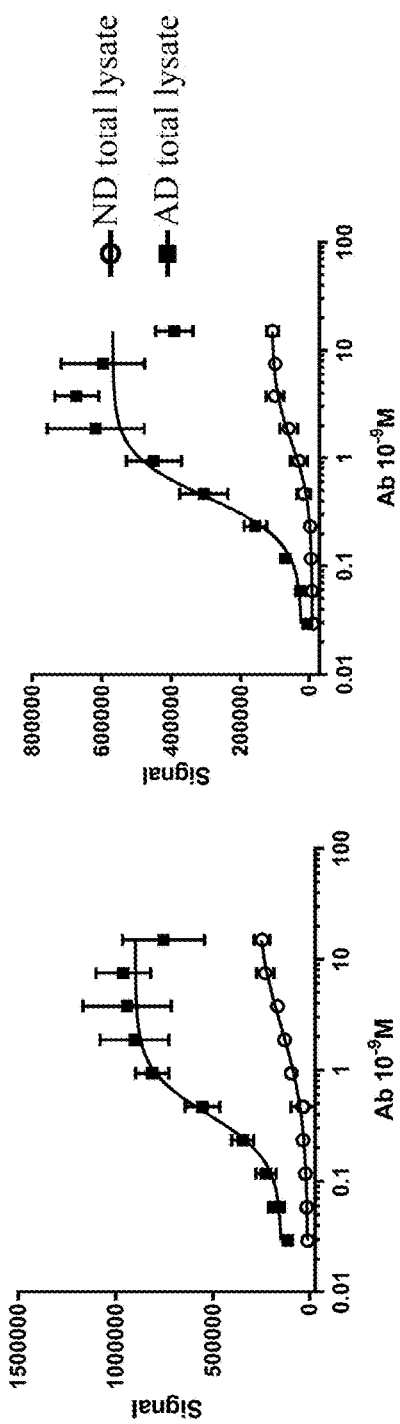
Figure 8B:
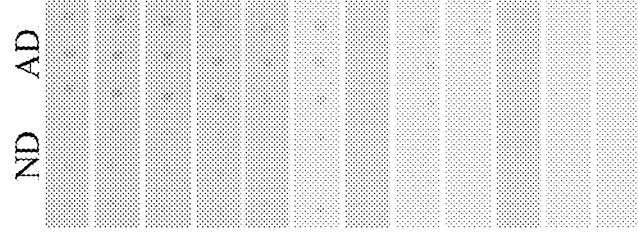
FIG. 8B shows the binding affinity of mouse mAb037 and humanized mAb037 to AD and ND brain homogenate.
Figure 8B:
Figure 8B:
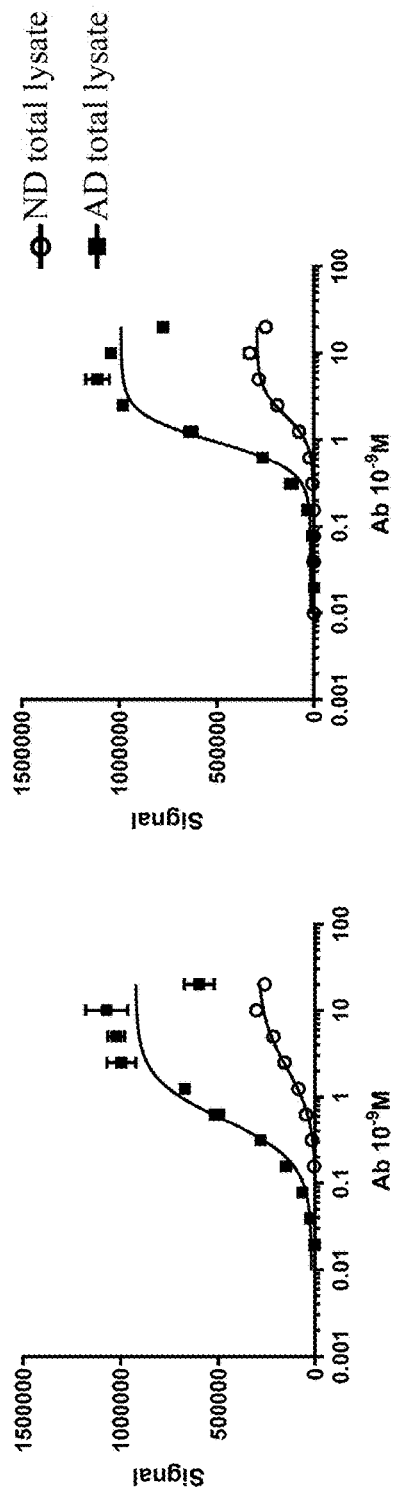

To facilitate the therapeutic potentials of mAb005 and mAb037, humanization of mAb005 and mAb037 was performed by grafting the complementary determining regions (CDRs) of Variable Heavy chain (VH) and Variable Light chain (VL) into a human IgG4 S228P backbone (no Fab-arm exchange mutant, Silva et al., 2015 JBC). Four point-mutations were introduced in the nearby residues surrounding the CDRs to conserve the functionality of the resulting variants. Dot-blot analysis was performed to determine the $EC_{50}$ of each variant, compared with the original mouse/chimeric clones as well as to visualize the specificity to AD Tau protein compared with ND Tau protein. FIGS. 8A and 8B show the binding affinities of mouse mAb005 and mAb037 and humanized variant of mAb005 and mAb037 (as shown in Tables 1-3) to AD and ND brain homogenate. Dot-blot experiments were performed by spotting of ND and AD total brain lysates in triplicate, and antibody solutions were diluted serially by a dilution factor of 2 from a maximum concentration of $6 \times 10^{-8}$ M. Summary graphs denote Mean±SD of 3 independent experiments for mAb005 and Mean±SD of triplicated wells. The results showed that the humanized mAb005 exhibited a binding affinity with an $EC_{50}$ value of $4.3 \times 10^{-10}$ M to AD, which is close to the original mouse clone's $EC_{50}$ value of $4.0 \times 10^{-10}$ M, indicating that the humanized mAb005 maintained the binding affinity and binding specificity in a similar manner to the original mouse clone. The humanized mAb037 exhibited a binding affinity with an $EC_{50}$ value of $9.5 \times 10^{-10}$ M to AD, which is close to the original mouse clone's $EC_{50}$ value of $5.4 \times 10^{-10}$ M, indicating that the humanized mAb037 maintained the binding affinity and binding specificity in a similar manner to the original mouse clone.

Example 10: mAb005 and mAb037 Blocked Tau Seeding Ability

Figure 9:
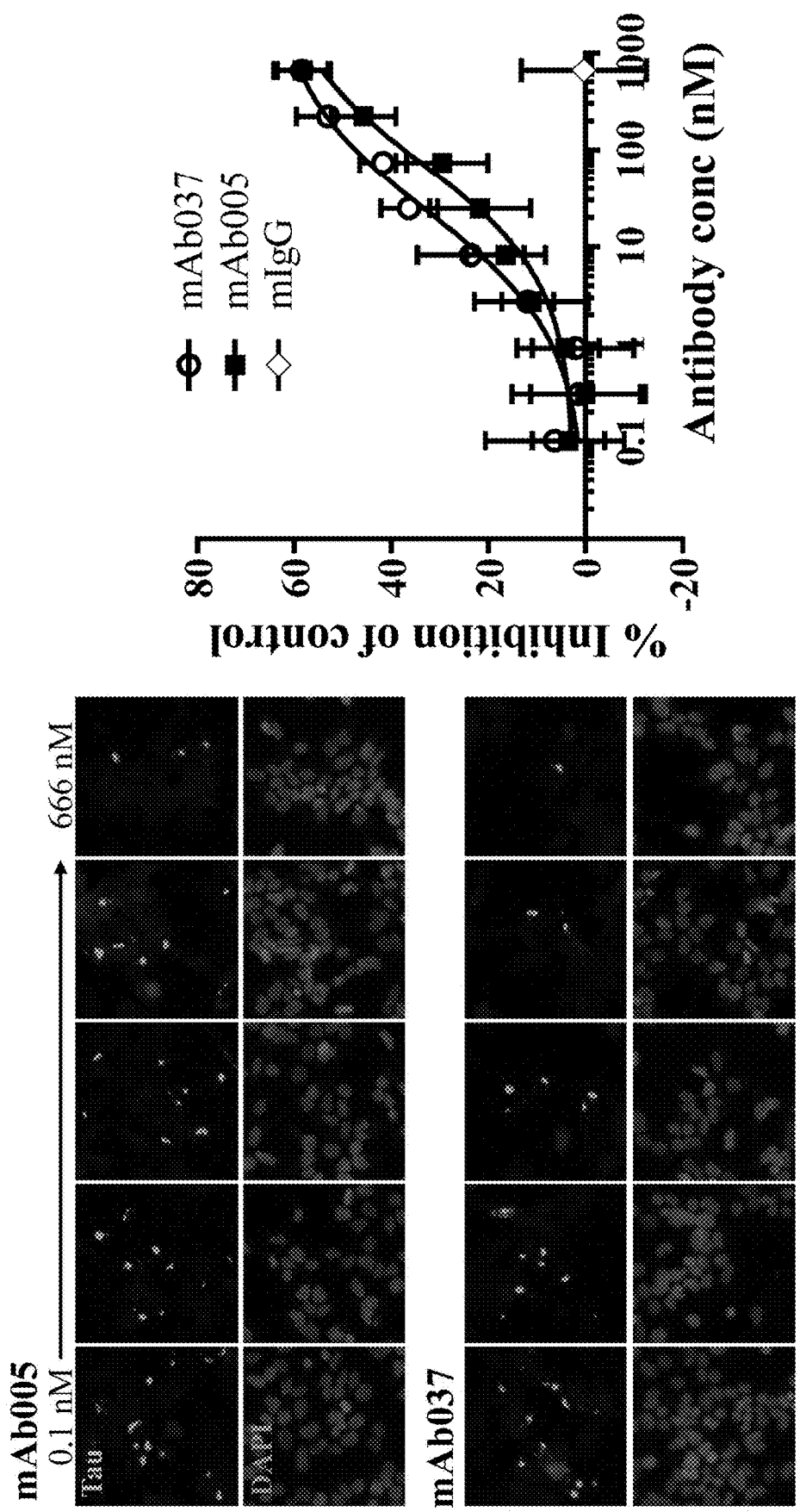
FIG. 9 shows Tau seeding analysis of mAb005 and mAb037.

Because the antibodies described herein, such as mAbs 005, 008, 010, 011, 013, 020, 025, 032 and 037, preferentially recognized synaptic Tau, which is highly associated with Tau-spreading (DeVos et al., 2018 Front Neurosci), Tau seeding assays were performed to determine the effects of mAb005 and mAb037 on Tau seeding propagation. In order to study whether mAb005 and mAb037 can inhibit Tau-propagation, a reporter system was established by stably expressing a 4R repeat domain of mutant Tau (ΔK280/P301L/V337M) tagged with GFP at its N-terminus in HEK293 cells (Tau-LM cell) (Najla., 2012 J Biol Chem). Two-fold serially diluted from 133.3 nM of isotype control mouse IgG, mAb005 or mAb037 were first mixed with 6-month-old rTg4510 brain lysate. Antibody-lysate mixture was incubated with Tau-LM cells for 24 hours. Imaging of Tau-spot formation was performed after lysate was incubated with cells for 48 hours, and cells were fixed and stained with DAPI. The number of Tau spots (represented by GFP-positive signals) and cell number (represented by DAPI-positive spots) were examined by ImageXpress Micro Confocal. The number of Tau spots was normalized by cell number and adjusted by subtracting the value for the "No lysate" condition (N=3, mean±SD). An $EC_{50}$ value of $72.2 \times 10^{-9}$ M for mAb005 and an EC50 value of $22.91 \times 10^{-9}$ M for mAb037 were obtained to quantify the potency of inhibition relative to control IgG sample (FIG. 9). These results suggest that mAb005-recognized Tau and mab037-recognized Tau are highly associated with Tau-propagation.

Figure 10:
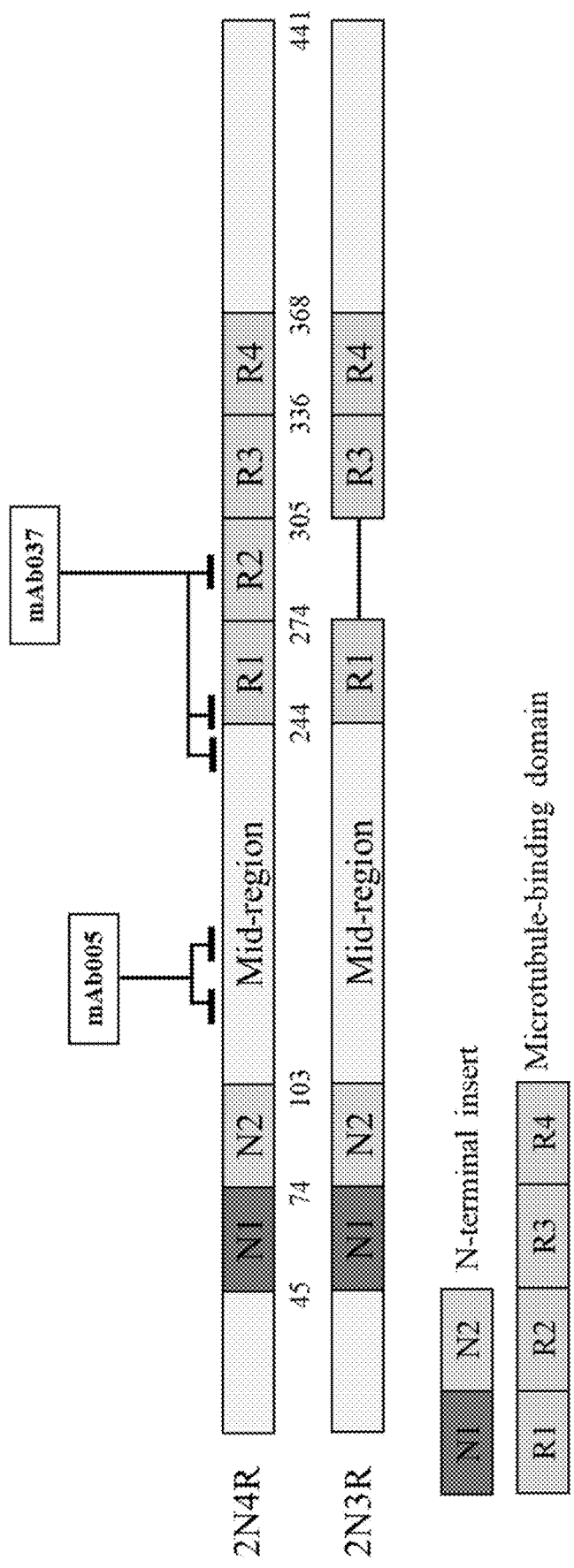
FIG. 10 shows the characterization of mAb005 and mAb037 by conformational epitope mapping using cross-linking coupled mass spectrometry.

Example 11: Characterization of mAb005 and mAb037 by Conformational Epitope Mapping Using Crosslinking Coupled Mass Spectrometry To get an in-depth view for conformational binding motif of mAb005 and mAb037, conformational epitope mapping using crosslinking coupled mass spectrometry was applied to identify conformational epitopes recognized by these anti-Tau antibodies (FIG. 10).

Crosslinking coupled mass spectrometry, performed by CovalX Instrument Incorporated, was applied in the study. Detergent-insoluble Tau aggregates isolated from Alzheimer's patients were used as antigen in the study. Antibodies, mAb005 and mAb037, respectively, and Tau aggregates were incubated with deuterated cross-linker. Since after crosslinking chemistry the antibody/antigen complex was extremely stable, multiple enzymes (five utilized in parallel) and digestion conditions were applied to the complex to provide many different overlapping peptides. Identification of the peptides was performed using high-resolution Orbitrap™ mass spectrometry and MS/MS techniques. The identification of the crosslinked peptides was determined using mass tags linked to the crosslinking reagents. After MS/MS fragmentation, data generated were analyzed using XQuest and Stavros softwares.

Results showed that mAb005 and mAb037 bind to a region of polypeptides located the mid-region and microtubule binding domain of Tau. Specifically, mAb005 binds to a domain comprising the amino acids S131, K132, T135, S137 and R155 in a human 2N4R Tau isoform, and mAb037 binds to a domain comprising the amino acids R230, T231, S237, T245, K281 and S289 in a human 2N4R Tau isoform.

Example 12: APNmAb005 In Vivo Efficacy Assay

Figure 11A:
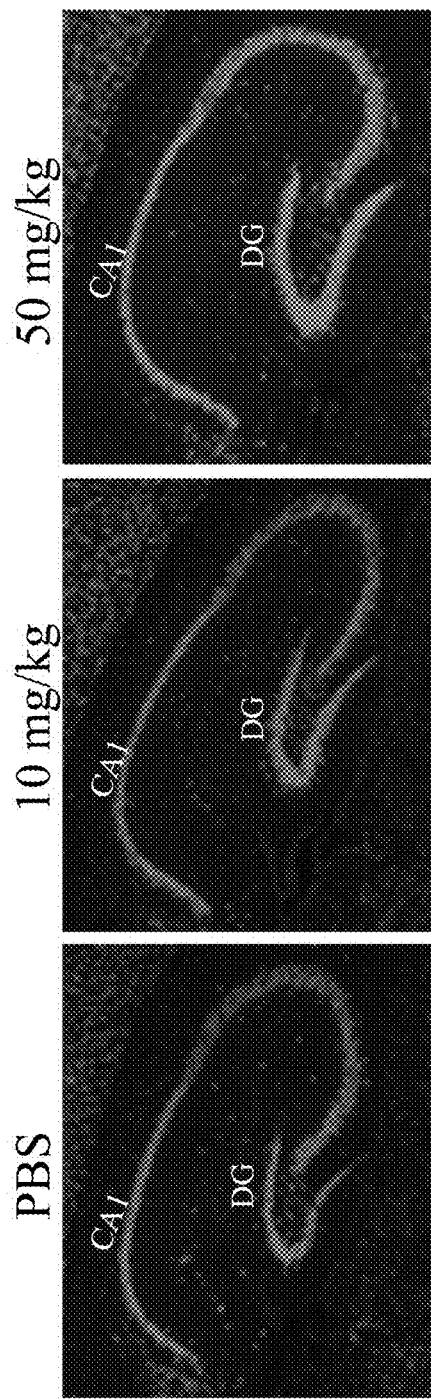
FIG. 11A shows APNmAb005 in vivo efficacy study demonstrating the reduction of neuronal loss in the hippocampal sub-regions CA1 and Dentate Gyms (DG) in the 50 mg/kg-treated group.
Figure 11A:
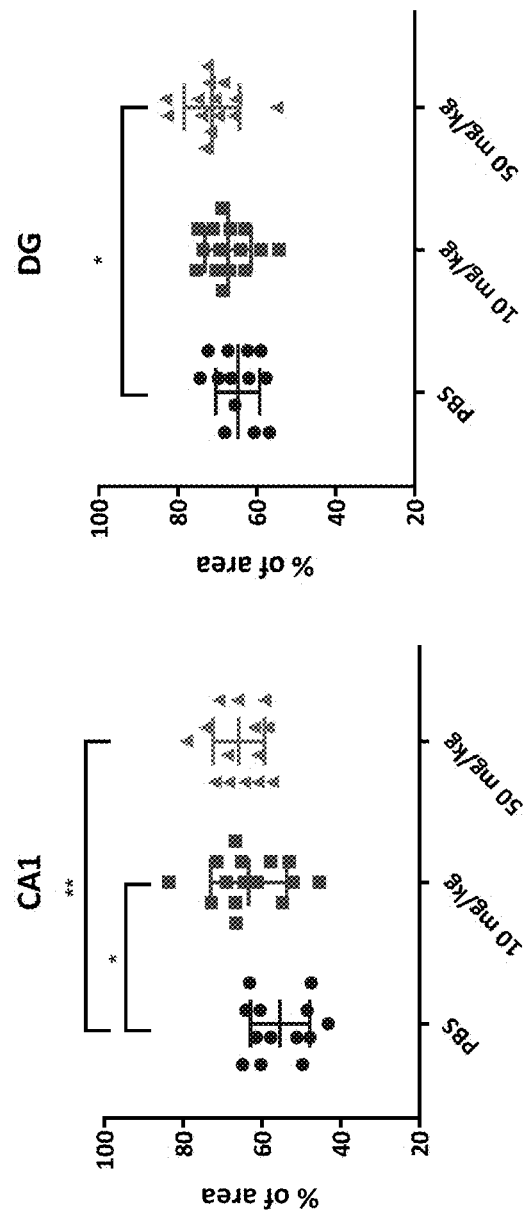
Figure 11B:
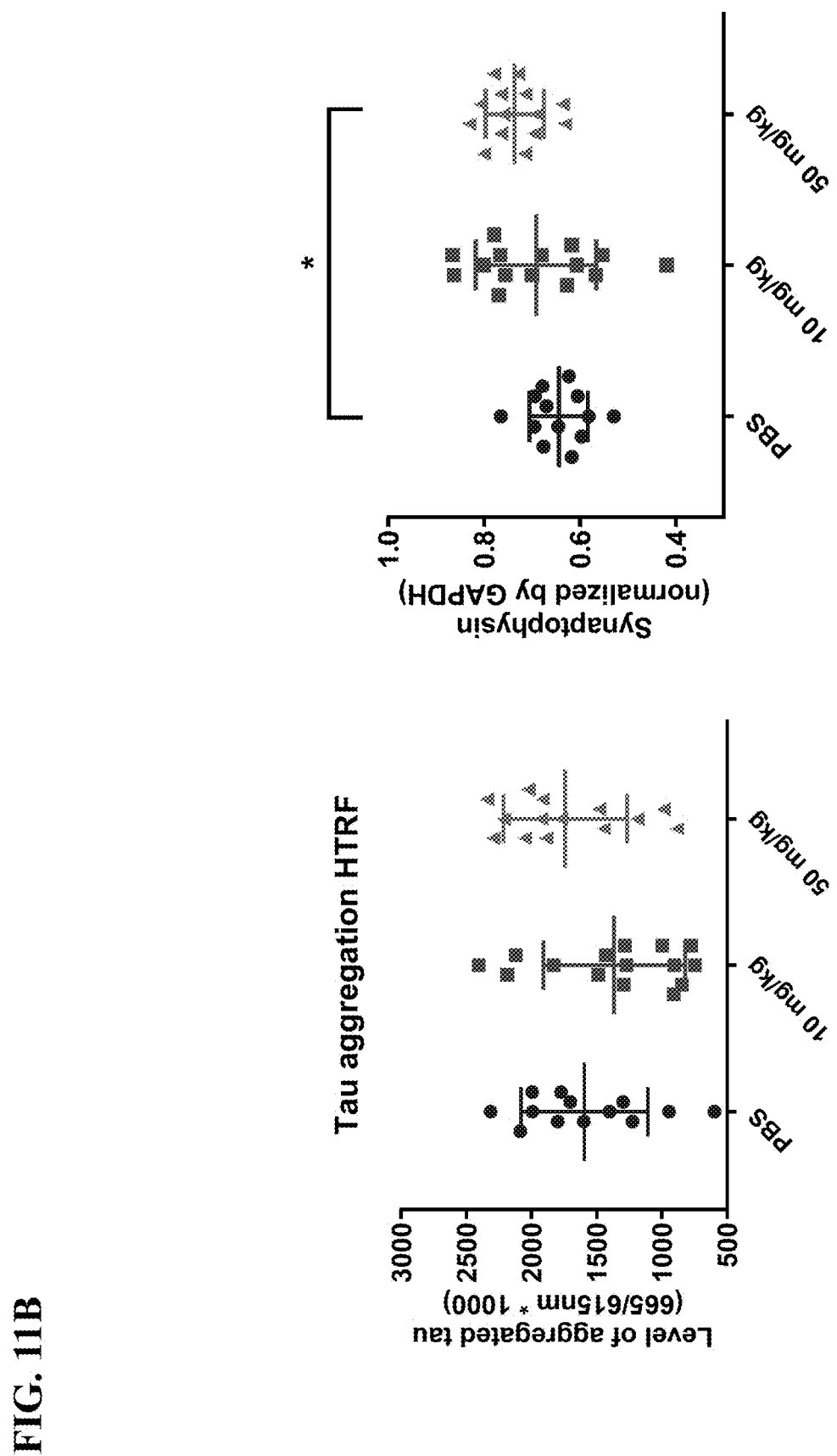
FIG. 11B shows the analysis of Tau aggregation status by HTRF assay (left) and the analysis of synapse counts measured by the level of synaptophysin.

Method: To assess whether APNmAb005 can alter tau aggregation and ameliorate the neuronal loss in rTg4510 mice, rTg4510 mice at 3.5-month-old were treated with intraperitoneal injection of the mouse IgG1 version of APNmAb005. Ten and 50 mg/kg of antibody were administered once per week for 12 weeks. Whole brains were collected at 13 weeks and separated into 2 halves for biochemistry and immunohistochemistry analyses. For immunohistochemistry analysis, half brains were fixed and sagittally sectioned. Numbers of neurons were quantified in CA1 and Dentate Gyms (DG) by counting the numbers of NeuN-stained signals normalized by area (FIG. 11A). For biochemistry analysis, half brains were quickly homogenized and subjected for the Homogeneous Time Resolved Fluorescence (HTRF) assay (CisBio) developed to quantify the amount of aggregated tau protein (FIG. 11B left). Moreover, some extracts were used in a dot-blot assay labeled by a presynaptic marker, synaptophysin, to assess the amount of the synapses.

Results: In FIG. 11A, significant rescue of neuronal loss in both CA1 and DG was observed for the 50 mg/kg group. Consistent with this observation, significant increase of synapse level was observed as well for the 50 mg/kg group (FIG. 11B right). However, no clear reduction of aggregated tau proteins was found (FIG. 11B left), indicating the APNmAb005 might act as a blocking antibody instead of clearing tau aggregates.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

SEQUENCE LISTING

| SEQ ID NO | Sequence | Description |
|---|---|---|
| 1 | EVQLVESGGDLVESGGSLKLSCAASGFTFSSYGMSWVRQTPDKRLEWVATISSSG SYTYYPDSVKGRFTISRDNAKNTLYLQMSSLNSEDTAMYYCADTYYGAMDYWGQ GTSVTVSS | Mouse mAb004 heavy chain AA sequence |
| 2 | EVQLVESGGGLVKPGGSLKLSCAASGFTFSDYGMHWVRQAPEKGLEWVAYSNSD STTIYYADTVKGRFTISRDNAKSTLFLQMTSLRSEDTAMYYCGRSYYSNYVDYWGQ GTTLTVSS | Mouse mAb005 heavy chain AA sequence |
| 3 | EVQLVESGGGLVQPGGSLRLSCAASGFTFSDYGMHWVRQAPGKGLEWVAYSNS DSTTIYYADTVKGRFTISRDNAKNSLYLQMNSLRAEDTAVYYCGRSYYSNYVDYW GQGTLVTVSS | Humanized mAb005 heavy chain AA sequence |
| 4 | EVKLLQSGGGLVQPGGSLKVSCAASGFDFSRYWMSWVRRAPGKGLEWIGEINPD GNAINYAPSLKDKFIVSRDNAKNTLYLQMSNVRSEDTALYYCARPFPSVWGTGTT VTVSS | Mouse mAb008 heavy chain AA sequence |
| 5 | QVQLKESGPGLVAPSQSLSITCTVSGFSLTGYGVNWVRQPPGKGLEWLGMIWGD GSTDYNSALKSRLSISKDNSKSQVFLKMNSLQTDDTARYYCANWAFAYWGQGTL VTVSA | Mouse mAb010 heavy chain AA sequence |
| 6 | QVQLQQSGPQLVRPGASVKISCKASGYSFTSYWMHWLKQRPGQGLEWIGMIDP SDSETRLNQKFKDKATLTVDKSSSTVYMHLSSPTSEDSAVYYCVRPYGDLDYWGQ GTTLTVSS | Mouse mAb011 heavy chain AA sequence |
| 7 | EVQLQQSGPELVKPGASVKMSCKASGYTFTDFYMKWVKQSHGKSFEWIGDIDPN NGDTFYNQKFKGKATLTVDKSSSTAYMQLNSLTSEDSAVYYCARDLYWGQGTTLT VSS | Mouse mAb013 heavy chain AA sequence |
| 8 | QVQLKQSGPGLVQPSQSLSITCTVSGFSLTSYAVHWVRQSPGKGLEWLGVMWS GGSTDYNAAFISRLSISKDNSKSQVFFKMNSLQADDTAIYYCARMGDYDGVAWF AYWGQGTLVTVSA | Mouse mAb020 heavy chain AA sequence |
| 9 | QIQLVQSGPELKKPGETVKISCKASGYTFTTHGMSWVKQAPGKGLKWMGWINT YSGVPTYTDDFKGRFAFSLETSASTAYLQINNLKNEDTATYFCARSELSWFAYWGQ GTLVTVSA | Mouse mAb025 heavy chain AA sequence |
| 10 | QVQLQQSGAELVKPGASVKISCKASGYAFSSYWMNWVKQRPGKGLEWIGQIYP GDGDTDYNGKFKGKATLTADTSSSTAYMQLSSLTSEDSAVYFCASRSPYWGQGTL VTVSA | Mouse mAb032 heavy chain AA sequence |
| 11 | QVTLKESGPGILQPSQTLSLTCSFSGFSLSTFGMGVGWFRQPSGKGLEWLAHIW WDDDKYYNPALKSRLTISKDTSKNQVFLKIANVDTADTATYYCARRGSNALDYWG QGTSVTVSS | Mouse mAb033 heavy chain AA sequence |
| 12 | EVQLQQSGPELVKPGASVKIPCKASGYTFTDYNMDWVKQSHGKSLEWIGDINPN TGGTIYNQKFKGKATLTVDKSSSTAYMELRSLTSEDTAVYYCAGEGPYYYGTTHPF AYWGQGTLVTVSA | Mouse mAb037 heavy chain AA sequence |
| 106 | QVQLVQSGAEVKKPGASVKVSCKASGYTFTDYNMDWVRQAHGQGLEWIGDIN PNTGGTIYNQKFKGRATLTVDTSISTAYMELSRLRSDDTAVYYCAGEGPYYYGTTH PFAYWGQGTLVTVSS | Humanized mAb037 heavy chain AA sequence |
| 13 | DVLMTQTPLSLPVSLGDQASISCRSSQTIVHSNGNTYLEWYLQKPGQSPKLLIYKVS NRFSGVPDRFSGSGSGTDFTLKISRVEAEDLGVYYCFQGSLVPWTFGGGTQLEIR | Mouse mAb004 light chain AA sequence |
| 14 | DIVMTQIPLSLPVSLGDQASISCRSSQSLVHSNGNTYLHWYLQKPGQSPKLLIYKVS NRFSGVPDRFSGSGSGTDFTLKISRVEAEDLGVYFCFQSTHVPPTFGGGTKLEIK | Mouse mAb005 light chain AA sequence |
| 15 | DVVMTQSPLSLPVTLGQPASISCRSSQSLVHSNGNTYLHWYLRPGQSPRLLIYKV SNRFSGVPDRFSGSGSGTDFTLKISRVEAEDVGVYFCFQSTHVPPTFGQGTKLEIK | Humanized mAb005 light chain AA sequence |
| 16 | DVLMTQTPLSLPVSLGDQASISCRSSQSLVRSNGNTYLEWYLQNPGQSPKLLIYKV SNRFSGVPDRFSGSGSGTDFTLKISRVEAEDLGVYYCFQGSHVPYTFGGGTKLEIK | Mouse mAb008 light chain AA sequence |
| 17 | DVVMTQTPLTLSVTIGQPASISCKSSQSLLDSGGKTYLNWLLQRPGQSPKRLIYQVS KLDSGVPDRFTGSGSGTDFTLKISRVEAEDLGVYYCWQGTHFPLTFGAGTKLELK | Mouse mAb010 light chain AA sequence |
| 18 | DVVMTQTPLTLSVTIGQPASISCKSSQSLLDSDGKTYLNWLLQRPGQSPKRLIYLVS KLDSGVPDRFTGSGSGTDFTLKISRVEAEDLGVYYCWQGTHFPFTFGSGTKLEIK | Mouse mAb011 light chain AA sequence |
| 19 | DVVMTQTPLTLSVTIGQPASISCKSSQSLLYSNGKTYLNWLLQRPGQSPKRLIYLVS KLDSGVPDRFTGSGSGTDFTLKISRVEAEDLGVYYCVQGTHFPHTFGGGTKLEIK | Mouse mAb013 light chain AA sequence |
| 20 | DVVMTQTPLSLPVSLGDQASISCRSSQSLVHSNGNTYLHWYLQKPGQSPKLLIYKV SNRFSGVPDRFSGSGSGTDFTLKISRVEAEDLGVYFCSQSTHVPPWTFGGGTKLEIK | Mouse mAb020 light chain AA sequence |

| SEQ ID NO | Sequence | Description |
|---|---|---|
| 21 | DIVMTQSPATLSVTPGDRVSLSCRASQSISDYLHWYQQKSHESPRLLIKYASQSISGI PSRFSGSGSGSDFTLSINSVEPEDVGVYYCQNGHSFPYTFGGGTKLEIK | Mouse mAb025 light chain AA sequence |
| 22 | DILMTQTPLSLPVSLGDQASISCRSSQSIVHSNGNTYLEWYLQKPGQSPKLLIYKVS NRFSGVPDRFSGSGSGTDFTLKISRVEAEDLGVYYCFQGSHVPYTFGGGTKLEIK | Mouse mAb032 light chain AA sequence |
| 23 | DVVVTQTPLSLPVSFGDQVSISCRSSQSLANSYGNTYLSWYLHKPGQSPQLLIYGIS NRFSGVPDRFSGSGSGTDFTLKISTIKPEDLGMYYCLQGTHQPWTFGGGTKLEIK | Mouse mAb033 light chain AA sequence |
| 24 | DVVMTQTPLTLSVTIGQPASISCKSSQSLLYSNGKTYLNWLLQRPGQSPKRLIYLVS KLDSGVPDRFTGSGSGTDFTLKISRVEAEDLGVYYCVQGTHFPQTFGGGTKLEIK | Mouse mAb037 light chain AA sequence |
| 107 | DVVMTQSPLSLPVTLGQPASISCKSSQSLLYSNGKTYLNWLLQRPGQSPRRLIYLVS KLDSGVPDRFSGSGSGTDFTLKISRVEAEDVGVYYCVQGTHFPQTFGGGTKLEIK | Humanized mAb037 light chain AA sequence |
| 25 | GAGGTGCAGCTGGTGGAGTCTGGGGGAGACTTAGTGGAGTCTGGAGGGTCC CTAAAACTCTCCTGTGCAGCCTCTGGATTCACTTTCAGTAGCTATGGCATGTCTT GGGTTCGCCAGACTCCAGACAAGAGGCTGGAGTGGGTCGCAACCATTAGTAG TAGTGGTAGTTACACCTACTATCCAGACAGTGTGAAGGGGCGATTCACCATCT CCAGAGACAATGCCAAGAACACCCTGTACCTGCAAATGAGCAGTCTGAACTCT GAGGACACAGCCATGTATTACTGTGCTGATACTTACTACGGAGCTATGGACTA CTGGGGTCAAGGAACCTCAGTCACCGTCTCCTCA | Mouse mAb004 heavy chain DNA sequence |
| 26 | GAGGTGCAGCTGGTGGAGTCTGGGGGAGGCTTAGTGAAGCCTGGAGGGTCC CTGAAACTCTCCTGTGCAGCCTCTGGATTCACTTTCAGTGACTATGGAATGCAC TGGGTTCGTCAGGCTCCAGAGAAGGGGCTGGAGTGGGTTGCATACAGCAATA GTGACAGTACTACCATCTACTATGCAGACACAGTGAAGGGCCGATTCACCATC TCCAGAGACAATGCCAAGAGCACCCTGTTCCTGCAAATGACCAGTCTGAGGTC TGAGGACACGGCCATGTATTATTGTGGAAGGAGCTACTATAGTAACTACGTTG ACTACTGGGGCCAAGGCACCACTCTCACAGTCTCCTCA | Mouse mAb005 heavy chain DNA sequence |
| 27 | GAGGTGCAGCTGGTTGAATCTGGCGGAGGACTGGTTCAGCCTGGCGGATCTC TGAGACTGTCTTGTGCCGCCAGCGGCTTCACCTTCAGCGATTATGGCATGCACT GGGTCCGACAGGCCCCTGGCAAAGGACTTGAGTGGGTCGCCTACAGCAACAG CGACAGCACCACCATCTACTACGCCGACACCGTGAAGGGCAGATTCACCATCA GCCGGGACAACGCCAAGAACAGCCTGTACCTGCAGATGAACTCCCTGAGAGC CGAGGACACCGCCGTGTACTACTGTGGCAGAAGCTACTACTCCAACTACGTGG ACTACTGGGGCCAGGGCACACTGGTCACAGTGTCTAGC | Humanized mAb005 heavy chain DNA sequence |
| 28 | GAGGTGAAGCTTCTCCAGTCTGGAGGTGGCCTGGTGCAGCCTGGAGGATCCC TGAAAGTCTCCTGTGCAGCCTCAGGATTCGATTTTAGTAGATACTGGATGAGTT GGGTTCGGCGGGCTCCAGGAAAAGGACTAGAGTGGATTGGAGAAATTAATCC AGATGGCAATGCAATAAAACTATGCACCATCTCTAAAGGATAAATTCATCGTCTC CAGAGACAACGCCAAAAATACGCTGTACCTGCAAATGAGCAATGTGAGATCTG AGGACACAGCCCTTTATTACTGTGCACGACCTTTCCCCAGCGTCTGGGGCACA GGGACCACGGTCACCGTCTCCTCA | Mouse mAb008 heavy chain DNA sequence |
| 29 | CAGGTGCAGCTGAAGGAGTCAGGACCTGGCCTGGTGGCGCCCTCACAGAGCC TGTCCATCACATGCACCGTCTCAGGGTTCTCATTAACCGGCTATGGTGTAAACT GGGTTCGCCAGCCTCCAGGAAAGGGTCTGGAGTGGCTGGGAATGATATGGGG TGATGGAAGCACAGACTATAATTCAGCTCTCAAATCCAGACTGAGCATCAGCA AGGACAACTCCAAGAGCCAAGTTTTCTTAAAAATGAATAGTCTGCAAACTGAT GACACAGCCAGGTACTACTGTGCCAACTGGGCCTTTGCTTACTGGGGCCAAGG GACTCTGGTCACTGTCTCTGCA | Mouse mAb010 heavy chain DNA sequence |
| 30 | CAGGTGCAACTGCAGCAGTCTGGGCCTCAGCTGGTTAGGCCTGGGGCTTCAGT GAAGATATCCTGCAAGGCTTCTGGTTACTCATTCACCAGCTACTGGATGCACTG GCTGAAGCAGAGGCCTGGACAAGGTCTTGAGTGGATTGGCATGATTGATCCTT CCGATAGTGAAACTAGGTTAAATCAGAAGTTCAAGGACAAGGCCACATTGACT GTAGACAAATCCTCCAGTACAGTCTACATGCACCTCAGCAGCCCGACATCTGA GGACTCTGCGGTCTATTACTGTGTAAGGCCGTATGGTGACCTTGACTACTGGG GCCAAGGCACCACTCTCACAGTCTCCTCA | Mouse mAb011 heavy chain DNA sequence |
| 31 | GAGGTCCAGCTGCAACAGTCTGGACCTGAGCTGGTGAAGCCTGGGGCTTCAG TGAAGATGTCCTGCAAGGCTTCTGGATACACCTTCACTGACTTCTACATGAAGT GGGTGAAGCAGAGCCATGGAAAGAGCTTTGAGTGGATTGGAGATATTGATCC TAACAATGGTGATACTTTCTACAACCAGAAGTTCAAGGGCAAGGCCACATTGA CTGTAGACAAATCCTCCAGCACAGCCTACATGCAGCTCAACAGCCTGACATCTG AGGACTCTGCAGTCTATTACTGTGCAAGGGATCTCTACTGGGGCCAAGGCACC ACTCTCACAGTCTCCTCA | Mouse mAb013 heavy chain DNA sequence |

SEQUENCE LISTING

| SEQ ID NO | Sequence | Description |
|---|---|---|
| 32 | CAGGTGCAGCTGAAGCAGTCAGGACCTGGCCTAGTGCAGCCCTCACAGAGCCT GTCCATCACCTGCACAGTCTCTGGTTTCTCATTAACTAGTTATGCTGTACACTGG GTTCGCCAGTCTCCAGGAAAGGGTCTGGAGTGGCTGGGAGTGATGTGGAGTG GTGGAAGCACAGACTATAATGCAGCTTTCATATCCAGACTGAGCATCAGCAAG GACAATTCCAAGAGCCAAGTTTTCTTTAAAATGAACAGTCTGCAAGCTGATGAC ACAGCCATATATTACTGTGCCAGAATGGGTGATTACGACGGGGTGGCCTGGTT TGCTTACTGGGGCCAAGGGACTCTGGTCACTGTCTCTGCA | Mouse mAb020 heavy chain DNA sequence |
| 33 | CAGATCCAGTTGGTACAGTCTGGACCTGAGCTGAAGAAGCCTGGAGAGACAG TCAAGATCTCCTGCAAGGCTTCTGGGTATACCTTTACAACCCATGGAATGAGCT GGGTGAAACAGGCTCCAGGAAAGGGTTTAAAGTGGATGGGCTGGATAAACAC CTACTCTGGAGTGCCAACATATACTGATGACTTCAAGGGACGGTTTGCCTTCTC TTTGGAAACCTCTGCCAGCACTGCCTATTTGCAGATCAACAACCTCAAAAATGA GGACACGGCTACATATTTCTGTGCAAGATCAGAACTGTCCTGGTTTGCTTACTG GGGCCAAGGGACTCTGGTCACTGTCTCTGCA | Mouse mAb025 heavy chain DNA sequence |
| 34 | CAGGTTCAGCTGCAGCAGTCTGGGGCTGAGCTGGTGAAGCCTGGGGCCTCAG TGAAGATTTCCTGCAAAGCTTCTGGCTACGCATTCAGTAGCTACTGGATGAACT GGGTGAAGCAGAGGCCTGGAAAGGGTCTTGAGTGGATTGGACAGATTTATCC TGGAGATGGTGATACTGATTACAACGGAAAGTTCAAGGGCAAGGCCACACTG ACTGCAGACACATCCTCCAGCACAGCCTACATGCAGCTCAGCAGCCTGACCTCT GAGGACTCTGCGGTCTATTTCTGTGCAAGCCGATCCCCTTACTGGGGCCAAGG GACTCTGGTCACTGTCTCTGCA | Mouse mAb032 heavy chain DNA sequence |
| 35 | CAGGTTACTCTGAAAGAGTCTGGCCCTGGGATATTGCAGCCCTCCCAGACCCT CAGTCTGACTTGTTCTTTCTCTGGGTTTTCACTGAGCACTTTTGGTATGGGTGTA GGCTGGTTTCGTCAGCCTTCAGGGAAGGGTCTGGAGTGGCTGGCACACATTTG GTGGGATGATAAGTACTATAACCCAGCCCTGAAGAGTCGGCTCACAATCT CCAAGGATACCTCCAAAAACCAGGTTTTCCTCAAGATCGCCAATGTGGACACT GCAGATACTGCCACATACTACTGTGCTGAAGGGGTAGTAATGCTCTGGACTA CTGGGGTCAAGGAACCTCAGTCACCGTCTCCTCA | Mouse mAb033 heavy chain DNA sequence |
| 36 | GAGGTCCAGCTGCAACAGTCTGGACCTGAGCTGGTGAAGCCTGGGGCTTCAG TGAAGATACCCTGCAAGGCTTCTGGATACACATTCACTGACTACAACATGGACT GGGTGAAGCAGAGCCATGGAAAGAGCCTTGAGTGGATTGGAGATATTAATCC TAACACTGGTGGTACTATCTACAACCAGAAGTTCAAGGGCAAGGCCACATTGA CTGTAGACAAGTCCTCCAGCACAGCCTACATGGAGCTCCGCAGCCTGACATCT GAGGACACTGCAGTCTATTACTGTGCAGGAGAGGGCCCTTATTACTACGGTAC TACCCACCCTTTTGCTTACTGGGGCCAAGGGACTCTGGTCACTGTCTCTGCA | Mouse mAb037 heavy chain DNA sequence |
| 108 | CAAGTGCAGCTGGTCCAGAGCGGCGCCGAGGTGAAAAAGCCCGGCGCCAGC GTGAAGGTGTCTTGTAAAGCCTCTGGCTACACCTTCACCGACTACAACATGGA CTGGGTGCGGCAGGCCCACGCCAGGGCCTGGAATGGATCGGCGACATCAAC CCCAACACCGGCGAACAATCTACAACCAGAAGTTCAAGGGCAGAGCCACCCT GACAGTGGACACCAGCATCAGCACCGCCTACATGGAACTGAGCAGACTGAGA AGCGACGACACAGCCGTGTACTACTGCGCCGGCGAGGGCCCTTACTACTACGG CACGACCCACCCCTTCGCCTACTGGGGCCAGGGCACACTGGTGACCGTGTCCA GC | Humanized mAb037 heavy chain DNA sequence |
| 37 | GATGTTTTGATGACCCAAACTCCACTCTCCCTGCCTGTCAGTCTTGGAGATCAA GCCTCCATCTCTTGCAGATCTAGTCAGACCATTGTACATAGTAATGGAAACACC TATTTAGAATGGTACCTGCAGAAACCAGGCCAGTCTCCAAAGCTCCTGATCTAC AAAGTTTCCAACCGATTTTCTGGGGTCCCAGACAGGTTCAGTGGCAGTGGATC AGGGACAGATTTCACACTCAAGATCAGCAGAGTGGAGGCTGAGGATCTGGGA GTTTATTACTGCTTTCAAGGTTCACTTGTTCCGTGGACGTTCGGTGGAGGCACC CAGCTGGAAATCAGG | Mouse mAb004 light chain DNA sequence |
| 38 | GATATTGTGATGACCCAAATTCCACTCTCCCTGCCTGTCAGTCTTGGAGATCAA GCCTCCATCTCTTGCAGATCTAGTCAGAGCCTTGTACACAGTAATGGAAACACC TATTTACATTGGTACCTGCAGAAGCCAGGCCAGTCTCCAAAGCTCCTAATCTAC AAAGTTTCCAACCGATTTTCTGGGGTCCCAGACAGGTTCAGTGGCAGTGGATC AGGGACAGATTTCACACTCAAGATCAGCAGAGTGGAGGCTGAGGATCTGGGA GTTTATTTCTGCTTTCAAAGTACACATGTTCCTCCGACGTTCGGTGGAGGCACC AAGCTGGAAATCAAA | Mouse mAb005 light chain DNA sequence |
| 39 | GACGTGGTCATGACACAGAGCCCTCTGAGCCTGCCTGTGACACTGGGACAGCC TGCCAGCATCAGCTGTAGAAGCAGCCAGAGCCTGGTGCACAGCAACGGCAAT ACCTACCTGCACTGGTATCTGCAGAGGCCCGGACAGTCTCCCAGACTGCTGAT CTACAAGGTGTCCAACCGGTTCAGCGGCGTGCCCGATAGATTTTCTGGCAGCG GCTCTGGCACCGACTTCACCCTGAAGATCTCCAGAGTGGAAGCCGAGGACGTG GGCGTGTACTTCTGCTTCCAAAGCACCCACGTGCCACCTACCTTTGGCCAGGGC ACCAAGCTGGAAATCAAG | Humanized mAb005 light chain DNA sequence |

SEQUENCE LISTING

| SEQ ID NO | Sequence | Description |
|---|---|---|
| 40 | GATGTTTTGATGACCCAAACTCCACTCTCCCTGCCTGTCAGTCTTGGAGATCAA GCCTCCATCTCTTGCAGATCTAGTCAGAGTCTTGTACGTAGTAATGGAAACACC TATTTAGAATGGTACCTGCAGAACCCAGGCCAGTCTCCAAAGCTCCTGATCTAC AAAGTTTCCAACCGATTTTCTGGGGTCCCAGACAGGTTCAGTGGCAGTGGATC AGGGACAGATTTCACACTCAAGATCAGCAGAGTGGAGGCTGAGGATCTGGGA GTTTATTACTGCTTTCAAGGTTCACATGTTCCGTACACGTTCGGAGGGGGGACC AAGCTGGAAATAAAA | Mouse mAb008 light chain DNA sequence |
| 41 | GATGTTGTGATGACCCAGACTCCACTCACTTTGTCGGTTACCATTGGACAACCA GCCTCCATCTCTTGTAAGTCAAGTCAGAGCCTCTTAGATAGTGGTGGAAAGAC ATATTTGAATTGGTTGTTACAGAGGCCAGGCCAGTCTCCAAAGCGCCTAATCTA TCAGGTGTCTAAACTGGACTCTGGAGTCCCTGACAGGTTCACTGGCAGTGGAT CAGGGACAGATTTCACACTGAAAATCAGCAGAGTGGAGGCTGAGGATTGGG AGTTTATTATTGCTGGCAAGGTACACATTTTCCGCTCACGTTCGGTGCTGGGAC CAAGCTGGAGCTGAAA | Mouse mAb010 light chain DNA sequence |
| 42 | GATGTTGTGATGACCCAGACTCCACTCACTTTGTCGGTTACCATTGGACAACCA GCCTCCATCTCTTGCAAGTCAAGTCAGAGCCTCTTAGATAGTGATGGAAAGAC ATATTTGAATTGGTTGTTACAGAGGCCAGGCCAGTCTCCAAAGCGCCTAATCTA TCTGGTGTCTAAACTGGACTCTGGAGTCCCTGACAGGTTCACTGGCAGTGGAT CAGGGACAGATTTCACACTGAAAATCAGCAGAGTGGAGGCTGAGGATTGGG AGTTTATTATTGCTGGCAAGGTACACATTTTCCATTCACGTTCGGCTCGGGGAC AAAGTTGGAAATAAAA | Mouse mAb011 light chain DNA sequence |
| 43 | GATGTTGTGATGACCCAGACTCCACTCACTTTGTCGGTTACCATTGGACAACCA GCCTCTATCTCTTGCAAGTCAAGTCAGAGCCTCTTATATAGTAATGGAAAAACC TATTTGAATTGGTTATTACAGAGGCCAGGCCAGTCTCCAAAGCGCCTAATCTAT CTGGTGTCTAAACTGGACTCTGGAGTCCCTGACAGGTTCACTGGCAGTGGATC AGGAACAGATTTTACACTGAAAATCAGCAGAGTGGAGGCTGAGGATTTGGGG GTTTATTACTGCGTGCAAGGTACACATTTTCCTCACACGTTCGGAGGGGGGAC CAAGCTGGAAATAAAA | Mouse mAb013 light chain DNA sequence |
| 44 | GATGTTGTGATGACCCAAACTCCACTCTCCCTGCCTGTCAGTCTTGGAGATCAA GCCTCCATCTCTTGCAGATCTAGTCAGAGCCTTGTACACAGTAATGGAAACACC TATTTACATTGGTACCTGCAGAAGCCAGGCCAGTCTCCAAAGCTCCTGATCTAC AAAGTTTCCAACCGATTTTCTGGGGTCCCAGACAGGTTCAGTGGCAGTGGATC AGGGACAGATTTCACACTCAAGATCAGCAGAGTGGAGGCTGAGGATCTGGGA GTTTATTTCTGCTCTCAAAGTACACATGTTCCTCCGTGGACGTTCGGTGGAGGC ACCAAGCTGGAAATCAAA | Mouse mAb020 light chain DNA sequence |
| 45 | GACATTGTGATGACTCAGTCTCCAGCCACCCTGTCTGTGACTCCAGGAGATAG AGTCTCTCTTTCCTGCAGGGCCAGCCAGAGTATTAGCGACTACTTACACTGGTA TCAACAAAAATCACATGAGTCTCCAAGGCTTCTCATCAAATATGCTTCCCAATC CATCTCTGGGATCCCCTCCAGGTTCAGTGGCAGTGGATCAGGGTCAGATTTCA CTCTCAGTATCAACAGTGTGGAACCTGAAGATGTTGGAGTGTATTACTGTCAA AATGGTCACAGCTTTCCGTACACGTTCGGAGGGGGGACCAAGCTGGAAATAA AA | Mouse mAb025 light chain DNA sequence |
| 46 | GATATTTTGATGACCCAAACTCCACTCTCCCTGCCTGTCAGTCTTGGAGATCAA GCCTCCATCTCTTGCAGATCTAGTCAGAGCCATTGTACATAGTAATGGAAACACC TATTTAGAATGGTACCTGCAGAAACCAGGCCAGTCTCCAAAGCTCCTGATCTAC AAAGTTTCCAACCGATTTTCTGGGGTCCCAGACAGGTTCAGTGGCAGTGGATC AGGGACAGATTTCACACTCAAGATCAGCAGAGTGGAGGCTGAGGATCTGGGA GTTTATTACTGCTTTCAAGGTTCACATGTTCCGTACACGTTCGGAGGGGGGACC AAGCTGGAAATAAAA | Mouse mAb032 light chain DNA sequence |
| 47 | GATGTTGTGGTGACTCAAACTCCACTCTCCCTGCCTGTCAGCTTTGGAGATCAA GTTTCTATCTCTTGCAGGTCTAGTCAGAGTCTTGCAAACAGTTATGGGAACACC TATTTGTCTTGGTACCTGCACAAGCCTGGCCAGTCTCCACAGCTCCTCATCTATG GGATTTCCAACAGATTTTCTGGGGTGCCAGACAGGTTCAGTGGCAGTGGTTCA GGGACAGATTTCACACTCAAGATCAGCACAATAAAGCCTGAGGACTTGGGAAT GTATTACTGCTTACAAGGTACACATCAGCCGTGGACGTTCGGTGGAGGCACCA AGCTGGAAATCAAA | Mouse mAb033 light chain DNA sequence |
| 48 | GATGTTGTGATGACCCAGACTCCACTCACTTTGTCGGTTACCATTGGACAACCA GCCTCTATCTCTTGCAAGTCAAGTCAGAGCCTCTTATATAGTAATGGAAAAACC TATTTGAATTGGTTATTACAGAGGCCAGGCCAGTCTCCAAAGCGCCTAATCTAT CTGGTGTCTAAACTGGACTCTGGAGTCCCTGACAGGTTCACTGGCAGTGGATC AGGAACAGATTTTACACTGAAAATCAGCAGAGTGGAGGCTGAGGATTTGGGA GTTTATTACTGCGTGCAAGGTACACATTTTCCTCAGACGTTCGGTGGAGGCACC AAGCTGGAAATCAAA | Mouse mAb037 light chain DNA sequence |

| SEQ ID NO | Sequence | Description |
|---|---|---|
| 109 | GATGTGGTGATGACCCAGTCTCCACTGAGCCTGCCTGTGACCCTGGGCCAACC TGCCAGCATCAGCTGTAAAAGCAGCCAGAGCCTGCTGTACAGCAACGGCAAG ACCTACCTGAACTGGCTGCTGCAGAGACCTGGCCAGAGCCCTAGACGGCTGAT CTACCTGGTGTCCAAGCTGGACAGCGGCGTCCCCGATAGATTCAGCGGATCTG GCAGCGGCACCGACTTCACCCTGAAGATCAGTGAGTGGAAGCCGAGGACGT GGGCGTGTACTACTGCGTGCAGGGCACACACTTCCCCCAGACCTTCGGCGGCG GAACAAAGCTGGAAATCAAG | Humarized mAb037 light chain DNA sequence |
| 49 | SYGMS | Mouse mAb004 heavy chain CDR1 |
| 50 | DYGMH | Mouse mAb005 heavy chain CDR1 |
| 51 | RYWMS | Mouse mAb008 heavy chain CDR1 |
| 52 | GYGVN | Mouse mAb010 heavy chain CDR1 |
| 53 | SYWMH | Mouse mAb011 heavy chain CDR1 |
| 54 | DFYMK | Mouse mAb013 heavy chain CDR1 |
| 55 | SYAVH | Mouse mAb020 heavy chain CDR1 |
| 56 | THGMS | Mouse mAb025 heavy chain CDR1 |
| 57 | SYWMN | Mouse mAb032 heavy chain CDR1 |
| 58 | TFGMGVG | Mouse mAb033 heavy chain CDR1 |
| 59 | DYNMD | Mouse mAb037 heavy chain CDR1 |
| 60 | TISSSGSYTYYPDSVKG | Mouse mAb004 heavy chain CDR2 |
| 61 | YSNSDSTTIYYADTVKG | Mouse mAb005 heavy chain CDR2 |
| 62 | EINPDGNAINYAPSLKD | Mouse mAb008 heavy chain CDR2 |
| 63 | MIWGDGSTDYNSALKS | Mouse mAb010 heavy chain CDR2 |
| 64 | MIDPSDSETRLNQKFKD | Mouse mAb011 heavy chain CDR2 |
| 65 | DIDPNNGDTFYNQKFKG | Mouse mAb013 heavy chain CDR2 |
| 66 | VMWSGGSTDYNAAFIS | Mouse mAb020 heavy chain CDR2 |
| 67 | TYSGVPTYTDDFKG | Mouse mAb025 heavy chain CDR2 |
| 68 | QIYPGDGDTDYNGKFKG | Mouse mAb032 heavy chain CDR2 |
| 69 | HIWWDDDKYYNPALKS | Mouse mAb033 heavy chain CDR2 |
| 70 | DINPNTGGTIYNQKFKG | Mouse mAb037 heavy chain CDR2 |

-continued

| SEQ ID NO | Sequence | Description |
|---|---|---|
| 71 | TYYGAMDY | Mouse mAb004 heavy chain CDR3 |
| 72 | SYYSNYVDY | Mouse mAb005 heavy chain CDR3 |
| 73 | PFPSV | Mouse mAb008 heavy chain CDR3 |
| 74 | WAFAY | Mouse mAb010 heavy chain CDR3 |
| 75 | PYGDLDY | Mouse mAb011 heavy chain CDR3 |
| 76 | DLY | Mouse mAb013 heavy chain CDR3 |
| 77 | MGDYDGVAWFAY | Mouse mAb020 heavy chain CDR3 |
| 78 | SELSWFAY | Mouse mAb025 heavy chain CDR3 |
| 79 | RSPY | Mouse mAb032 heavy chain CDR3 |
| 80 | RGSNALDY | Mouse mAb033 heavy chain CDR3 |
| 81 | EGPYYYGTTHPFAY | Mouse mAb037 heavy chain CDR3 |
| 82 | RSSQTIVHSNGNTYLE | Mouse mAb004 light chain CDR1 |
| 83 | RSSQSLVHSNGNTYLH | Mouse mAb005 light chain CDR1 |
| 84 | RSSQSLVRSNGNTYLE | Mouse mAb008 light chain CDR1 |
| 85 | KSSQSLLDSGGKTYLN | Mouse mAb010 light chain CDR1 |
| 86 | KSSQSLLDSDGKTYLN | Mouse mAb011 light chain CDR1 |
| 87 | KSSQSLLYSNGKTYLN | Mouse mAb013 light chain CDR1 |
| 88 | RASQSISDYLH | Mouse mAb025 light chain CDR1 |
| 89 | RSSQSIVHSNGNTYLE | Mouse mAb032 light chain CDR1 |
| 90 | RSSQSLANSYGNTYLS | Mouse mAb033 light chain CDR1 |
| 91 | KVSNRFS | Mouse mAb004 light chain CDR2 |
| 92 | QVSKLDSGVPD | Mouse mAb010 light chain CDR2 |
| 93 | LVSKLDS | Mouse mAb011 light chain CDR2 |
| 94 | YASQSIS | Mouse mAb025 light chain CDR2 |

SEQUENCE LISTING

| SEQ ID NO | Sequence | Description |
|---|---|---|
| 95 | GISNRFS | Mouse mAb033 light chain CDR2 |
| 96 | FQGSLVPWT | Mouse mAb004 light chain CDR3 |
| 97 | FQSTHVPPT | Mouse mAb005 light chain CDR3 |
| 98 | FQGSHVPYT | Mouse mAb008 light chain CDR3 |
| 99 | WQGTHFPLT | Mouse mAb010 light chain CDR3 |
| 100 | WQGTHFPFT | Mouse mAb011 light chain CDR3 |
| 101 | VQGTHFPHT | Mouse mAb013 light chain CDR3 |
| 102 | SQSTHVPPWT | Mouse mAb020 light chain CDR3 |
| 103 | QNGHSFPYT | Mouse mAb025 light chain CDR3 |
| 104 | LQGTHQPWT | Mouse mAb033 light chain CDR3 |
| 105 | VQGTHFPQT | Mouse mAb037 light chain CDR3 |

What is claimed is:

1. An isolated anti-Tau antibody or antigen-binding moiety thereof comprising:
   a) a heavy chain variable region comprising i) a complementary determining region (CDR) 1 comprising the amino acid sequence of SEQ ID NO: 50; ii) a CDR2 comprising the amino acid sequence of SEQ ID NO: 61; and iii) a CDR3 comprising the amino acid sequence of SEQ ID NO: 72; and
   b) a light chain variable region comprising iv) a CDR1 comprising the amino acid sequence of SEQ ID NO: 83; v) a CDR2 comprising the amino acid sequence of SEQ ID NO: 91; and vi) a CDR3 comprising the amino acid sequence of SEQ ID NO: 97.

2. The antibody or antigen-binding moiety of claim 1, wherein the heavy chain variable region comprises the amino acid sequence of SEQ ID NO: 3 or an amino acid sequence having at least 95% sequence identity to SEQ ID NO: 3.

3. The antibody or antigen-binding moiety of claim 1, wherein the light chain variable region comprises the amino acid sequence of SEQ ID NO: 15 or an amino acid sequence having at least 95% sequence identity to SEQ ID NO: 15.

4. The antibody or antigen-binding moiety of claim 1, wherein the heavy chain variable region comprises the amino acid sequence of SEQ ID NO: 3 or an amino acid sequence having at least 95% sequence identity to SEQ ID NO: 3; and the light chain variable region comprises the amino acid sequence of SEQ ID NO: 15 or an amino acid sequence having at least 95% sequence identity to SEQ ID NO: 15.

5. The antibody or antigen-binding moiety of claim 4, wherein the heavy chain variable region comprises the amino acid sequence of SEQ ID NO: 3; and the light chain variable region comprises the amino acid sequence of SEQ ID NO: 15.

6. The antibody or antigen-binding moiety of claim 1, wherein the antibody or antigen-binding moiety is a monoclonal antibody.

7. The antibody or antigen-binding moiety of claim 1, wherein the antibody or antigen-binding moiety preferentially binds to pathological human Tau species relative to normal human Tau species.

8. The antibody or antigen-binding moiety of claim 7, wherein the pathological human Tau species is:
   from a tauopathy brain;
   Tau aggregates or an abnormally phosphorylated Tau or both;
   Tau aggregates or abnormally phosphorylated accumulated at synapses of brain or both; or
   Tau aggregates or abnormally phosphorylated accumulated at synapses of tauopathy brain or both.

9. The antibody or antigen-binding moiety of claim 1, wherein the antibody or antigen-binding moiety binds to amino acid residues S131, K132, T135, S137 and R155 of a human 2N4R Tau isoform.

10. An isolated anti-Tau antibody or antigen-binding moiety thereof comprising
    a heavy chain variable region comprising CDR1, CDR2, and CDR3 comprised in the amino acid sequence of SEQ ID NO: 3; and a light chain variable region comprising CDR1, CDR2, and CDR3 comprised in the amino acid sequence of SEQ ID NO: 15.

11. A labeled antibody comprising the antibody or antigen-binding moiety of claim 1 and a detectable label.

12. A pharmaceutical composition comprising the antibody or antigen-binding moiety of claim 1 and a pharmaceutically acceptable carrier.

13. The antibody or antigen-binding moiety of claim 1, wherein the heavy chain variable region comprises the amino acid sequence of SEQ ID NO: 2 or an amino acid sequence having at least 95% sequence identity to SEQ ID NO: 2; and the light chain variable region comprises the amino acid sequence of SEQ ID NO: 14 or an amino acid sequence having at least 95% sequence identity to SEQ ID NO: 14.

* * * * *